United States Patent
Boxer et al.

(10) Patent No.: US 9,708,267 B2
(45) Date of Patent: Jul. 18, 2017

(54) ACTIVATORS OF HUMAN PYRUVATE KINASE

(71) Applicant: The United States of America, as represented by the Secretary, Department of Health and Human Services, Washington, DC (US)

(72) Inventors: Matthew B. Boxer, New Market, MD (US); Min Shen, Boyds, MD (US); Douglas S. Auld, Beverly, MA (US); Craig J. Thomas, Gaithersburg, MD (US); Martin J. Walsh, Carmel, IN (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/643,107

(22) Filed: Mar. 10, 2015

(65) Prior Publication Data

US 2015/0183744 A1  Jul. 2, 2015

Related U.S. Application Data

(63) Continuation of application No. 13/643,594, filed as application No. PCT/US2011/033852 on Apr. 26, 2011, now abandoned.

(60) Provisional application No. 61/329,158, filed on Apr. 29, 2010.

(51) Int. Cl.
  *C07D 215/227* (2006.01)
  *C07D 209/30* (2006.01)
  *C07D 215/36* (2006.01)
  *C07D 223/16* (2006.01)
  *C07D 265/36* (2006.01)
  *C07D 209/12* (2006.01)
  *C07D 209/34* (2006.01)
  *C07D 235/26* (2006.01)

(52) U.S. Cl.
  CPC ....... *C07D 215/227* (2013.01); *C07D 209/12* (2013.01); *C07D 209/30* (2013.01); *C07D 209/34* (2013.01); *C07D 215/36* (2013.01); *C07D 223/16* (2013.01); *C07D 235/26* (2013.01); *C07D 265/36* (2013.01)

(58) Field of Classification Search
  CPC  C07D 215/36; C07D 215/227; C07D 209/12; C07D 209/34; C07D 209/30; C07D 223/16; C07D 235/26; C07D 265/36
  See application file for complete search history.

(56) References Cited

U.S. PATENT DOCUMENTS

| | | |
|---|---|---|
| 3,046,122 A | 7/1962 | Süs et al. |
| 3,998,828 A | 12/1976 | Wiedermann |
| 4,235,871 A | 11/1980 | Papahadjopoulos et al. |
| 4,315,940 A | 2/1982 | Hitzel et al. |
| 4,501,728 A | 2/1985 | Geho et al. |
| 4,593,102 A | 6/1986 | Shanklin, Jr. |
| 4,798,897 A | 1/1989 | Hidaka et al. |
| 4,837,028 A | 6/1989 | Allen |
| 5,019,369 A | 5/1991 | Presant et al. |
| 5,216,148 A | 6/1993 | Klaus et al. |
| 5,639,600 A | 6/1997 | McGrath et al. |
| 5,891,435 A | 4/1999 | Muir et al. |
| 5,962,490 A | 10/1999 | Chan et al. |
| 6,020,357 A | 2/2000 | Pinto et al. |
| 6,773,705 B1 | 8/2004 | Faustman et al. |
| 7,087,648 B1 | 8/2006 | McGrath |
| 7,214,673 B2 | 5/2007 | Aicher et al. |
| 7,259,179 B2 | 8/2007 | Burns et al. |
| 7,572,913 B2 | 8/2009 | McKerracher et al. |
| 7,745,629 B2 | 6/2010 | Termin et al. |
| 8,058,313 B2 | 11/2011 | Reddy et al. |

(Continued)

FOREIGN PATENT DOCUMENTS

| | | | |
|---|---|---|---|
| DE | 19755268 | | 6/1999 |
| EP | 504695 | * | 9/1992 |

(Continued)

OTHER PUBLICATIONS

Zubkov, CA151:33377, abstract only of Jzurnal Organichnoi to Farmatsevtichnoi Khimii, 2008, 6(3), 39-44.*
PubChem MLS000086907, Aug. 16, 2005, p. 1.*
Ahmed et al., "M2-PK as a novel marker in ovarian cancer. A prospective cohort study," *Eur. J. Gynaecol. Oncol*, 28 (2), 83-88 (2007) (Abstract).
Anastasiou et al., "Figure 2: TEPP-46 and DASA-58 isoform specificity in vitro and in cells," Nature Chemical Biology, 2012, downloaded Feb. 5, 2014, http://www.nature.com/nchembio/journal/v8/n10/fig_tab/nchembio.1060_F2.html.
Behun et al., "The Chemistry of Pyrazine and Its Derivatives. IV. The Alkylation and Arylation of Methylpyrazine," *J. Org. Chem.*, 26 (9), 3379-3382 (1961).

(Continued)

*Primary Examiner* — D M Seaman
(74) *Attorney, Agent, or Firm* — Leydig, Voit & Mayer, Ltd.

(57) ABSTRACT

Disclosed are pyruvate kinase M2 activators which are compounds of Formula (I), including those of Formula (II), wherein $A^1$, $A^2$, L, R, $R^1$ to $R^3$, $X^1$ to $X^3$, k, n, and m are as defined herein, that are useful in treating a number of diseases that are treatable by the activation of PKM2, for example, cancer. $A^1$-NR-L-$A^2$(I).

(II)

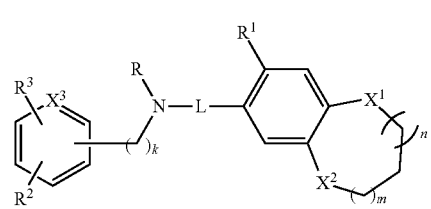

20 Claims, No Drawings

(56) References Cited

U.S. PATENT DOCUMENTS

| | | | |
|---|---|---|---|
| 8,314,125 B2 | 11/2012 | Termin et al. | |
| 8,536,195 B2 | 9/2013 | Termin et al. | |
| 8,642,660 B2 * | 2/2014 | Goldfarb | A61K 31/122 514/18.9 |
| 8,841,305 B2 | 9/2014 | Thomas et al. | |
| 2004/0152648 A1 | 8/2004 | Ullrich et al. | |
| 2005/0176675 A1 | 8/2005 | Gorny | |
| 2007/0032418 A1 | 2/2007 | Shapiro et al. | |
| 2007/0280918 A1 | 12/2007 | Schwartz et al. | |
| 2008/0021116 A1 | 1/2008 | Ullrich et al. | |
| 2008/0044833 A1 | 2/2008 | Connors | |
| 2008/0119453 A1 | 5/2008 | Termin et al. | |
| 2009/0030038 A1 | 1/2009 | Chu et al. | |
| 2009/0048227 A1 | 2/2009 | Chakravarty et al. | |
| 2009/0163545 A1 * | 6/2009 | Goldfarb | A61K 31/122 514/312 |
| 2009/0270454 A1 | 10/2009 | Weingarten et al. | |
| 2010/0179150 A1 | 7/2010 | Basarab et al. | |
| 2010/0204255 A1 | 8/2010 | Termin et al. | |
| 2011/0046083 A1 | 2/2011 | Cantley et al. | |
| 2011/0195958 A1 | 8/2011 | Thomas et al. | |
| 2011/0312931 A1 | 12/2011 | Cioffi et al. | |
| 2012/0245141 A1 | 9/2012 | Thomas et al. | |
| 2013/0045240 A1 | 2/2013 | Tao et al. | |
| 2013/0084639 A1 | 4/2013 | Termin et al. | |
| 2014/0072630 A1 | 3/2014 | Tao et al. | |

FOREIGN PATENT DOCUMENTS

| | | |
|---|---|---|
| EP | 1 586 558 A2 | 10/2005 |
| EP | 1 878 723 A1 | 7/2006 |
| JP | S569749 A | 1/1981 |
| JP | H09286783 A | 11/1997 |
| JP | 2001-511449 A | 8/2001 |
| JP | 2002-138083 A | 5/2002 |
| JP | 2002-536446 A | 10/2002 |
| JP | 2003500470 A | 1/2003 |
| JP | 2003535847 A | 12/2003 |
| JP | 2005008624 A | 1/2005 |
| JP | 2006508906 A | 3/2006 |
| JP | 2008502610 A | 1/2008 |
| JP | 2008-540661 A | 11/2008 |
| JP | 2008-545686 A | 12/2008 |
| JP | 2008545001 A | 12/2008 |
| JP | 2009503117 A | 1/2009 |
| RU | 2261246 C1 | 9/2005 |
| WO | WO 93/13072 A1 | 7/1993 |
| WO | WO 98/03350 A1 | 1/1998 |
| WO | WO 99/06042 A2 | 2/1999 |
| WO | WO 99/06367 A1 | 2/1999 |
| WO | 0047578 A1 | 8/2000 |
| WO | WO 00/53596 A2 | 9/2000 |
| WO | WO 00/73264 A1 | 12/2000 |
| WO | WO 01/22966 A1 | 4/2001 |
| WO | WO 01/94312 A2 | 12/2001 |
| WO | WO 02/095063 A1 | 11/2002 |
| WO | WO 03/082877 A1 | 10/2003 |
| WO | WO 03/106381 A2 | 12/2003 |
| WO | WO 2004/005278 A1 | 1/2004 |
| WO | WO 2005/123688 A2 | 12/2005 |
| WO | WO 2006/004195 A1 | 1/2006 |
| WO | WO 2006/016062 A1 | 2/2006 |
| WO | WO 2006/126939 A1 | 11/2006 |
| WO | WO 2007/003611 A1 | 1/2007 |
| WO | WO 2007/019344 A1 | 2/2007 |
| WO | 2007/076320 A2 | 7/2007 |
| WO | WO 2007/076055 A2 | 7/2007 |
| WO | 2007120638 * | 10/2007 |
| WO | WO 2007/117699 A2 | 10/2007 |
| WO | WO 2007/127505 A2 | 11/2007 |
| WO | WO 2008/018544 A1 | 2/2008 |
| WO | 2008/061016 A1 | 5/2008 |
| WO | 2008/107661 A1 | 9/2008 |
| WO | WO 2008/124838 A1 | 10/2008 |
| WO | WO 2009/025781 A1 | 2/2009 |
| WO | WO 2009025793 A2 | 2/2009 |
| WO | WO 2009/036341 A2 | 3/2009 |
| WO | WO 2009/055418 A1 | 4/2009 |
| WO | WO 2009/084501 | 7/2009 |
| WO | WO 2010/026365 A1 | 3/2010 |
| WO | WO 2010/042867 A2 | 4/2010 |
| WO | 2011025838 A1 | 3/2011 |

OTHER PUBLICATIONS

Boxer et al., "Evaluation of Substituted N, N'-Diarylsulfonamides as Activators of the Tumor Cell Specific M2 Isoform of Pyruvate Kinase," *J. Med. Chem.*, 53 (3), 1048-1055 (2010) (published online Dec. 17, 2009).

Boxer et al., "Identification of activators for the M2 isoform of human pyruvate kinase," retrieved from internet (URL: http://www.ncbi.nlm.nih.gov/books/NBK56225/pdf/ml170.pdf) (retrieved on Jul. 27, 2011).

CA Registry No. 842112-70-3, entered into the Registry File on Mar. 4, 2005, supplied by AsinEx.

Chan et al., "Synthesis and characterization of poly(amide sulfonamide)s (PASAs)," *J. Polymer. Sci.*, 33 (15), 2525-2531 (1995).

Coy et al., "Ambident Neighbouring Groups, Part V. Mechanism of Cyclization of 2-Halogenoethylsulphonamides to Aziridines," *J. Chem. Society, Perkin Transactions* 2, 53-58 (1974).

European Patent Office, Second Examination Report in European Patent Application No. 09740795.1 (Feb. 7, 2013).

Fomchenko et al., "Mouse Models of Brain Tumors and Their Applications in Preclinical Trials," *Clin Cancer Res.*, 12 (18), 5288-5297 (Sep. 15, 2006).

Goldfarb, "Method using lifespan-altering compounds for altering the lifespan of eukaryotic organisms, and screening for such compounds," *Chemical Abstract*, 151, No. 92842 (2009).

Hitosugi et al., "A Malignant Metabolic Switch," *Sci. Signal.*, 97 (2), ra73 (Nov. 17, 2009), Abstract.

Hulleman et al., "Pyruvate kinase M2 and prednisolone resistance in acute lymphoblastic leukemia," *Haematologica*, 94 (9), 1322-1324 (2009).

Inglese et al., "Quantitative high-throughput screening: A titration-based approach that efficiently identifies biological activities in large chemical libraries," *Proc. Natl. Acad. Sci.*, 103 (31), 11473-11478 (2006) (Epub Jul. 24, 2006).

International Preliminary Report on Patentability, Application No. PCT/US2009/060237, dated Apr. 12, 2011.

International Preliminary Report on Patentability, Application No. PCT/US2011/033852, dated Nov. 8, 2012.

Iqbal et al., "Resveratrol inhibits Cancer Cell Metabolism by Down Regulating Pyruvate Kinase M2 via inhibition of Mammalian Target of Rapamycin," *PLOS One*, 7 (5) e36764, 1-8 (May 2012).

International Search Report, Application No. PCT/US2009/060237, dated Jun. 16, 2010.

International Search Report, Application No. PCT/US2011/033852, dated Aug. 3, 2011.

Jiang et al., "Evaluation of thieno[3,2-b]pyrrole[3,2-d]pyridazinones as activators of the tumor cell specific M2 isoform of pyruvate kinase." *Bioorg. Med. Chem. Lett.*, 20 (11), 3387-3393 (2010) (Epub Apr. 11, 2010).

Klapars et al., "A General and Efficient Copper Catalyst for the Amidation of Aryl Halides and the N-Arylation of Nitrogen Heterocycles," *J. Am. Chem. Soc.*, 123 (31), 7727-7729 (2001).

Lawrence et al., "A Preclinical Xenograft Model of Prostate Cancer Using Human Tumors," *Nature Protocols*, 8 (5), 836-848 (2013).

Lee, "Pyruvate kinase isozyme type M2 (PKM2) Interacts and cooperates with Oct-4 in regulating transcription," *International J. Biochem. & Cell Biol.*, 40 (5), 1043-10584 (2008) (Epub Nov. 29, 2007).

Lee et al., "An Efficient Synthesis of 2,8-Diazabicyclo[4.3.0]-Nonane Derivatives via Intramolecular Cyclization Reaction," *Synth. Comm.*, 25 (23), 3741-3746 (1995).

Oeda, "On Some 2,5-Dialkyl-piperazines," *Bull. Chem. Soc.*, 13 (7), 465-470 (1938).

(56) References Cited

OTHER PUBLICATIONS

Paudler et al. "3,7-Disubstituted octahydro-1,5-diazocines. Their conversion into tetrahydro-1,5-diazocines and into ring-contracted products," *J. Org. Chem.*, 32 (8), 2425-2430 1967.
Pollard et al., "Some Amides of Piperazines," *J. Am. Chem. Soc.*, 75 (2), 491 (1953).
Results of Scifinder Structure Search Carried out on Sep. 15, 2008 for U.S. Appl. Nos. 13/433,656 and 13/123,297.
Schroth et al., "RingschluBreaktion von Diacetylen mit Diaminen: Eine Ciniache Synthese von 2,3-Dihydro-1,4-diazepinen," *Zeitschrift Fur Chemie.*, 6 (4), 143 (1969).
Seibel et al., "Synthesis and evaluation of δ-lactams (piperazones) as elastase inhibitors," *Bioorg. Med. Chem. Ltrs.*, 13 (3), 387-389 (2003).
Shi et al., "Silencing of pkm2 increases the efficacy of docetaxel in human lung cancer xenografts in mice," *Cancer Science*, 101 (6), 1447-1453 (2010) (Epub Mar. 15, 2010).
Stewart et al., "Piperazines I. Derivatives of Piperazine-1-Carboxylic and -1,4-Dicarboxylic Acid," *J. Org. Chem.*, 18 (1), 1478-1483 (1953).
Sun et al., "Mammalian target of rapamycin up-regulation of pyruvate kinase isoenzyme type M2 is critical for aerobic glycolysis and tumor growth," *PNAS Early Edition*, 1-6 (2011).
Szoka et al., "Comparative properties and methods of preparation of lipid vesicles (liposomes)," *Ann. Rev. Biophys. Bioeng.*, 9, 467-508 (1980).
Uozumi et al., "Catalytic asymmetric construction of morpholines and piperazines by palladium-catalyzed tandem allylic substitution reactions," *J. Org. Chem.*, 58 (24), 6826-6832 (1993).
Walsh et al., "2-oxo-N-aryl-1,2,3,4-tetrahydroquinoline-6-sulfonamides as activators of the tumor cell specific M2 isoform of pyruvate kinase," *Bioorg. Med. Chem. Lett.*, 21 (21), 6322-6327 (2011) (Epub date Sep. 14, 2011), author manuscript.
Wong et al., "PKM2, a Central Point of Regulation in Cancer Metabolism," *International J. Cell Biology*, Article ID 242513, 1-11 (2013).
Written Opinion of the International Searching Authority, Application No. PCT/US2009/060237 dated Apr. 9, 2011.
Written Opinion of the International Searching Authority, Application No. PCT/US2011/033852, dated Aug. 3, 2011.
Yar et al., "An Annulation Reaction for the Synthesis of Morpholines, Thiomorpholines, and Piperazines from β-Heteroatom Amino Compounds and Vinyl Sulfonium Salts," *Angewandte Chemie.*, 47 (20), 3784-3786 (2008).
Zhou et al., "Pyruvate Kinase Type M2 Is Upregulated in Colorectal Cancer and Promotes Proliferation and Migration of Colon Cancer Cells," *Life*, 64 (9), 775-782 (Sep. 2012).
Zubkov, ca 151:33377, Zhurnal Organ ta Farmatsevtichnoi Khimii, 6 (3), 39-44, 2008 (full article).
Laborde et al., "Traceless, Self-Cleaving Solid- and Solution-Phase Parallel Synthesis of 3,4,7-Trisubstituted 3,4-Dihydroquinoxalin-2-ones," *J. Comb. Chem*, 3, 572-577 (2001).
Japanese Patent Office: First Examination Report in Japanese Patent Application No. 2013-508139 (Dec. 24, 2014).
STN International Registry File (Online), CAS Registration Nos. RN:1174853-67-8, 1030222-01-5, 1029781-71-2, 1001881-57-7, 1001828-3-6-9, 949676-42-0, 912797-10-5, 912796-94-2, 912788-04-6, 912782-41-3, 912760-060-2, 912760-57-7, 909090-99-9, 909089-35-6, 902602-67-9, 901036-91-7, 899717-26-1, 891919-47-4, 891908-74-0, 891892-67-4, 879178-9, 3-5, 879178-88-8, 878949-29-2, 838900-70-2, 8388887-37-9, 701969-93-9, 687593-47-1, 687593-46-0.
Australian Patent Office: Patent Examination Report No. 2 in Australian Patent Application No. 2011245441 (Mar. 18, 2014).
European Patent Office: Communication pursuant to Rules 161(1) and 162 EPC in European Patent Application No. 11730473.3 (Dec. 6, 2012).
European Patent Office: Communication pursuant to Article 94(3) EPC in European Patent Application No. 11730473.3 (Aug. 20, 2013).
European Patent Office: Communication pursuant to Article 94(3) EPC in European Patent Application No. 11730473.3 (Aug. 21, 2014).
U.S. Appl. No. 13/433,656, filed Mar. 29, 2012.
U.S. Appl. No. 13/123,297, filed Apr. 8, 2011.
U.S. Appl. No. 14/576,333, filed Dec. 19, 2014.
Australian Patent Office: Patent Examination Report No. 1 in Australian Patent Application No. 2015201398 (Dec. 10, 2015) 3 pages.
Australian Patent Office: Patent Examination Report No. 1 in Australian Patent Application No. 2011245441 (Mar. 7, 2014) 4 pages.
Japanese Patent Office: Second Examination Report in Japanese Patent Application No. 2013-508139 (Oct. 6, 2015) 10 pages.
STN International Registry File (Online), CAS Registration Nos. RN: 1214560-19-6, 1214537-09-3, 1214467-72-7, 1214401-60-1, 1211279-63-8, 1210422-77-7, 1209745-30-1, 1209687-09-1, 1147812-94-9, 1147723-81-6, 1119227-32-5, 1111573-79-5, 1111537-54-2, 1111451-45-6, 1090860-23-3, 1089583-64-1, 1061003-83-5, 1030765-14-0, 1030169-54-0, 1016090-35-9, 1016051-53-8, 1014874-72-6, 1014257-41-0, 1014221-11-4, 1014221-05-6, 1011060-74-4, 1009898-06-9, 1008422-10-3, 1007737-46-3, 1004149-63-6, 1004149-62-5, 1004149-61-4, 1004149-60-3, 1002946-34-0, 1002455-23-3, 1002454-99-0, 1002171-86-9, 1002170-88-8, 1002170-60-6, 1002170-57-1, 1002170-01-5, 1001881-33-9, 1001828-01-8, 1001581-19-6, 1001581-06-1, 1001581-04-9, 1001580-98-8, 958720-38-2, 958715-93-0, 958700-39-5, 950152-41-7, 949997-57-3, 949867-81-6, 949842-38-0, 949237-68-7, 940802-16-4, 933006-02-1, 931731-22-5, 931630-74-9, 931029-07-1, 930964-32-2, 930960-95-5, 930901-79-4, 930396-51-3, 924399-03-1, 924382-47-8, 924377-34-4, 924173-15-9, 924075-62-7, 923899-42-7, 923856-25-1, 920846-52-2, 920724-85-2, 920721-27-3, 920628-14-4, 920625-36-1, 919880-08-3, 912796-97-5, 912796-92-0, 912787-84-9, 912787-68-9, 912787-58-7, 912782-66-2, 912782-52-6, 912782-45-7, 912760-66-8, 912760-63-5, 912760-47-5, 912760-30-6, 912760-25-9, 912760-08-8, 912759-81-0, 912759-77-4, 912759-70-7, 909208-28-2, 899717-24-9, 879178-98-0, 868269-04-9, 697258-33-6, 697258-29-0, 687593-48-2, 33 pages.
The Practice of Medicinal Chemistry, vol. 1 of 2, pp. 423-425 (Aug. 15, 1998) 6 pages.
Cecil Textbook of Medicine, edited by Bennet, J.C., and Plum F., $20^{th}$ edition, vol. 1, 1004-101 O, (1996).
Cohen et al., *Current Opinion in Chemical Biology*, 3, 459-465, (1999).
Communication issued in European Patent Application No. 11730473.3 (Jul. 13, 2016) 7 pages.
Dermer et al., Bio/Technology, 12:320 (1994).
Examination Report issued in Australian Patent Application No. 2009303335 (Sep. 2, 2015) 11 pages.
Freshney et al., Culture of Animal Cells, A Manual of Basic Technique, Alan R. Liss, Inc., New York, 4, (1983).
Golub et al., *Science* 286: 531-537 (1999).
Hulleman et al., "Pyruvate kinase M2 and prednisolone resistance in acute lymphoblastic leukemia," *Haematologica*, 94(9): 1322-1324 (Sep. 2009), Abstract.
Lee et al., "An Efficient Synthesis of 2,8-Diazabicyclo[4.3.0]-Nonane Derivatives Via Intramolecular Cyclization Reaction," *Synth. Comm.*, 25 (23): 3741-3746 (1995).
CAS Registry No. 1013273-80-7, STN Entry date Apr. 9, 2008, 1 page.
CAS Registry No. 796092-26-7, STN Entry date Dec. 10, 2004, 1 page.
CAS Registry No. 1186650-24-7, STN Entry date Sep. 30, 2009, 1 page.
CAS Registry No. 1186650-83-8, STN Entry date Sep. 30, 2009, 1 page.
CAS Registry No. 1186660-06-9, STN Entry date Sep. 30, 2009, 1 page.
First Office Action issued in Japanese Patent Application No. 2014-207672 (Dec. 8, 2015) 14 pages.
McMahon, "VEGF Receptor Signaling in Tumor Angiogenesis" *The Oncologist(suppl 1)*: 3-10 (2000).

(56) References Cited

OTHER PUBLICATIONS

Pinedo et al., "Translation Research: The Role of VEGF in Tumor Angiogenesis" *The Oncologist*(*suppl 1*):1-2 (2000).
STN International Registry File (Online), RN: 1011002-90-6, 1010028-21-3, 950108-01-7, 941044-20-8, 930930-19-1, 927571-25-3, 920669-97-2, 920633-09-6, 919932-51-7, 876904-33-5, 874640-84-3, 870984-40-0, 870984-39-7, 851871-50-6, 851871-44-8, 851792-70-6, 745030-25-5, 562867-96-3, 516477-40-0, 448249-96-5.
Compounds from http://online.aurorafinechemicals.com/ (6 pages).

\* cited by examiner

ACTIVATORS OF HUMAN PYRUVATE KINASE

CROSS-REFERENCE TO A RELATED APPLICATION

This patent application is a Continuation of U.S. patent application Ser. No. 13/643,594, filed Jan. 16, 2013, which is a U.S. National Phase of PCT/US2011/033852, filed Apr. 26, 2011, which claims the benefit of U.S. provisional patent application No. 61/329,158, filed Apr. 29, 2010, each of which is incorporated by reference herein.

BACKGROUND OF THE INVENTION

Pyruvate kinase (PK) is a critical metabolic enzyme operating at the ultimate step in glycolysis where it catalyzes the transfer of a phosphate group from phosphoenolpyruvate to adenosine diphosphate (ADP), yielding one molecule of pyruvate and one molecule of adenosine triphosphate (ATP). In humans there are two pyruvate kinase genes and each produces two distinct gene products by alternative splicing. The L gene produces two different mRNAs that differ only in the first exon to produce the L (liver specific) and R (red blood cell) specific isozymes. Splicing of a single exon within the M gene produces the M1 isozyme that is found in most adult tissues and the M2 isozyme that is present in fetal tissues and is found to be re-expressed in tumors. Therefore, after embryonic development, adult tissues switch to either express PK-M1 or the tissue specific L or R isozymes. However, in all tumors or cell lines of cancer lineage (including those typically expressing either the L or R isozymes), PK gene expression reverts entirely to the M2 isoform.

PK is a tetrameric enzyme composed of four identical monomers that form a dimer of dimers in the final tetrameric structure. In humans, the M2, L, and R isozymes are activated by fructose-1,6-bis phosphate (FBP) that binds to a flexible loop region at the interface of the two dimers. Activation of PK shifts the enzyme to a state showing high affinity for phosphoenolpyruvate (PEP). In contrast, the M1 isoform is not regulated by FBP and displays only high affinity PEP binding similar to the activated state of PK.

Tumor cells undergo a metabolic transformation that is required to supply the biochemical precursors necessary for rapid cell growth and proliferation. Knock-down of PKM2 and re-expression of PKM1 has been shown to significantly diminish the proliferation of cancer cells in vivo such that even when tumors do grow, they have delayed formation and re-expression of PKM2.

Various phosphotyrosine peptides can bind to PK-M2 near the activation loop that results in the removal of FBP from the enzyme which effectively down-regulates PK-M2 activity. These peptides are present in exacerbated levels in cancer cells. When PK-M2 is activated, glucose is converted to pyruvate. However, when PK-M2 is inactivated, a build-up of glycolytic intermediates occurs which intermediates can be diverted towards nucleotide and lipid biosynthesis required for cell growth and proliferation.

Methods for detecting activators of PK-M2 are known. However, there is a desire for the identification of new activators of PK-M2.

BRIEF SUMMARY OF THE INVENTION

The present invention provides compounds that are activators of the M2 isoform of human pyruvate kinase. In addition, the present invention provides compositions comprising these compounds and methods of using these compound as therapeutic agents in the treatment or prevention of cancer.

The invention provides a compound of formula (I):

$$A^1\text{-NR-L-}A^2 \qquad (I)$$

wherein $A^1$ and $A^2$ are each individually R' or R";
wherein R is H or $C_1$-$C_4$ alkyl;
wherein L is $SO_2$ or CO;
wherein R' is a fused bicyclic ring, wherein one ring of the bicyclic ring is phenyl which is linked to the NR-L moiety at the nitrogen atom or the sulfur atom when L is $SO_2$ or the carbon atom when L is CO and the other ring of the bicyclic ring is an aryl, a heteroaryl, a cyclyl, or a heterocyclyl, wherein R∝ is optionally substituted on one or both rings with one or more substituents selected from the group consisting of aryl, heteroaryl, cyclyl, alkyl, alkoxyl, halogen, $NH_2$, NH—($C_1$-$C_4$)alkyl, N—($C_1$-$C_4$)alkyl-($C_1$-$C_4$)alkyl, ($C_1$-$C_4$)alkyl-CO—, and heterocyclyl, each of which other than halogen and $NH_2$ is further optionally substituted with one or more substituents selected from the group consisting of $NH_2$, OH, NH—($C_1$-$C_4$)alkyl and N—($C_1$-$C_4$)alkyl-($C_1$-$C_4$)alkyl; and wherein R" is phenyl, benzyl, or heteroaryl, which is optionally substituted with one or more substituents selected from the group consisting of halogen, $C_1$-$C_4$ alkyl, $C_1$-$C_4$ alkoxyl, cyano, alkylenedioxy, aryl, heteroaryl, benzyl, $B(OH)_2$, and $C_1$-$C_4$ alkyl substituted with one or more halogens, or is phenyl optionally fused with an aryl, a heteroaryl, a cyclyl, or a heterocyclyl, each of which is optionally substituted with one or more substituents selected from the group consisting of halogen, $C_1$-$C_4$ alkyl, $C_1$-$C_4$ alkoxyl, alkylenedioxy, aryl, heteroaryl, benzyl, and $C_1$-$C_4$ alkyl substituted with one or more halogens;

or a pharmaceutically acceptable salt thereof.

The invention also provides a pharmaceutical composition comprising a compound or salt of the invention and a pharmaceutically acceptable carrier.

The invention further provides a method for treating cancer comprising administering to a patient in need thereof a therapeutically effective amount of a compound of the invention to a mammal afflicted therewith.

DETAILED DESCRIPTION OF THE INVENTION

In accordance with an embodiment, the invention provides a compound of formula (I):

$$A^1\text{-NR-L-}A^2 \qquad (I)$$

wherein $A^1$ and $A^2$ are each individually R' or R";
wherein R is H or $C_1$-$C_4$ alkyl;
wherein L is $SO_2$ or CO;
wherein R' is a fused bicyclic ring, wherein one ring of the bicyclic ring is phenyl which is linked to the NR-L moiety at the nitrogen atom or the sulfur atom when L is $SO_2$ or the carbon atom when L is CO and the other ring of the bicyclic ring is an aryl, a heteroaryl, a cyclyl, or a heterocyclyl, wherein R' is optionally substituted on one or both rings with one or more substituents selected from the group consisting of aryl, heteroaryl, cyclyl, alkyl, alkoxyl, halogen, $NH_2$, NH—($C_1$-$C_4$)alkyl, N—($C_1$-$C_4$)alkyl-($C_1$-$C_4$)alkyl, ($C_1$-$C_4$) alkyl-CO—, and heterocyclyl, each of which other than halogen and $NH_2$ is further optionally substituted with one or more substituents selected from the group consisting of $NH_2$, OH, NH—($C_1$-$C_4$)alkyl and N—($C_1$-$C_4$)alkyl-($C_1$-$C_4$) alkyl; and wherein R" is phenyl, benzyl, or heteroaryl, which is optionally substituted with one or more substituents selected from the group consisting of halogen, $C_1$-$C_4$ alkyl, $C_1$-$C_4$ alkoxyl, cyano, alkylenedioxy, aryl, heteroaryl, benzyl, $B(OH)_2$, and $C_1$-$C_4$ alkyl substituted with one or more halogens, or is phenyl optionally fused with an aryl, a heteroaryl, a cyclyl, or a heterocyclyl, each of which is optionally substituted with one or more substituents selected from the group consisting of halogen, $C_1$-$C_4$ alkyl, $C_1$-$C_4$ alkoxyl, alkylenedioxy, aryl, heteroaryl, benzyl, and $C_1$-$C_4$ alkyl substituted with one or more halogens;

or a pharmaceutically acceptable salt thereof.

In an embodiment, $A_1$ is R" and $A^2$ is R'.

In another embodiment, the phenyl ring of the bicyclic ring of R' is fused with an aryl, a heteroaryl, a cyclyl, or a heterocyclyl, each of which is optionally substituted with one or more substituents selected from the group consisting of aryl, heteroaryl, cyclyl, alkyl, alkoxyl, halogen, $NH_2$, NH—($C_1$-$C_4$)alkyl, N—($C_1$-$C_4$)alkyl-($C_1$-$C_4$)alkyl, ($C_1$-$C_4$)alkyl-CO—, and heterocyclyl, each of which other than halogen and $NH_2$ is further optionally substituted with one or more substituents selected from the group consisting of $NH_2$, OH, NH—($C_1$-$C_4$)alkyl and N—($C_1$-$C_4$)alkyl-($C_1$-$C_4$)alkyl.

In certain embodiments, the cyclyl or heterocyclyl of R' or R" is a five-membered, six-membered, or seven-membered ring.

In particular embodiments, the heterocyclyl contains one or two heteroatoms.

In preferred embodiments, R is methyl or H.

In any embodiments of the above, R' is

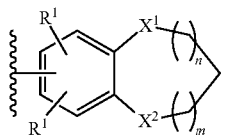

wherein $X^1$ and $X^2$ are each individually O, $NR^6$, or $CR^7R^8$;

wherein any $CH_2$—$CH_2$ moiety within the ring containing $X^1$ and $X^2$ is optionally replaced with a CH=CH moiety;

wherein any NH—$CH_2$ moiety within the ring containing $X^1$ and $X^2$ is optionally replaced with a N=CH moiety;

wherein any methylene of the ring containing $X^1$ and $X^2$ is optionally replaced by a carbonyl;

wherein n and m are each individually 0, 1, or 2, and wherein n+m is 0 to 2;

wherein each $R^1$ is individually H, halogen, alkyl, alkoxyl, $NH_2$, NH—($C_1$-$C_4$)alkyl, N—($C_1$-$C_4$)alkyl-($C_1$-$C_4$)alkyl, aryl, heteroaryl, cyclyl, or heterocyclyl, each of which other than halogen and $NH_2$ is further optionally substituted with one or more substituents selected from the group consisting of $NH_2$, OH, NH—($C_1$-$C_4$)alkyl and N—($C_1$-$C_4$)alkyl-($C_1$-$C_4$)alkyl;

wherein $R^6$ is H, alkyl, alkylcarboxy, aryl, heteroaryl, cyclyl, or heterocyclyl, each of which is further optionally substituted with one or more substituents selected from the group consisting of $NH_2$, OH, NH—($C_1$-$C_4$)alkyl and N—($C_1$-$C_4$)alkyl-($C_1$-$C_4$)alkyl; and wherein $R^7$ and $R^8$ are each individually H, halogen, alkyl, alkoxyl, $NH_2$, NH—($C_1$-$C_4$)alkyl, N—($C_1$-$C_4$)alkyl-($C_1$-$C_4$)alkyl, aryl, heteroaryl, cyclyl, or heterocyclyl, each of which other than halogen and $NH_2$ is further optionally substituted with one or more substituents selected from the group consisting of $NH_2$, OH, NH—($C_1$-$C_4$)alkyl and N—($C_1$-$C_4$)alkyl-($C_1$-$C_4$)alkyl.

In another embodiment, one $R^1$ is at the ortho position relative to the carbon attached to the NR-L moiety.

In another embodiment, one $R^1$ is H, F, Cl, Br, methyl, N(Me)$_2$, NHMe, 1-piperidinyl, 2-(dimethylamino)ethyl)(methyl)amino, pyrrolidin-1-yl, 3-(dimethylamino)pyrrolidin-1-yl, 2-hydroxy-2-methylpropylamino, isopropylamino, diethylamino, 1-hydroxypropan-2-ylamino, 2-hydroxyethylamino, or phenyl.

Additional embodiments include where R' is optionally substituted with one or more substituents selected from the group consisting of methyl and acetyl.

In keeping with the embodiments above, R' is 3,4-dihydroquinolin-2(1H)-onyl, indolin-2-onyl, 4,5-dihydro-1H-benzo[b]azepin-2(3H)-onyl, 2H-benzo[b][1,4]oxazin-3(4H)-onyl, 4-methyl-2H-benzo[b][1,4]oxazin-3(4H)-onyl, 1H-benzo[d]imidazol-2(3H)-onyl, 1,3-dimethyl-1H-benzo[d]imidazol-2(3H)-onyl, 1-(indolin-1-yl)ethanonyl, 1-methyl-1H-indolyl, 1-acetyl-2-methylindolinyl, 6-chloro-2-oxoindolinyl, 3,3-dichloro-2-oxoindolinyl, 7-((2-(dimethylamino)ethyl)(methyl)amino)-2-oxo-1,2,3,4-tetrahydroquinolinyl, 2-oxo-7-(pyrrolidin-1-yl)-1,2,3,4-tetrahydroquinolinyl, 7-(3-(dimethylamino)pyrrolidin-1-yl)-2-oxo-1,2,3,4-tetrahydroquinolinyl, 7-(2-hydroxy-2-methylpropylamino)-2-oxo-1,2,3,4-tetrahydroquinolinyl, 7-(isopropylamino)-2-oxo-1,2,3,4-tetrahydroquinolinyl, 7-(diethylamino)-2-oxo-1,2,3,4-tetrahydroquinolinyl, 7-(2-hydroxyethylamino)-2-oxo-1,2,3,4-tetrahydroquinolinyl, 7-(1-hydroxypropan-2-ylamino)-2-oxo 1,2,3,4-tetrahydroquinolinyl, (S)-7-(1-hydroxypropan-2-ylamino)-2-oxo-1,2,3,4-tetrahydroquinolinyl, or (R)-7-(1-hydroxypropan-2-ylamino)-2-oxo-1,2,3,4-tetrahydroquinolinyl.

In any of the embodiments above R" is

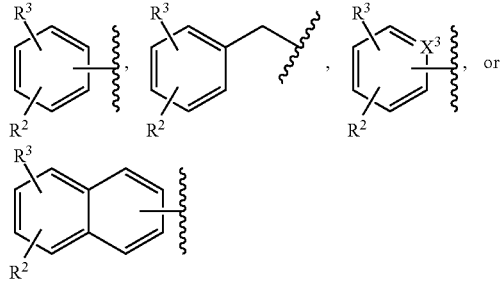

wherein $X^3$ is N or CH wherein when $X^3$ is N, the NR-L moiety is linked to a C of the ring containing $X^3$;

wherein $R^2$ and $R^3$ are each individually H, halogen, $C_1$-$C_4$ alkyl, $C_1$-$C_4$ alkoxyl, cyano, $B(OH)_2$, phenyl, $C_1$-$C_4$ alkyl substituted with one or more halogens, or taken together form alkylenedioxyl.

Another embodiment is where $R^2$ and $R^3$ are each individually H, F, Cl, Br, methyl, methoxy, cyano, trifluoromethyl, phenyl, $B(OH)_2$, or taken together form alkylenedioxyl.

In a particular embodiment of the compounds described above, R" is 3,4-dimethylphenyl, 3-chlorophenyl, meta-tolyl, 3-methoxyphenyl, 3-fluorophenyl, 3-trifluoromethylphenyl, biphenyl-3-yl, pyridine-3-yl, 4-chlorophenyl, para-tolyl, 4-methoxyphenyl, 4-fluorophenyl, ortho-tolyl, 2-methoxyphenyl, 2-fluorophenyl, naphthalen-2-yl, naphthalen-1-yl, 2,3-dihydrobenzo[b][1,4]dioxin-6-yl, benzyl, 3-chloro-4-methylphenyl, 3,4-dichlorophenyl, 5-chloro-2-methylphenyl, 3-cyanophenyl, 3-chloro-2-methylphenyl, 3-phenylboronic acid, 4-fluoro-3-methylphenyl, 3-fluoro-4-methylphenyl, 4-chloro-3-methylphenyl, or 3-chloro-4-fluorophenyl.

In a particular embodiment, the compound of formula (I) is a compound of formula (II):

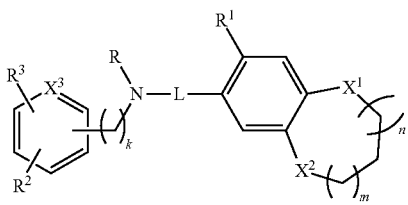

(II)

wherein $X^1$ and $X^2$ are each individually O, $NR^6$, or $CR^7R^8$;

wherein $X^3$ is N or CH wherein when $X^3$ is N, the NR-L moiety is linked to a C of the ring containing $X^3$;

wherein any $CH_2$—$CH_2$ moiety within the ring containing $X^1$ and $X^2$ is optionally replaced with a CH=CH moiety;

wherein any NH—$CH_2$ moiety within the ring containing $X^1$ and $X^2$ is optionally replaced with a N=CH moiety;

wherein any methylene of the ring containing $X^1$ and $X^2$ is optionally replaced by a carbonyl;

wherein n and m are each individually 0, 1, or 2, and wherein n+m is 0 to 2;

wherein k is 0 or 1;

wherein $R^1$ is H, halogen, alkyl, alkoxyl, $NH_2$, NH—($C_1$-$C_4$)alkyl, N—($C_1$-$C_4$)alkyl-($C_1$-$C_4$)alkyl, aryl, heteroaryl, cyclyl, or heterocyclyl, each of which other than halogen and $NH_2$ is further optionally substituted with one or more substituents selected from the group consisting of $NH_2$, OH, NH—($C_1$-$C_4$)alkyl and N—($C_1$-$C_4$)alkyl-($C_1$-$C_4$)alkyl;

wherein $R^2$ and $R^3$ are each individually H, halogen, $C_1$-$C_4$ alkyl, $C_1$-$C_4$ alkoxyl, cyano, $B(OH)_2$, phenyl, $C_1$-$C_4$ alkyl substituted with one or more halogens, or taken together form alkylenedioxy or phenyl fused to a CH:CH moiety of the ring containing $X^3$;

wherein $R^6$ is H, alkyl, alkylcarboxy, aryl, heteroaryl, cyclyl, or heterocyclyl, each of which is further optionally substituted with one or more substituents selected from the group consisting of $NH_2$, OH, NH—($C_1$-$C_4$)alkyl and N—($C_1$-$C_4$)alkyl-($C_1$-$C_4$)alkyl; and wherein $R^7$ and RX are each individually H, halogen, alkyl, alkoxyl, $NH_2$, NH—($C_1$-$C_4$)alkyl, N—($C_1$-$C_4$)alkyl-($C_1$-$C_4$)alkyl, aryl, heteroaryl, cyclyl, or heterocyclyl, each of which other than halogen and $NH_2$ is further optionally substituted with one or more substituents selected from the group consisting of $NH_2$, OH, NH—($C_1$-$C_4$)alkyl and N—($C_1$-$C_4$)alkyl-($C_1$-$C_4$)alkyl.

In a particular embodiment of formula II, $R^1$ is H, F, Cl, Br, methyl, $N(Me)_2$, NHMe, 1-piperidinyl, 2-(dimethylamino)ethyl)(methyl)amino, pyrrolidin-1-yl, 3-(dimethylamino)pyrrolidin-1-yl, 2-hydroxy-2-methylpropylamino, isopropylamino, diethylamino, 1-hydroxypropan-2-ylamino, 2-hydroxyethylamino, or phenyl.

In an embodiment of formula II, the moiety

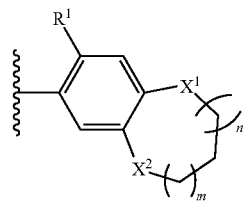

is optionally substituted with one or more substituents selected from the group consisting of methyl and acetyl.

In yet another embodiment of formula II, the moiety

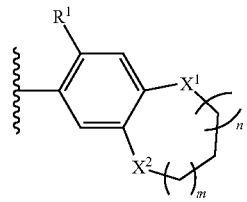

is 3,4-dihydroquinolin-2(1H)-onyl, indolin-2-onyl, 4,5-dihydro-1H-benzo[b]azepin-2(3H)-onyl, 2H-benzo[b][1,4]oxazin-3(4H)-onyl, 4-methyl-2H-benzo[b][1,4]oxazin-3(4H)-onyl, 1H-benzo[d]imidazol-2(3H)-onyl, 1,3-dimethyl-1H-benzo[d]imidazol-2(3H)-onyl, 1-(indolin-1-yl)ethanonyl, 1-methyl-1H-indolyl, 1-acetyl-2-methylindolinyl, 6-chloro-2-oxoindoline, 3,3-dichloro-2-oxoindolinyl, 7-((2-(dimethylamino)ethyl)(methyl)amino)-2-oxo-1,2,3,4-tetrahydroquinolinyl, 2-oxo-7-(pyrrolidin-1-yl)-1,2,3,4-tetrahydroquinolinyl, 7-(3-(dimethylamino)pyrrolidin-1-yl)-2-oxo-1,2,3,4-tetrahydroquinolinyl, 7-(2-hydroxy-2-methylpropylamino)-2-oxo-1,2,3,4-tetrahydroquinolinyl, 7-(isopropylamino)-2-oxo-1,2,3,4-tetrahydroquinolinyl, 7-(diethylamino)-2-oxo-1,2,3,4-tetrahydroquinolinyl, 7-(2-hydroxyethylamino)-2-oxo-1,2,3,4-tetrahydroquinolinyl, 7-(1-hydroxypropan-2-ylamino)-2-oxo-1,2,3,4-tetrahydroquinolinyl, (S)-7-(1-hydroxypropan-2-ylamino)-2-oxo-1,2,3,4-tetrahydroquinolinyl, or (R)-7-(1-hydroxypropan-2-ylamino)-2-oxo-1,2,3,4-tetrahydroquinolinyl.

In another embodiment of formula II, $R^2$ and $R^3$ are each individually H, F, Cl, Br, methyl, methoxy, cyano, trifluoromethyl, phenyl, $B(OH)_2$, or taken together form alkylenedioxyl or phenyl fused to a CH:CH moiety of the ring containing $X^3$.

In accordance with an embodiment of formula II, the moiety

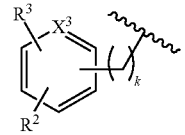

is 3,4-dimethylphenyl, 3-chlorophenyl, meta-tolyl, 3-methoxyphenyl, 3-fluorophenyl, 3-trifluoromethylphenyl, biphenyl-3-yl, pyridin-3-yl, 4-chlorophenyl, para-tolyl, 4-methoxyphenyl, 4-fluorophenyl, ortho-tolyl, 2-methoxyphenyl, 2-fluorophenyl, naphthalen-2-yl, naphthalen-1-yl, 2,3-dihydrobenzo[b][1,4]dioxin-6-yl, benzyl, 3-chloro-4-methylphenyl, 3,4-dichlorophenyl, 5-chloro-2-methylphenyl, 3-cyanophenyl, 3-chloro-2-methylphenyl, 3-phenylboronic acid, 4-fluoro-3-methylphenyl, 3-fluoro-4-methylphenyl, 4-chloro-3-methylphenyl, or 3-chloro-4-fluorophenyl.

Specific examples of the compound described above include

N-(3,4-dimethylphenyl)-2-oxo-1,2,3,4-tetrahydroquinoline-6-sulfonamide,
N-(3,4-dimethylphenyl)-2-oxoindoline-5-sulfonamide,
N-(3,4-dimethylphenyl)-2-oxo-2,3,4,5-tetrahydro-1H-benzo[b]azepine-7-sulfonamide,
N-(3,4-dimethylphenyl)-3-oxo-3,4-dihydro-2H-benzo[b][1,4]oxazine-6-sulfonamide,
N-(3,4-dimethylphenyl)-4-methyl-3-oxo-3,4-dihydro-2H-benzo[b][1,4]oxazine-6-sulfonamide,
N-(3,4-dimethylphenyl)-2-oxo-2,3-dihydro-1H-benzo[d]imidazole-5-sulfonamide,
N-(3,4-dimethylphenyl)-1,3-dimethyl-2-oxo-2,3-dihydro-1H-benzo[d]imidazole-5-sulfonamide,
1-acetyl-N-(3,4-dimethylphenyl)indoline-5-sulfonamide,
N-(3,4-dimethylphenyl)-1-methyl-1H-indole-5-sulfonamide,
N-(3-chlorophenyl)-2-oxo-1,2,3,4-tetrahydroquinoline-6-sulfonamide,
2-oxo-N-m-tolyl-1,2,3,4-tetrahydroquinoline-6-sulfonamide,
N-(3-methoxyphenyl)-2-oxo-1,2,3,4-tetrahydroquinoline-6-sulfonamide,
N-(3-fluorophenyl)-2-oxo-1,2,3,4-tetrahydroquinoline-6-sulfonamide,
2-oxo-N-(3-(trifluoromethyl)phenyl)-1,2,3,4-tetrahydroquinoline-6-sulfonamide,
N-(biphenyl-3-yl)-2-oxo-1,2,3,4-tetrahydroquinoline-6-sulfonamide,
2-oxo-N-(pyridin-3-yl)-1,2,3,4-tetrahydroquinoline-6-sulfonamide,
N-(4-chlorophenyl)-2-oxo-1,2,3,4-tetrahydroquinoline-6-sulfonamide,
2-oxo-N-p-tolyl-1,2,3,4-tetrahydroquinoline-6-sulfonamide,
N-(4-methoxyphenyl)-2-oxo-1,2,3,4-tetrahydroquinoline-6-sulfonamide,
N-(4-fluorophenyl)-2-oxo-1,2,3,4-tetrahydroquinoline-6-sulfonamide,
2-oxo-N-o-tolyl-1,2,3,4-tetrahydroquinoline-6-sulfonamide,
N-(2-methoxyphenyl)-2-oxo-1,2,3,4-tetrahydroquinoline-6-sulfonamide,
N-(2-fluorophenyl)-2-oxo-1,2,3,4-tetrahydroquinoline-6-sulfonamide,
N-(naphthalen-2-yl)-2-oxo-1,2,3,4-tetrahydroquinoline-6-sulfonamide,
N-(naphthalen-1-yl)-2-oxo-1,2,3,4-tetrahydroquinoline-6-sulfonamide,
N-(2,3-dihydrobenzo[b][1,4]dioxin-6-yl)-2-oxo-1,2,3,4-tetrahydroquinoline-6-sulfonamide,
N-benzyl-2-oxo-1,2,3,4-tetrahydroquinoline-6-sulfonamide,
N-(3,4-dimethylphenyl)-7-fluoro-2-oxo-1,2,3,4-tetrahydroquinoline-6-sulfonamide,
7-(dimethylamino)-N-(3,4-dimethylphenyl)-2-oxo-1,2,3,4-tetrahydroquinoline-6-sulfonamide,
N-(3,4-dimethylphenyl)-7-(methylamino)-2-oxo-1,2,3,4-tetrahydroquinoline-6-sulfonamide,
N-(3,4-dimethylphenyl)-2-oxo-7-(piperidin-1-yl)-1,2,3,4-tetrahydroquinoline-6-sulfonamide,
6-chloro-N-(3,4-dimethyl phenyl)-2-oxo-1,2,3,4-tetrahydroquinoline-7-sulfonamide,
6-(dimethylamino)-N-(3,4-dimethylphenyl)-2-oxo-1,2,3,4-tetrahydroquinoline-7-sulfonamide,
6-chloro-N-(3,4-dimethylphenyl)-3-oxo-3,4-dihydro-2H-benzo[b][1,4]oxazine-7-sulfonamide,
6-bromo-N-(3,4-dimethylphenyl)-3-oxo-3,4-dihydro-2H-benzo[b][1,4]oxazine-7-sulfonamide,
N-(3,4-dimethylphenyl)-6-methyl-3-oxo-3,4-dihydro-2H-benzo[b][1,4]oxazine-7-sulfonamide,
N-(3,4-dimethylphenyl)-3-oxo-6-phenyl-3,4-dihydro-2H-benzo[b][1,4]oxazine-7-sulfonamide,
N-(3,4-dimethylphenyl)-N-methyl-2-oxo-1,2,3,4-tetrahydroquinoline-6-sulfonamide,
N-(3,4-dimethylphenyl)-2-oxo-1,2,3,4-tetrahydroquinoline-6-carboxamide,
N-(3-chloro-4-methylphenyl)-2-oxo-1,2,3,4-tetrahydroquinoline-6-sulfonamide,
N-(3,4-dichlorophenyl)-2-oxo-1,2,3,4-tetrahydroquinoline-6-sulfonamide,
6-chloro-N-(5-chloro-2-methylphenyl)-2-oxo-1,2,3,4-tetrahydroquinoline-7-sulfonamide,
N-(3-cyanophenyl)-2-oxo-1,2,3,4-tetrahydroquinoline-6-sulfonamide,
1-acetyl-N-(3,4-dimethylphenyl)-2-methylindoline-5-sulfonamide,
N-(5-chloro-2-methylphenyl)-7-fluoro-2-oxo-1,2,3,4-tetrahydroquinoline-6-sulfonamide,
6-chloro-N-(3-chloro-4-methylphenyl)-2-oxo-1,2,3,4-tetrahydroquinoline-7-sulfonamide,
N-(3-chloro-2-methylphenyl)-7-fluoro-2-oxo-1,2,3,4-tetrahydroquinoline-6-sulfonamide,
N-(3-chloro-4-methylphenyl)-7-fluoro-2-oxo-1,2,3,4-tetrahydroquinoline-6-sulfonamide,
3-(2-oxo-1,2,3,4-tetrahydroquinoline-6-sulfonamido)phenylboronic acid,
N-(4-fluoro-3-methylphenyl)-2-oxo-1,2,3,4-tetrahydroquinoline-6-sulfonamide,
N-(3,4-dichlorophenyl)-7-fluoro-2-oxo-1,2,3,4-tetrahydroquinoline-6-sulfonamide.
N-(3-fluoro-4-methylphenyl)-2-oxo-1,2,3,4-tetrahydroquinoline-6-sulfonamide,
N-(4-chloro-3-methylphenyl)-7-fluoro-2-oxo-1,2,3,4-tetrahydroquinoline-6-sulfonamide,
6-chloro-N-(3,4-dimethylphenyl)-2-oxoindoline-5-sulfonamide,
N-(4-chloro-3-methylphenyl)-2-oxo-1,2,3,4-tetrahydroquinoline-6-sulfonamide,
6-chloro-N-(3-chloro-2-methylphenyl)-2-oxo-1,2,3,4-tetrahydroquinoline-7-sulfonamide,
3,3-dichloro-N-(3,4-dimethylphenyl)-2-oxoindoline-5-sulfonamide,
7-((2-(dimethylamino)ethyl)(methyl)amino)-N-(3,4-dimethylphenyl)-2-oxo-1,2,3,4-tetrahydroquinoline-6-sulfonamide,
N-(3,4-dimethylphenyl)-2-oxo-7-(pyrrolidin-1-yl)-1,2,3,4-tetrahydroquinoline-6-sulfonamide,
7-(3-(dimethylamino)pyrrolidin-1-yl)-N-(3,4-dimethylphenyl)-2-oxo-1,2,3,4-tetrahydroquinoline-6-sulfonamide,
N-(3,4-dimethylphenyl)-7-(2-hydroxy-2-methylpropylamino)-2-oxo-1,2,3,4-tetrahydroquinoline-6-sulfonamide,
N-(3,4-dimethylphenyl)-7-(isopropylamino)-2-oxo-1,2,3,4-tetrahydroquinoline-6-sulfonamide,
7-(diethylamino)-N-(3,4-dimethylphenyl)-2-oxo-1,2,3,4-tetrahydroquinoline-6-sulfonamide, N-(3,4-dimethylphenyl)-7-(1-hydroxypropan-2-ylamino)-2-oxo-1,2,3,4-tetrahydroquinoline-6-sulfonamide,
(S)—N-(3,4-dimethylphenyl)-7-(1-hydroxypropan-2-ylamino)-2-oxo-1,2,3,4-tetrahydroquinoline-6-sulfonamide,
(R)—N-(3,4-dimethylphenyl)-7-(1-hydroxypropan-2-ylamino)-2-oxo-1,2,3,4-tetrahydroquinoline-6-sulfonamide,
N-(3,4-dimethylphenyl)-7-(2-hydroxyethylamino)-2-oxo-1,2,3,4-tetrahydroquinoline-6-sulfonamide,
(S)—N-(3-chloro-4-methylphenyl)-7-(1-hydroxypropan-2-ylamino)-2-oxo-1,2,3,4-tetrahydroquinoline-6-sulfonamide,
(S)—N-(4-fluoro-3-methylphenyl)-7-(1-hydroxypropan-2-ylamino)-2-oxo-1,2,3,4-tetrahydroquinoline-6-sulfonamide, and
(S)—N-(3-chloro-4-fluorophenyl)-7-(1-hydroxypropan-2-ylamino)-2-oxo-1,2,3,4-tetrahydroquinoline-6-sulfonamide.

In one embodiment of the invention, the compounds exclude a compound of formula (II) wherein $R^2$ is a methyl in the para position relative to the NR-L moiety, $R^3$ is a methyl in a meta position relative to the NR-L moiety, $X^3$ is CH, k is zero, R is H, L is $SO_2$, $R^1$ is H, $X^1$ is $NR^6$, $R^6$ is H, $X^2$ is $CR^7R^8$, $R^7$ and $R^8$ are each H, n is 1, m is zero, and the methylene adjacent to $X^1$ is replaced with a carbonyl.

Certain molecule modulators of human PK activity are known. Fructose-1,6-bis phosphate (FBP) (compound 1) is required to allosterically activate human PKM2, PKL, and PKR. NCGC00185916 (compound 2), NCGC00186527 (compound 3), and others listed in International Patent Application No. PCT/US09/60237 (incorporated herein by reference) also activate human PKM2.

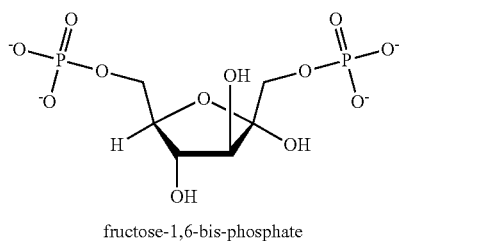

fructose-1,6-bis-phosphate (1)

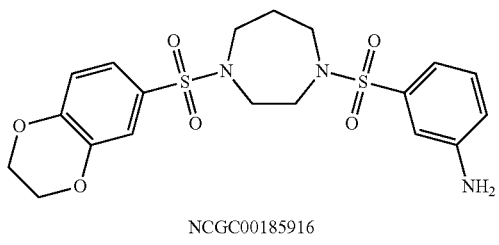

NCGC00185916 (2)

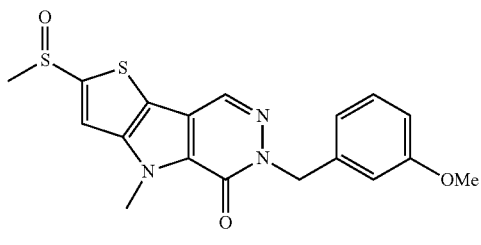

NCGC00186527 (3)

Referring now to terminology used generically herein, the term "alkyl" means a straight-chain or branched alkyl substituent containing from, for example, 1 to about 6 carbon atoms, preferably from 1 to about 4 carbon atoms, more preferably from 1 to 2 carbon atoms. Examples of such substituents include methyl, ethyl, propyl, isopropyl, n-butyl, sec-butyl, isobutyl, tert-butyl, pentyl, isoamyl, hexyl, and the like. The term "alkoxyl" means any alkyl substituent attached as a substituent via an oxygen atom.

The term "alkenyl," as used herein, means a linear alkenyl substituent containing at least one carbon-carbon double bond and from, for example, about 2 to about 6 carbon atoms (branched alkenyls are about 3 to about 6 carbons atoms), preferably from about 2 to about 5 carbon atoms (branched alkenyls are preferably from about 3 to about 5 carbon atoms), more preferably from about 3 to about 4 carbon atoms. Examples of such substituents include propenyl, isopropenyl, n-butenyl, sec-butenyl, isobutenyl, tert-butenyl, pentenyl, isopentenyl, hexenyl, and the like. "Alkylenedioxy" means a —O—$(CH_2)_q$—O— group, where q is from 1 to about 6, preferably from 1 to about 4, more preferably from 1 to 2.

The term "alkynyl," as used herein, means a linear alkynyl substituent containing at least one carbon-carbon triple bond and from, for example, 2 to about 6 carbon atoms (branched alkynyls are about 3 to about 6 carbons atoms), preferably from 2 to about 5 carbon atoms (branched alkynyls are preferably from about 3 to about 5 carbon atoms), more preferably from about 3 to about 4 carbon atoms. Examples of such substituents include propynyl, isopropynyl, n-butynyl, sec-butynyl, isobutynyl, tert-butynyl, pentynyl, isopentynyl, hexynyl, and the like.

The term "cyclyl" as used herein encompasses cycloalkyl and cycloalkenyl. "Cycloalkyl" as used herein, means a cyclic alkyl substituent containing from, for example, about 3 to about 8 carbon atoms, preferably from about 4 to about 7 carbon atoms, and more preferably from about 4 to about 6 carbon atoms. Examples of such substituents include cyclopropyl, cyclobutyl, cyclopentyl, cyclohexyl, cycloheptyl, cyclooctyl, and the like. The term "cycloalkenyl," as used herein, means the same as the term "cycloalkyl," however one or more double bonds are present. Examples include cyclopentenyl and cyclohexenyl. The cyclic alkyl groups may be unsubstituted or further substituted. Examples of substitutions include halogens, alkyoxy groups, and alkyl groups such as methyl groups, ethyl groups, and the like. "Cyclyl" also encompasses cycloalkyl and cycloalkenyl in which a heteroatom is exocyclic. The heteroatom, for example, may be N, O, or S. For example, a methylene group of the cyclyl can be replaced with a carbonyl. A cyclyl group may be fused to another ring, including another cyclyl, heterocyclyl, aryl, or heteroaryl. A fused bicyclic ring is any ring of cyclyl, heterocyclyl, aryl, or heteroaryl fused with another cyclyl, heterocyclyl, aryl, or heteroaryl.

The term "heteroaryl," as used herein, refers to a monocyclic or bicyclic 5- or 6-membered aromatic ring system containing one or more heteroatoms selected from the group consisting of O, N, S, and combinations thereof. Examples of suitable monocyclic heteroaryl groups include but are not limited to furanyl, thiopheneyl, pyrrolyl, pyrazolyl, imidazolyl, 1,2,3-triazolyl, 1,2,4-triazolyl, isoxazolyl, oxazolyl, isothiazolyl, thiazolyl, pyridinyl, pyrimidinyl, pyrazinyl, and triazinyl. The heteroaryl group can be attached at any available position on the heteroaryl group. For example, a thiopheneyl group can be attached at the 2-position or the 3-position of the thiopheneyl group. A pyridyl group can be attached at the 2-, 3-, or 4-position of the pyridyl group. Suitable bicyclic heterocycloaryl groups include monocyclic heterocycloaryl rings fused to a $C_6$-$C_{10}$ aryl or heteroaryl ring. Non-limiting examples of bicyclic heterocycloaryl groups include benzofuran, benzothiophene, quinoline, and isoquinoline. The heteroaryl group is optionally substituted with 1, 2, 3, 4, or 5 substituents as recited herein, wherein the optional substituent can be present at any open position on the heteroaryl group.

The term "heteroaryl oxide," as used herein, refers to an oxidized heteroaryl group as that term is defined herein, wherein one or more of the heteroatoms comprising the heteroaryl group is oxidized. Non-limiting examples of heteroaryl oxide groups include pyridine N-oxide, pyrimidine N-oxide, and pyrazine N-oxide.

The term "heterocyclyl" refers to a cyclic group, which may be aromatic or non-aromatic, or saturated or unsaturated, having one or more heteroatoms such as O, N, or S. Examples of heterocyclyl groups include pyridyl, piperidinyl, piperazinyl, pyrazinyl, pyrolyl, pyranyl, tetrahydropyranyl, tetrahydrothiopyranyl, pyrrolidinyl, furanyl, tetrahydrofuranyl, thiophenyl, tetrahydrothiophenyl, purinyl, pyrimidinyl, thiazolyl, thiazolidinyl, thiazolinyl, oxazolyl, triazolyl, tetrazolyl, tetrazinyl, benzoxazolyl, morpholinyl, thiophorpholinyl, quinolinyl, and isoquinolinyl. A heterocyclyl group may be fused to another ring, including a cyclyl, aryl, heteroaryl, or another heterocyclyl.

The term "halo" or "halogen," as used herein, means a substituent selected from Group VIIA, such as, for example, fluorine, bromine, chlorine, and iodine.

The term "aryl" refers to an unsubstituted or substituted aromatic carbocyclic substituent, as commonly understood in the art, and the term "$C_6$-$C_{10}$ aryl" includes phenyl and naphthenyl. It is understood that the term aryl applies to cyclic substituents that are planar and comprise $4n+2\pi$ electrons, according to Hückel's Rule. An aryl group may be fused to another ring, including a cyclyl, heteroaryl, heterocyclyl, or another aryl.

A $CH_2$—$CH_2$ moiety is any ethylene moiety wherein there is a carbon-carbon single bond. A CH=CH moiety is any vinyl moiety that contains a carbon-carbon double bond. A NH—$CH_2$ moiety contains a nitrogen-carbon single bond, and a N=CH contains a nitrogen-carbon double bond. A CH:CH moiety contains a carbon-carbon bond intermediate between a single and a double bond, such as in an aromatic system, for example in the carbon-carbon bonds in benzene or the nitrogen-carbon bond in pyridine.

The present invention also provides a pharmaceutical composition comprising a compound or salt of any of the embodiments described above and a pharmaceutically acceptable carrier.

The phrase "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, nonaqueous media such as ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, p. 1445, and *Journal of Pharmaceutical Science*, 66, 2-19 (1977).

Suitable bases include inorganic bases such as alkali and alkaline earth metal bases, e.g., those containing metallic cations such as sodium, potassium, magnesium, calcium and the like. Non-limiting examples of suitable bases include sodium hydroxide, potassium hydroxide, sodium carbonate, and potassium carbonate. Suitable acids include inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, maleic acid, tartaric acid, fatty acids, long chain fatty acids, and the like. Preferred pharmaceutically acceptable salts of inventive compounds having an acidic moiety include sodium and potassium salts. Preferred pharmaceutically acceptable salts of inventive compounds having a basic moiety (e.g., a pyridyl group) include hydrochloride and hydrobromide salts. The compounds of the present invention containing an acidic or basic moiety are useful in the form of the free base or acid or in the form of a pharmaceutically acceptable salt thereof.

It should be recognized that the particular counterion forming a part of any salt of this invention is usually not of a critical nature, so long as the salt as a whole is pharmacologically acceptable and as long as the counterion does not contribute undesired qualities to the salt as a whole.

It is further understood that the above compounds and salts may form solvates, or exist in a substantially uncomplexed form, such as the anhydrous form. As used herein; the term "solvate" refers to a molecular complex wherein the solvent molecule, such as the crystallizing solvent, is incorporated into the crystal lattice. When the solvent incorporated in the solvate is water, the molecular complex is called a hydrate. Pharmaceutically acceptable solvates include hydrates, alcoholates such as methanolates and ethanolates, acetonitrilates and the like. These compounds can also exist in polymorphic forms.

The invention contemplates embodiments in which a compound having a chiral center is a substantially pure enantiomer thereof, a racemic mixture thereof, or a mixture containing any proportion of the two enantiomers thereof. The invention also contemplates all stereoisomers and diastereoisomers of the compounds described herein.

The present invention is further directed to a pharmaceutical composition comprising a pharmaceutically acceptable carrier and at least one compound or salt described herein.

It is preferred that the pharmaceutically acceptable carrier be one that is chemically inert to the active compounds and one that has no detrimental side effects or toxicity under the conditions of use.

The choice of carrier will be determined in part by the particular compound of the present invention chosen, as well as by the particular method used to administer the composition. Accordingly, there is a wide variety of suitable formulations of the pharmaceutical composition of the present invention. The following formulations for oral, aerosol, parenteral, subcutaneous, intra-arterial, intravenous, intramuscular, intraperitoneal, intrathecal, rectal, and vaginal administration are merely exemplary and are in no way limiting.

The pharmaceutical composition can be administered parenterally, e.g., intravenously, subcutaneously, intradermally, or intramuscularly. Thus, the invention provides compositions for parenteral administration that comprise a solution of the inventive compound or salt dissolved or suspended in an acceptable carrier suitable for parenteral administration, including aqueous and non-aqueous isotonic sterile injection solutions.

Overall, the requirements for effective pharmaceutical carriers for parenteral compositions are well known to those of ordinary skill in the art. See, e.g., Banker and Chalmers, eds., *Pharmaceutics and Pharmacy Practice*, J. B. Lippincott Company, Philadelphia, pp. 238-250 (1982), and Toissel, *ASHP Handbook on Injectable Drugs*, 4th ed., pp. 622-630 (1986). Such solutions can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound or salt of the present invention may be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-beta-aminopropionates, and 2-alkyl-imidazoline quaternary ammonium salts, and (e) mixtures thereof.

The parenteral formulations can contain preservatives and buffers. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Topical formulations, including those that are useful for transdermal drug release, are well-known to those of skill in the art and are suitable in the context of the invention for application to skin.

Formulations suitable for oral administration can consist of (a) liquid solutions, such as a therapeutically effective amount of the inventive compound dissolved in diluents, such as water, saline, or orange juice, (b) capsules, sachets, tablets, lozenges, and troches, each containing a predetermined amount of the active ingredient, as solids or granules, (c) powders, (d) suspensions in an appropriate liquid, and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, *acacia*, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and *acacia* or tragacanth, as well as pastilles comprising the active ingredient in an inert base, such as gelatin and glycerin, or sucrose and *acacia*, emulsions, gels, and the like containing, in addition to the active ingredient, such excipients as are known in the art.

The compound or salt of the present invention, alone or in combination with other suitable components, can be made into aerosol formulations to be administered via inhalation. The compounds are preferably supplied in finely divided form along with a surfactant and propellant. Typical percentages of active compound are 0.01%-20% by weight, preferably 1%-10%. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25%-5%. The balance of the composition is ordinarily propellant. A carrier can also be included as desired, e.g., lecithin for intranasal delivery. These aerosol formulations can be placed into acceptable pressurized propellants, such as dichlorodifluoromethane, propane, nitrogen, and the like. They also may be formulated as pharmaceuticals for non-pressured preparations, such as in a nebulizer or an atomizer. Such spray formulations may be used to spray mucosa.

Additionally, the compound or salt of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

It will be appreciated by one of ordinary skill in the art that, in addition to the aforedescribed pharmaceutical compositions, the compound or salt of the present invention may be formulated as inclusion complexes, such as cyclodextrin inclusion complexes, or liposomes. Liposomes serve to target the compounds to a particular tissue, such as lymphoid tissue or cancerous hepatic cells. Liposomes can also be used to increase the half-life of the inventive compound. Liposomes useful in the present invention include emulsions, foams, micelles, insoluble monolayers, liquid crystals, phospholipid dispersions, lamellar layers and the like. In these preparations, the active agent to be delivered is incorporated as part of a liposome, alone or in conjunction with a suitable chemotherapeutic agent. Thus, liposomes filled with a desired inventive compound or salt thereof, can be directed to the site of a specific tissue type, hepatic cells, for example, where the liposomes then deliver the selected compositions. Liposomes for use in the invention are formed from standard vesicle-forming lipids, which generally include neutral and negatively charged phospholipids and a sterol, such as cholesterol. The selection of lipids is generally guided by consideration of, for example, liposome size and stability of the liposomes in the blood stream. A variety of methods are available for preparing liposomes, as described in, for example, Szoka et al., Ann. Rev. Biophys. Bioeng., 9, 467 (1980), and U.S. Pat. Nos. 4,235,871, 4,501,728, 4,837,028; and 5,019,369. For targeting to the cells of a particular tissue type, a ligand to be incorporated into the liposome can include, for example, antibodies or fragments thereof specific for cell surface determinants of the targeted tissue type. A liposome suspension containing a compound or salt of the present invention may be administered intravenously, locally, topically, etc. in a dose that varies according to the mode of administration, the agent being delivered, and the stage of disease being treated.

Suitable doses and dosage regimens can be determined by conventional range-finding techniques known to those of ordinary skill in the art. Generally, treatment is initiated with smaller dosages that are less than the optimum dose of the compound. Thereafter, the dosage is increased by small increments until the optimum effect under the circumstances is reached. The present inventive method typically will involve the administration of about 0.001 to about 300 mg of one or more of the compounds described above per kg body weight of the individual. The administration can involve about 0.001 mg, about 0.01 mg, about 0.1 mg, about 1 mg, about 5 mg, about 10 mg, about 20 mg, about 50 mg, about 100 mg, about 200 mg, or about 300 mg or more of one or more of the compounds described above per kg body weight of the individual. Alternatively, or in addition, the administration can involve about 300 mg, about 200 mg, about 100 mg, about 50 mg, about 20 mg, about 10 mg, about 5 mg, about 1 mg, about 0.1 mg, about 0.01 mg, or about 0.001 mg or less of one or more of the compounds described above per kg body weight of the individual. Thus, the administration can be bounded by any two of the aforementioned endpoints. For example, the administration can be about 0.001 mg to about 200 mg, about 0.001 mg to about 1 mg, about 0.01 mg to about 50 mg, about 0.1 mg to about 20 mg, about 1 mg to about 10 mg, about 1 mg to about 20 mg, about 10 mg to about 50 mg, or any other combination of endpoints, of one or more of the compounds described above per kg body weight of the individual.

The present invention further provides a method of treating a disease responsive to activation of human PK-M2 comprising administering to a patient in need thereof a therapeutically effective amount of any of the compounds described herein or a pharmaceutically acceptable salt thereof.

The invention further provides any of the compounds described herein or a pharmaceutically acceptable salt thereof for use in treating a disease responsive to activation of human PK-M2.

The invention further provides the use of a compound or a pharmaceutically acceptable salt thereof in the manufacture of a medicament for treating a disease responsive to activation of human PK-M2 of a patient, wherein the compound is any of the compounds described herein or a pharmaceutically acceptable salt thereof The disease responsive to activation of PK-M2 can be caused by or associated with, e.g., the function PKM2. These diseases may include, e.g., cancer, obesity, diabetes, atherosclerosis, restenosis, autoimmune diseases, and proliferation-dependent diseases.

Cancers include, without limitation, leukemias (e.g., acute leukemia, acute lymphocytic leukemia, acute myelocytic (myeloid) leukemia, acute myeloblastic leukemia, acute promyelocytic leukemia, acute myelomonocytic leukemia, acute monocytic leukemia, acute erythroleukemia, chronic leukemia, chronic myelocytic (myeloid) leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, (malignant) mesothelioma, Ewing's tumor, leiomyosarcoma, rhabdomyosarcoma (including alveolar), colon carcinoma (colon cancer), pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct/intrahepatic bile duct carcinoma, choriocarcinoma, seminoma, embryonal carcinoma, Wilm's tumor, cervical cancer, uterine cancer, testicular cancer, lung carcinoma (lung cancer), small cell lung carcinoma, bladder carcinoma (urinary bladder cancer), epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma). The cancers may include bone cancer, brain cancer, cancer of the anus, anal canal, or anorectum, cancer of the eye, cancer of the joints, cancer of the neck, gallbladder, or pleura, cancer of the nose, nasal cavity, or middle ear, cancer of the oral cavity, cancer of the vulva, esophageal cancer, gastrointestinal carcinoid tumor, hypopharynx cancer, kidney cancer, larynx cancer, liver cancer, nasopharynx cancer, non-small cell lung cancer, peritoneum, omentum, and mesentery cancer, pharynx cancer, rectal cancer, renal cancer, small intestine cancer, soft tissue cancer, stomach cancer, thyroid cancer, and ureter cancer.

Other diseases include diabetes and obesity. Adipose tissue expresses PKM2. Additionally, activators of PKM2, described herein, may be useful in the treatment of type II diabetes, as the activation of PKM2 may allow for decreased lipid production and increased oxidative phosphorylation in adipose tissue. This effect should decrease adiposity, which is known to contribute to type 2 diabetes.

Additionally diseases include autoimmune diseases and proliferative diseases. Activators of PKM2, described herein, may be used to treat, e.g., autoimmune diseases or proliferative diseases. Autoimmune disorders include, e.g., type I diabetes, Crohn's disease, multiple sclerosis, arthritis, rheumatoid arthritis, systemic lupus erythematosus, autoimmune (Hashimoto's) thyroiditis, autoimmune liver diseases (e.g., hepatitis and primary biliary cirrhosis), hyperthyroidism (e.g., Graves' disease and thyrotoxicosis), insulin-resistant diabetes, autoimmune adrenal insufficiency (e.g., Addison's disease), autoimmune oophoritis, autoimmune orchitis, autoimmune hemolytic anemia, paroxysmal cold hemoglobinuria, Behcet's disease, autoimmune thrombocytopenia, autoimmune neutropenia, pernicious anemia, pure red cell anemia, autoimmune coagulopathies, myasthenia gravis, experimental allergic encephalomyelitis, autoimmune polyneuritis, *pemphigus* and other bullous diseases, rheumatic carditis, Goodpasture's syndrome, postcardiotomy syndrome, Sjogren's syndrome, polymyositis, dermatomyositis, and *scleroderma*. Autoimmune disorders are described in U.S. Pat. Nos. 5,891,435 and 6,773,705, hereby incorporated by reference.

Proliferative diseases include, e.g., cancer (e.g., benign and malignant), benign prostatic hyperplasia, psoriasis, abnormal keratinization, lymphoproliferative disorders (e.g., a disorder in which there is abnormal proliferation of cells of the lymphatic system), chronic rheumatoid arthritis, arteriosclerosis, restenosis, and diabetic retinopathy. Proliferative diseases are described in U.S. Pat. Nos. 5,639,600 and 7,087,648, hereby incorporated by reference.

The terms "treat" and "prevent," as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention in a mammal. Furthermore, the treatment or prevention provided by the inventive method can include treatment or prevention of one or more conditions or symptoms of the diseases described herein being treated or prevented. Also, for purposes herein, "prevention" can encompass delaying the onset of the disease, or a symptom or condition thereof.

The invention further provides a use of a compound or salt of the invention in the manufacture of a medicament for treating disease responsive to activation of PK-M2. The medicament typically is a pharmaceutical composition as described herein.

One skilled in the art will appreciate that suitable methods of utilizing a compound and administering it to a human for the treatment of disease states, in particular, diseases responsive to activation of PK-M2, which would be useful in the method of the present invention, are available. Although more than one route can be used to administer a particular compound, a particular route can provide a more immediate and more effective reaction than another route. Accordingly, the described methods are merely exemplary and are in no way limiting.

The dose administered to a human in accordance with the present invention should be sufficient to effect the desired response. Such responses include reversal or prevention of the bad effects of the disease responsive to activation of PK-M2 for which treatment is desired or to elicit the desired benefit. One skilled in the art will recognize that dosage will depend upon a variety of factors, including the age, condition, and body weight of the human, as well as the source, particular type of the cancer, and extent of cancer in the human. The size of the dose will also be determined by the route, timing and frequency of administration as well as the existence, nature, and extent of any adverse side-effects that might accompany the administration of a particular compound and the desired physiological effect. It will be appreciated by one of skill in the art that various conditions or disease states may require prolonged treatment involving multiple administrations.

The compounds of the invention can be prepared as follows. For example, the synthetic elaboration of substituted 2-oxo-N-aryl-1,2,3,4-tetrahydroquinoline-6-sulfonamides can begin with a standard coupling between commercially available sulfonyl chlorides and substituted anilines, according to Scheme I.

Scheme 1

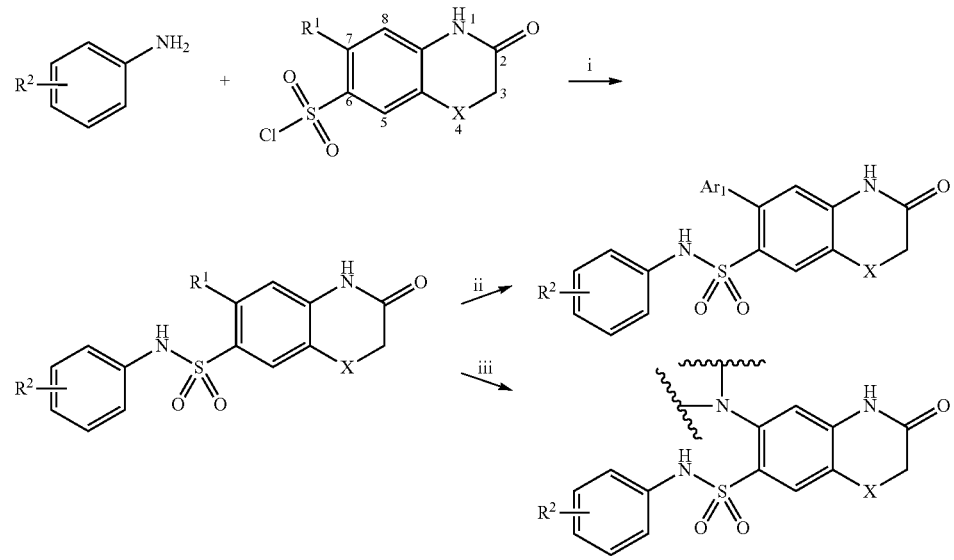

Conditions and reagents: (i) Hunig's base, DMF, rt, 1 h; (ii) Ar₁—B(OH)₂, tetrakis (3 mol %), Na₂CO₃, 1,2,-DME/H₂O, μW, 120° C., 20 min; (iii) R'''N, MeCN, μW, 180° C., 1 h.

The following examples further illustrate the invention but, of course, should not be construed as in any way limiting its scope.

EXAMPLE 1

This example illustrates methods used in preparing exemplary compounds of the invention.

General Methods Used for all Exemplary Compounds.

All air or moisture sensitive reactions were performed under positive pressure of nitrogen with oven-dried glassware.

Anhydrous solvents such as tetrahydrofuran (THF), toluene, dichloromethane, N,N-dimethylformamide (DMF), acetonitrile, methanol and triethylamine were obtained from Sigma-Aldrich (St. Louis, Mo., USA). Preparative purification was performed on a Waters® (Milford, Mass., USA) semi-preparative HPLC. The column used was a Phenomenex (Torrance, Calif., USA) Luna C18 (5 micron, 30×75 mm) at a flow rate of 45 mL/min. The mobile phase consisted of acetonitrile and water (each containing 0.1% trifluoroacetic acid). A gradient of 10% to 50% acetonitrile over 8 minutes was used during the purification. Fraction collection was triggered by UV detection (220 nM). Analytical analysis was performed on an Agilent LC/MS (Agilent Technologies, Santa Clara, Calif., USA).

Method 1: A 7 minute gradient of 4% to 100% Acetonitrile (containing 0.025% trifluoroacetic acid) in water (containing 0.05% trifluoroacetic acid) was used with an 8 minute run time at a flow rate of 1 mL/min. A Phenomenex Luna C18 column (3 micron, 3×75 mm) was used at a temperature of 50° C.

Method 2: A 3 minute gradient of 4% to 100% Acetonitrile (containing 0.025% trifluoroacetic acid) in water (containing 0.05% trifluoroacetic acid) was used with a 4.5 minute run time at a flow rate of 1 mL/min. A Phenomenex Gemini Phenyl column (3 micron, 3×100 mm) was used at a temperature of 50° C.

Purity determination was performed using an Agilent Diode Array Detector. Mass determination was performed using an Agilent 6130 mass spectrometer with electrospray ionization in the positive mode. $^1$H NMR spectra were recorded on Varian (Palo Alto, Calif., USA) 400 MHz spectrometers. Chemical Shifts are reported in ppm with tetramethylsilane (TMS) as internal standard (0 ppm) for CDCl$_3$ solutions or undeuterated solvent (DMSO-H6 at 2.49 ppm) for DMSO-d6 solutions. All of the analogues for assay have purity greater than 95% based on both analytical methods. High resolution mass spectrometry was recorded on Agilent 6210 Time-of-Flight LC/MS system. Confirmation of molecular formula was accomplished using electrospray ionization in the positive mode with the Agilent Masshunter software (version B.02).

General Procedure of or Synthesis of Compounds 4-31, 35, 37-39, 41, and 43-60

The methods of synthesizing compound 4 were generally followed for all compounds 4-31, 35, 37-39, 41, and 43-60.

Compound 4. N-(3,4-dimethylphenyl)-2-oxo-1,2,3,4-tetrahydroquinoline-6-sulfonamide

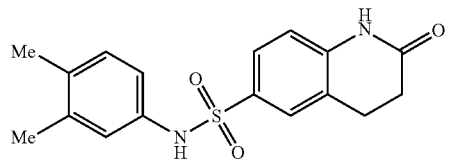 [SMILES: Cc1ccc(NS(=O)(=O)c2ccc3c(c2)CCC(=O)N3)cc1C]

2-oxo-1,2,3,4-tetrahydroquinoline-6-sulfonyl chloride (0.2 g, 0.814 mmol) was dissolved in DMF (2 ml) and 3,4-dimethylaniline (0.118 g, 0.977 mmol) was added followed by the dropwise addition of DIPEA (0.213 ml, 1.221 mmol). The reaction was stirred at RT for 1 h then purified by directly injecting to a Waters® reverse phase purification system.

$^1$H NMR (400 MHz, DMSO-d6) δ ppm: 10.40 (s, 1H), 9.91 (br. s., 1H), 7.56 (s, 1H), 7.51 (dd, J=8.41, 1.96 Hz, 1H), 6.95 (d, J=8.22 Hz, 1H), 6.90 (d, J=8.22 Hz, 1H), 6.86 (s, 1H), 6.81 (dd, J=8.02, 1.96 Hz, 1H), 2.90 (t, J=7.53 Hz, 2H), 2.46 (t, J=7.63 Hz, 2H), 2.10 (s, 3H), 2.08 (s, 3H). LC/MS: Method 1, retention time: 5.744 min; HRMS: m/z (M+)=454.0872 (Calculated for $C_{19}H_{22}N_2O_7S_2$=454.0868).

Compound 5.
N-(3,4-dimethylphenyl)-2-oxoindoline-5-sulfonamide

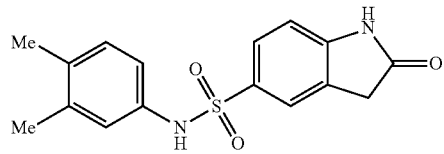 [SMILES: Cc1ccc(NS(=O)(=O)c2ccc3c(c2)CC(=O)N3)cc1C]

2-oxoindoline-5-sulfonyl chloride (0.189 g, 0.814 mmol) was dissolved in DMF (2 ml) and 3,4-dimethylaniline (0.118 g, 0.977 mmol) was added followed by the dropwise addition of DIPEA (0.213 ml, 1.221 mmol). The reaction was stirred at RT for 1 h then purified by directly injecting to a Waters® reverse phase purification system.

$^1$H NMR (400 MHz, DMSO-d6) δ ppm: 10.70 (s, 1H), 9.87 (s, 1H), 7.44-7.62 (m, 2H), 6.67-6.98 (m, 4H), 3.50 (s, 2H), 2.05 (m, 6H). LC/MS: Method 1, retention time: 4.833 min; HRMS: m/z (M+)=316.0878 (Calculated for $C_{16}H_{16}N_2O_3S$=316.0882).

Compound 6. N-(3,4-dimethylphenyl)-2-oxo-2,3,4,5-tetrahydro-1H-benzo[b]azepine-7-sulfonamide

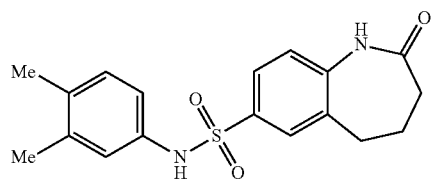 [SMILES: Cc1ccc(NS(=O)(=O)c2ccc3c(c2)CCCC(=O)N3)cc1C]

$^1$H NMR (400 MHz, DMSO-d6) δ ppm: 9.89 (br. s., 1H), 9.77 (br. s., 1H), 7.38-7.67 (m, 2H), 7.00 (d, J=8.2 Hz, 1H), 6.93 (d, J=8.0 Hz, 1H), 6.61-6.86 (m, 2H), 2.57-2.72 (m, 2H), 1.93-2.22 (m, 10H). LC/MS: Method 1, retention time: 5.081 min; HRMS: m/z (M+)=344.1195 (Calculated for $C_{18}H_{20}N_2O_3S$=344.1195).

Compound 7. N-(3,4-dimethylphenyl)-3-oxo-3,4-dihydro-2H-benzo[b][1,4]oxazine-6-sulfonamide

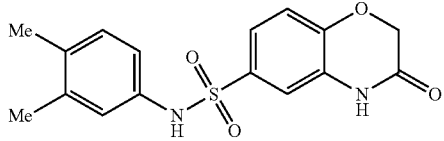 [SMILES: Cc1ccc(NS(=O)(=O)c2ccc3c(c2)NC(=O)CO3)cc1C]

$^1$H NMR (400 MHz, DMSO-$d_6$) δ ppm: 10.90 (br. s., 1H), 9.97 (br. s., 1H), 7.17-7.32 (m, 2H), 7.01 (d, J=8.8 Hz, 1H), 6.94 (d, J=8.2 Hz, 1H), 6.83 (d, J=1.8 Hz, 1H), 6.76 (dd, J=8.1, 2.1 Hz, 1H), 4.62 (s, 2H), 2.07 (m, 6H). LC/MS: Method 1, retention time: 5.133 min; HRMS: m/z (M+)=332.0823 (Calculated for $C_{16}H_{16}N_2O_4S$=332.0831).

Compound 8. N-(3,4-dimethylphenyl)-4-methyl-3-oxo-3,4-dihydro-2H-benzo[b][1,4]oxazine-6-sulfonamide

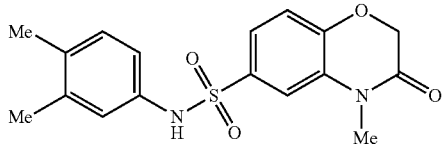 [SMILES: Cc1ccc(NS(=O)(=O)c2ccc3c(c2)N(C)C(=O)CO3)cc1C]

$^1$H NMR (400 MHz, DMSO-$d_6$) δ ppm: 9.93 (s, 1H), 7.25-7.43 (m, 2H), 7.06 (d, J=8.4 Hz, 1H), 6.94 (d, J=8.0 Hz, 1H), 6.86 (s, 1H), 6.79 (dd, J=8.0, 2.2 Hz, 1H), 4.70 (s, 2H), 3.19 (s, 3H), 2.07 (m, 6H). LC/MS: Method 1, retention time: 5.519 min; HRMS: m/z (M+)=346.0989 (Calculated for $C_{17}H_{18}N_2O_4S$=346.0987).

Compound 9. N-(3,4-dimethylphenyl)-2-oxo-2,3-dihydro-1H-benzo[d]imidazole-5-sulfonamide

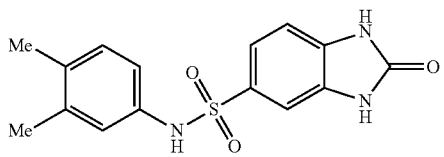 [SMILES: Cc1ccc(NS(=O)(=O)c2ccc3[nH]c(=O)[nH]c3c2)cc1C]

$^1$H NMR (400 MHz, DMSO-$d_6$) δ ppm: 11.02 (br. s., 1H), 10.89 (br. s., 1H), 9.83 (br. s., 1H), 7.31 (dd, J=8.2, 1.6 Hz, 1H), 7.21 (d, J=1.6 Hz, 1H), 6.96 (d, J=8.2 Hz, 1H), 6.90 (d, J=8.2 Hz, 1H), 6.81 (s, 1H), 6.75 (dd, J=8.0, 2.0 Hz, 1H), 2.05 (m, 6H). LC/MS: Method 1, retention time: 4.535 min; HRMS: m/z (M+)=317.0837 (Calculated for $C_{15}H_{15}N_3O_3S$=317.0834).

Compound 10. N-(3,4-dimethylphenyl)-1,3-dimethyl-2-oxo-2,3-dihydro-1H-benzo[d]imidazole-5-sulfonamide

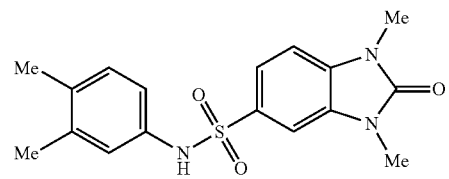 [SMILES: Cc1ccc(NS(=O)(=O)c2ccc3c(c2)n(C)c(=O)n3C)cc1C]

$^1$H NMR (400 MHz, DMSO-$d_6$) δ ppm: 9.87 (s, 1H), 7.33-7.52 (m, 2H), 7.21 (d, J=8.0 Hz, 1H), 6.90 (d, J=8.0 Hz, 1H), 6.85 (d, J=1.8 Hz, 1H), 6.77 (dd, J=8.1, 2.1 Hz, 1H), 3.23-3.37 (s, 6H), 2.05 (m, 6H).). LC/MS: Method 1, retention time: 5.179 min; HRMS: m/z (M+)=345.1152 (Calculated for $C_{17}H_{19}N_3OS$=345.1147).

Compound 11. 1-acetyl-N-(3,4-dimethylphenyl)indoline-5-sulfonamide $^1$H NMR (400 MHz, DMSO-$d_6$) δ ppm: 9.86 (s, 1H), 8.02 (d, J=8.8 Hz, 1H), 7.41-7.56 (nm, 2H), 6.91 (d, J=8.2 Hz, 1H), 6.82 (s, 1H), 6.75 (dd, J=7.9, 1.9 Hz, 1H), 4.08 (t, J=8.5 Hz, 2H), 3.11 (t, J=8.4 Hz, 2H), 2.12 (s, 3H), 2.05 (m, 6H). LC/MS: Method 1, retention time: 5.338 min; HRMS: m/z (M+)=344.1196 (Calculated for $C_{18}H_{20}N_2O_3S$=344.1195).

Compound 12. N-(3,4-dimethylphenyl)-1-methyl-1H-indole-5-sulfonamide $^1$H NMR (400 MHz, DMSO-$d_6$) δ ppm: 9.82 (s, 1H), 7.96 (d, J=1.2 Hz, 1H), 7.40-7.55 (m, 3H), 6.80-6.91 (m, 2H), 6.72-6.80 (m, 1H), 6.55 (d, J=2.9 Hz, 1H), 3.76 (s, 3H), 2.01 (m, 6H). Method 1, retention time: 5.895 min; HRMS: m/z (M+)=314.1095 (Calculated for $C_{17}H_{18}N_2O_2S$=314.1089).

Compound 13. N-(3-chlorophenyl)-2-oxo-1,2,3,4-tetrahydroquinoline-6-sulfonamide

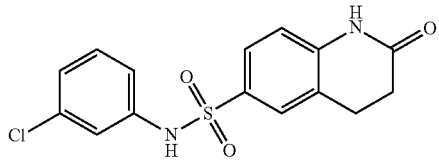 [SMILES: O=C1CCc2cc(S(=O)(=O)Nc3cccc(Cl)c3)ccc2N1]

$^1$H NMR (400 MHz, DMSO-d$_6$) δ ppm: 10.41 (s, 2H), 7.46-7.63 (m, 2H), 7.22 (t, J=8.1 Hz, 1H), 6.98-7.13 (m, 3H), 6.90 (d, J=8.4 Hz, 1H), 2.89 (t, J=7.6 Hz, 2H), 2.35-2.48 (m, 2H). LC/MS: Method 1, retention time: 4.933 min; HRMS: m/z (M+)=336.0333 (Calculated for C$_{15}$H$_{13}$ClN$_2$O$_3$S=336.0335).

Compound 14. 2-oxo-N-m-tolyl-1,2,3,4-tetrahydroquinoline-6-sulfonamide

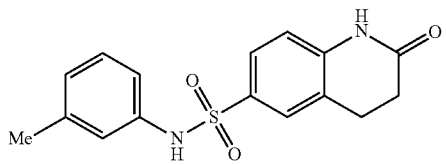 [SMILES: Cc1cccc(NS(=O)(=O)c2ccc3c(c2)CCC(=O)N3)c1]

$^1$H NMR (400 MHz, DMSO-d$_6$) δ ppm: 10.38 (s, 1H), 10.03 (s, 1H), 7.41-7.61 (m, 2H), 7.06 (t, J=7.8 Hz, 1H), 6.82-6.93 (m, 3H), 6.78 (d, J=7.2 Hz, 1H), 2.87 (t, J=7.6 Hz, 2H) 2.39-2.45 (t, J=7.8 Hz, 2H), 2.16 (s, 3H). LC/MS: Method 1, retention time: 4.741 min; HRMS: m/z (M+)=316.0886 (Calculated for C$_{16}$H$_{16}$N$_2$O$_3$S=316.0882).

Compound 15. N-(3-methoxyphenyl)-2-oxo-1,2,3,4-tetrahydroquinoline-6-sulfonamide

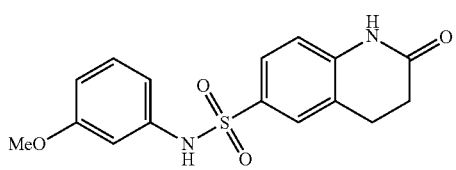 [SMILES: COc1cccc(NS(=O)(=O)c2ccc3c(c2)CCC(=O)N3)c1]

$^1$H NMR (400 MHz, DMSO-d$_6$) δ ppm: 10.38 (s, 1H), 10.12 (s, 1H), 7.45-7.60 (m, 2H), 7.08 (t, J=8.3 Hz, 1H), 6.89 (d, J=8.2 Hz, 1H), 6.60-6.69 (m, 2H), 6.44-6.60 (m, 1H), 3.62 (s, 3H), 2.88 (t, J=7.6 Hz, 2H), 2.39-2.45 (t, J=7.5 Hz, 2H). LC/MS: Method 1, retention time: 4.513 min; HRMS: m/z (M+)=332.0830 (Calculated for C$_{16}$H$_{16}$N$_2$O$_4$S=332.0831).

Compound 16. N-(3-fluorophenyl)-2-oxo-1,2,3,4-tetrahydroquinoline-6-sulfonamide

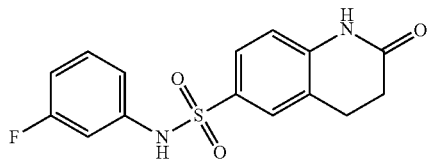 [SMILES: O=C1CCc2cc(S(=O)(=O)Nc3cccc(F)c3)ccc2N1]

$^1$H NMR (400 MHz, DMSO-d$_6$) δ ppm: 10.28-10.52 (m, 2H), 7.43-7.65 (m, 2H), 7.13-7.31 (m, 1H), 6.85-6.99 (m, 3H), 6.71-6.85 (m, 1H), 2.89 (t, J=7.6 Hz, 2H), 2.36-2.46 (t, J=7.1 Hz, 2H). LC/MS: Method 1, retention time: 4.650 min; m/z (M+)=320.0628 (Calculated for C$_{15}$H$_{13}$FN$_2$O$_3$S=320.0631).

Compound 17. 2-oxo-N-(3-(trifluoromethyl)phenyl)-1,2,3,4-tetrahydroquinoline-6-sulfonamide

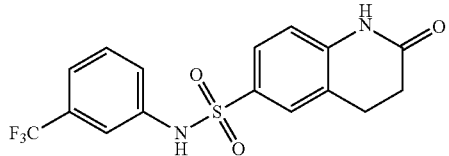 [SMILES: O=C1CCc2cc(S(=O)(=O)Nc3cccc(C(F)(F)F)c3)ccc2N1]

$^1$H NMR (400 MHz, DMSO-d$_6$) δ ppm: 10.56 (s, 1H), 10.41 (s, 1H), 7.51-7.64 (m, 2H), 7.45 (t, J=8.1 Hz, 1H), 7.24-7.39 (m, 3H), 6.90 (d, J=8.4 Hz, 1H), 2.88 (t, J=7.6 Hz, 2H), 2.37-2.45 (t, J=7.9 Hz, 2H). LC/MS: Method 1, retention time: 5.151 min; HRMS: m/z (M+)=370.0596 (Calculated for C$_{16}$H$_{13}$F$_3$N$_2$O$_3$S=370.0599).

Compound 18. N-(biphenyl-3-yl)-2-oxo-1,2,3,4-tetrahydroquinoline-6-sulfonamide

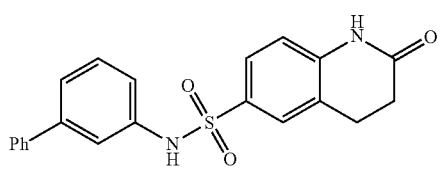

$^1$H NMR (400 MHz, DMSO-d$_6$) δ ppm: 10.38 (s, 1H), 10.23 (br. s., 1H), 7.51-7.65 (m, 2H), 7.44 (dt, J=15.0, 7.6 Hz, 4H), 7.16-7.38 (m, 4H), 7.06 (dd, J=6.8, 1.6 Hz, 1H), 6.90 (d, J=8.4 Hz, 1H), 2.88 (t, J=7.5 Hz, 2H), 2.42 (t, J=7.5 Hz, 2H). LC/MS: Method 1, retention time: 5.406 min; HRMS: m/z (M+)=378.1039 (Calculated for C$_{21}$H$_{18}$N$_2$O$_3$S=378.1038).

Compound 19. 2-oxo-N-(pyridin-3-yl)-1,2,3,4-tetrahydroquinoline-6-sulfonamide

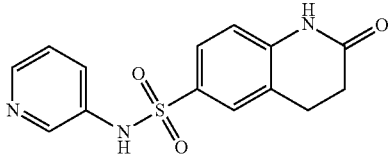 [SMILES: O=C1CCc2cc(S(=O)(=O)Nc3cccnc3)ccc2N1]

$^1$H NMR (400 MHz, DMSO-d$_6$) δ ppm: 10.33-10.53 (m, 2H), 8.15-8.33 (m, 2H), 7.57 (s, 1H), 7.46-7.54 (m, 2H), 7.29 (dd, J=8.2, 4.7 Hz, 1H), 6.90 (d, J=8.4 Hz, 1H), 2.89 (t, J=7.6 Hz, 2H), 2.39-2.44 (t, J=7.4 Hz, 2H). LC/MS: Method 1, retention time: 2.984 min; HRMS: m/z (M+)=303.0683 (Calculated for C$_{14}$H$_{13}$N$_3$O$_3$S=303.0678).

Compound 20. N-(4-chlorophenyl)-2-oxo-1,2,3,4-tetrahydroquinoline-6-sulfonamide

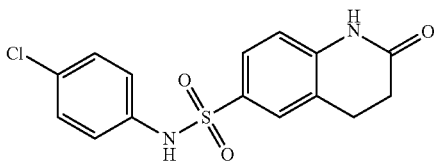 [SMILES: O=C1CCc2cc(S(=O)(=O)Nc3ccc(Cl)cc3)ccc2N1]

$^1$H NMR (400 MHz, DMSO-d$_6$) δ ppm: 10.40 (s, 1H), 10.27 (s, 1H), 7.45-7.60 (m, 2H), 7.20-7.33 (m, 2H), 7.06 (d, J=8.8 Hz, 2H), 6.89 (d, J=8.4 Hz, 1H), 2.88 (t, J=7.6 Hz, 2H), 2.37-2.47 (t, J=7.5 Hz, 2H). LC/MS: Method 1, retention time: 4.938 min; HRMS: m/z (M+)=336.0328 (Calculated for C$_{15}$H$_{13}$ClN$_2$O$_3$S=336.0335).

Compound 21. 2-oxo-N-p-tolyl-1,2,3,4-tetrahydroquinoline-6-sulfonamide

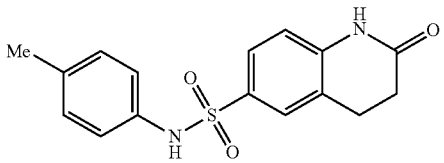 [SMILES: Cc1ccc(NS(=O)(=O)c2ccc3c(c2)CCC(=O)N3)cc1]

$^1$H NMR (400 MHz, DMSO-d$_6$) δ ppm: 10.37 (s, 1H), 9.93 (s, 1H), 7.52 (s, 1H), 7.46 (dd, J=8.4, 2.0 Hz, 1H), 6.91-7.05 (m, 4H), 6.86 (d, J=8.4 Hz, 1H), 2.87 (t, J=7.6 Hz, 2H), 2.38-2.44 (t, J=7.5 Hz, 2H), 2.15 (s, 3H). LC/MS: Method 1, retention time: 4.747 min; HRMS: m/z (M+)=316.0879 (Calculated for C$_{16}$H$_{16}$N$_2$O$_3$S=316.0882).

Compound 22. N-(4-methoxyphenyl)-2-oxo-1,2,3,4-tetrahydroquinoline-6-sulfonamide

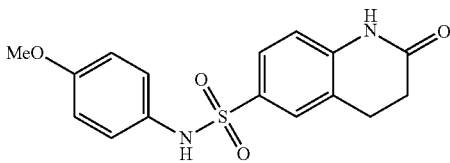 [SMILES: COc1ccc(NS(=O)(=O)c2ccc3c(c2)CCC(=O)N3)cc1]

$^1$H NMR (400 MHz, DMSO-d$_6$) δ ppm: 10.37 (s, 1H), 9.72 (s, 1H), 7.47 (s, 1H), 7.40 (dd, J=8.3, 2.1 Hz, 1H), 6.90-6.97 (m, 2H), 6.86 (d, J=8.2 Hz, 1H), 6.68-6.83 (min, 2H), 3.63 (s, 3H), 2.86 (t, J=7.5 Hz, 2H), 2.36-2.47 (t, J=7.6 Hz, 2H). LC/MS: Method 1, retention time: 4.422 min; HRMS: m/z (M+)=332.0830 (Calculated for C$_{16}$H$_{16}$N$_2$O$_4$S=332.0831).

Compound 23. N-(4-fluorophenyl)-2-oxo-1,2,3,4-tetrahydroquinoline-6-sulfonamide

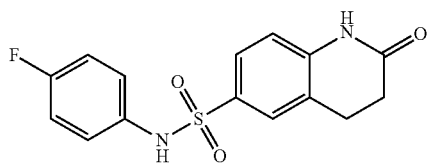 [SMILES: O=C1CCc2cc(S(=O)(=O)Nc3ccc(F)cc3)ccc2N1]

$^1$H NMR (400 MHz, DMSO-d$_6$) δ ppm: 10.39 (s, 1H), 10.04 (s, 1H), 7.50 (s, 1H), 7.45 (dd, J=8.3, 2.1 Hz, 1H), 7.04 (d, J=6.7 Hz, 4H), 6.87 (d, J=8.4 Hz, 1H), 2.87 (t, J=7.6 Hz, 2H), 2.38 (t, J=7.5 Hz, 2H). LC/MS: Method 1, retention time: 4.580 min; HRMS: m/z (M+)=320.0633 (Calculated for C$_{15}$H$_{13}$FN$_2$O$_3$S=320.0631).

Compound 24. 2-oxo-N-o-tolyl-1,2,3,4-tetrahydroquinoline-6-sulfonamide

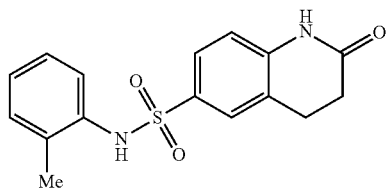 [SMILES: Cc1ccccc1NS(=O)(=O)c1ccc2c(c1)CCC(=O)N2]

$^1$H NMR (400 MHz, DMSO-d$_6$) δ ppm: 10.40 (s, 1H), 9.33 (br. s., 1H), 7.32-7.50 (m, 2H), 6.96-7.14 (m, 3H), 6.83-6.96 (m, 2H), 2.86 (t, J=7.5 Hz, 2H), 2.40 (t, J=7.4 Hz, 2H), 2.01 (s, 3H). LC/MS: Method 1, retention time: 4.656 min; HRMS: m/z (M+)=316.0870 (Calculated for C$_{16}$H$_{16}$N$_2$O$_3$S=316.0882).

Compound 25. N-(2-methoxyphenyl)-2-oxo-1,2,3,4-tetrahydroquinoline-6-sulfonamide

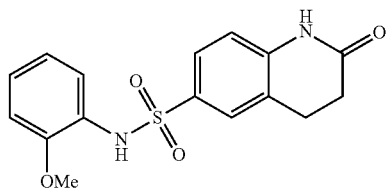 [SMILES: COc1ccccc1NS(=O)(=O)c1ccc2c(c1)CCC(=O)N2]

$^1$H NMR (400 MHz, DMSO-d$_6$) δ ppm: 10.36 (s, 1H), 9.21 (s, 1H), 7.50 (s, 1H), 7.43 (dd, J=8.4, 2.0 Hz, 1H), 7.16 (dd, J=7.8, 1.4 Hz, 1H), 7.06 (td, J=7.8, 1.6 Hz, 1H), 6.70-6.92 (m, 3H), 3.50 (s, 3H), 2.86 (t, J=7.5 Hz, 2H), 2.41

(t, J=7.2 Hz, 2H). LC/MS: Method 1, retention time: 4.580 min; HRMS: m/z (M+)=332.0833 (Calculated for $C_{16}H_{16}N_2O_4S$=332.0831).

Compound 26. N-(2-fluorophenyl)-2-oxo-1,2,3,4-tetrahydroquinoline-6-sulfonamide

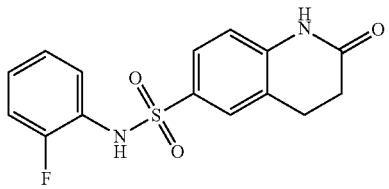 [SMILES: O=C1CCc2cc(S(=O)(=O)Nc3ccccc3F)ccc2N1]

$^1$H NMR (400 MHz, DMSO-$d_6$) δ ppm: 10.40 (s, 1H), 9.95 (s, 1H), 7.42-7.54 (m, 2H), 7.20 (t, J=7.9 Hz, 1H), 7.02-7.16 (m, 3H), 6.89 (d, J=8.4 Hz, 1H), 2.87 (t, J=7.5 Hz, 2H), 2.38 (t, J=7.5 Hz, 2H), LC/MS: Method 1, retention time: 4.455 min; m/z (M+)=320.0629 (Calculated for $C_{15}H_{13}FN_2O_3S$=320.0631).

Compound 27. N-(naphthalen-2-yl)-2-oxo-1,2,3,4-tetrahydroquinoline-6-sulfonamide

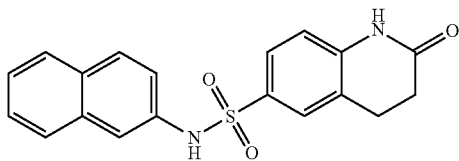 [SMILES: O=C1CCc2cc(S(=O)(=O)Nc3ccc4ccccc4c3)ccc2N1]

$^1$H NMR (400 MHz, DMSO-$d_6$) δ ppm: 10.35 (br. s., 2H), 7.66-7.82 (m, 3H), 7.48-7.66 (m, 3H), 7.32-7.48 (m, 2H), 7.26 (dd, J=8.8, 2.0 Hz, 1H), 6.86 (d, J=8.2 Hz, 1H), 2.85 (t, J=7.5 Hz, 2H), 2.40 (t, J=7.5 Hz 2H). LC/MS: Method 1, retention time: 5.077 min; HRMS: m/z (M+)=352.0883 (Calculated for $C_{19}H_{16}N_2O_3S$=352.0882).

Compound 28. N-(naphthalen-1-yl)-2-oxo-1,2,3,4-tetrahydroquinoline-6-sulfonamide

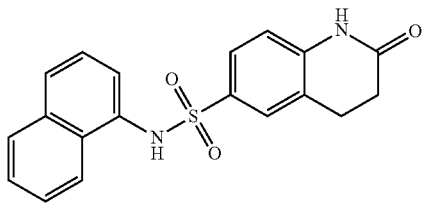 [SMILES: O=C1CCc2cc(S(=O)(=O)Nc3cccc4ccccc34)ccc2N1]

$^1$H NMR (400 MHz, DMSO-$d_6$) δ ppm: 10.36 (s, 1H), 10.01 (s, 1H), 8.01 (d, J=8.2 Hz, 1H), 7.84 (d, J=7.8 Hz, 1H), 7.73 (d, J=8.2 Hz, 1H), 7.28-7.52 (m, 5H), 7.12 (d, J=7.2 Hz, 1H), 6.83 (d, J=8.2 Hz, 1H), 2.81 (t, J=7.5 Hz, 2H), 2.40 (t, J=8.1 Hz, 2H). LC/MS: Method 1, retention time: 4.938 min; HRMS: m/z (M+)=352.0883 (Calculated for $C_{19}H_{16}N_2O_3S$=352.0882).

Compound 29. N-(2,3-dihydrobenzo[b][1,4]dioxin-6-yl)-2-oxo-1,2,3,4-tetrahydroquinoline-6-sulfonamide

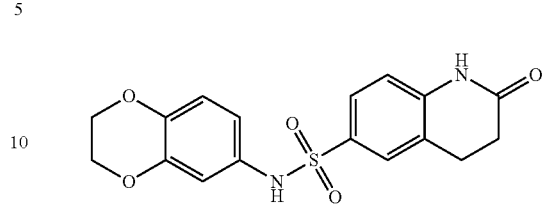

$^1$H NMR (400 MHz, DMSO-$d_6$) δ ppm: 10.38 (s, 1H), 9.78 (s, 1H), 7.39-7.54 (m, 2H), 6.88 (d, J=8.4 Hz, 1H), 6.67 (d, J=8.6 Hz, 1H), 6.42-6.58 (m, 2H), 4.12 (m, 4H), 2.88 (t, J=7.6 Hz, 2H), 2.39 (t, J=7.8 Hz, 2H). LC/MS: Method 1, retention time: 4.363 min; HRMS: m/z (M+)=360.0781 (Calculated for $C_{17}H_{16}N_2O_5S$=360.0780).

Compound 30. N-benzyl-2-oxo-1,2,3,4-tetrahydroquinoline-6-sulfonamide

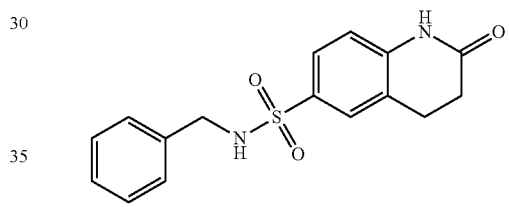

$^1$H NMR (400 MHz, DMSO-$d_6$) δ ppm: 10.38 (s, 1H), 7.93 (t, J=6.4 Hz, 1H), 7.47-7.58 (m, 2H), 7.11-7.34 (m, 5H), 6.91 (d, J=8.0 Hz, 1H), 3.92 (d, J=6.3 Hz, 2H), 2.88 (t, J=7.5 Hz, 2H), 2.39 (t, J=7.5 Hz, 2H). LC/MS: Method 1, retention time: 4.528 min; HRMS: m/z (M+)=316.0882 (Calculated for $C_{16}H_{16}N_2O_3S$=316.0882).

Compound 31. N-(3,4-dimethylphenyl)-7-fluoro-2-oxo-1,2,3,4-tetrahydroquinoline-6-sulfonamide

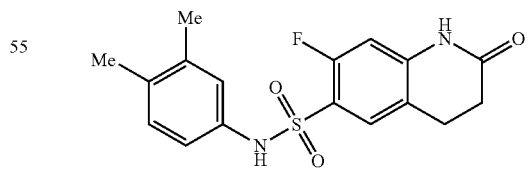

$^1$H NMR (400 MHz, DMSO-$d_6$) δ ppm: 10.42 (s, 1H), 10.14 (s, 1H), 7.56 (d, J=7.6 Hz, 1H), 6.88-7.02 (m, 1H), 6.75-6.88 (m, 2H), 6.67 (d, J=11.3 Hz, 1H), 2.85 (t, J=7.5 Hz, 2H), 2.37 (t, J=7.2 Hz, 2H), 2.06 (m, 6H). LC/MS: Method 1, retention time: 5.105 min; HRMS: m/z (M+)=348.0949 (Calculated for $C_{17}H_{17}FN_2O_3S$=348.0944).

Compound 35. 6-chloro-N-(3,4-dimethylphenyl)-2-oxo-1,2,3,4-tetrahydroquinoline-7-sulfonamide

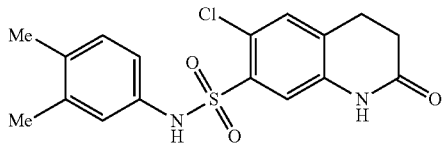 [SMILES: Cc1ccc(NS(=O)(=O)c2cc3c(cc2Cl)CCC(=O)N3)cc1C]

$^1$H NMR (400 MHz, DMSO-$d_6$) δ ppm: 10.38 (br. s., 1H), 10.12 (br. s., 1H), 7.76 (s, 1H), 6.60-7.13 (m, 4H), 2.81 (t, J=7.5 Hz, 2H), 2.39 (t, J=7.7 Hz, 2H), 2.03 (m, 6H) LC/MS: Method 1, retention time: 5.188 min; HRMS: m/z (M+)=364.0652 (Calculated for $C_{17}H_{17}ClN_2O_3S$=364.0648).

Compound 37. 6-chloro-N-(3,4-dimethylphenyl)-3-oxo-3,4-dihydro-2H-benzo[b][1,4]oxazine-7-sulfonamide

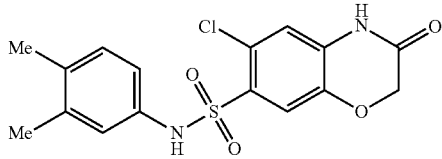 [SMILES: Cc1ccc(NS(=O)(=O)c2cc3c(cc2Cl)NC(=O)CO3)cc1C]

$^1$H NMR (400 MHz, DMSO-$d_6$) δ ppm: 11.05 (s, 1H), 10.25 (s, 1H), 7.39 (s, 1H), 6.69-7.13 (m, 4H), 4.62 (s, 2H), 2.05 (m, 6H). LC/MS: Method 1, retention time: 5.308 min; HRMS: m/z (M+)=366.0446 (Calculated for $C_{16}H_{15}ClN_2O_4S$=366.0441).

Compound 38. 6-bromo-N-(3,4-dimethylphenyl)-3-oxo-3,4-dihydro-2H-benzo[b][1,4]oxazine-7-sulfonamide

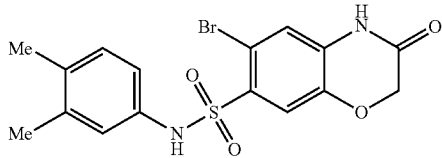 [SMILES: Cc1ccc(NS(=O)(=O)c2cc3c(cc2Br)NC(=O)CO3)cc1C]

$^1$H NMR (400 MHz, DMSO-$d_6$) δ ppm: 10.89 (s, 1H), 10.21 (s, 1H), 7.57 (s, 1H), 7.32 (s, 1H), 6.94 (d, J=8.2 Hz, 1H), 6.85 (s, 1H), 6.77 (dd, J=8.1, 2.1 Hz, 1H), 4.65 (s, 2H), 2.06 (d, 6H). LC/MS: Method 1, retention time: 5.394 min; HRMS: m/z (M+)=409.9939 (Calculated for $C_{16}H_{15}BrN_2O_4S$=409.9936).

Compound 39. N-(3,4-dimethylphenyl)-6-methyl-3-oxo-3,4-dihydro-2H-benzo[b][1,4]oxazine-7-sulfonamide

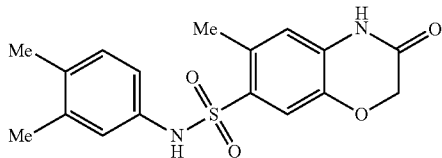 [SMILES: Cc1ccc(NS(=O)(=O)c2cc3c(cc2C)NC(=O)CO3)cc1C]

$^1$H NMR (400 MHz, DMSO-$d_6$) δ ppm: 10.93 (s, 1H), 10.04 (br. s., 1H), 7.29 (s, 1H), 6.92 (d, J=8.2 Hz, 1H), 6.80 (s, 1H), 6.66-6.79 (m, 2H), 4.56 (s, 2H), 2.41 (s, 3H), 2.11 (m, 6 H). LC/MS: Method 1, retention time: 5.202 min. HRMS: m/z (M+)=346.0993 (Calculated for $C_{17}H_{18}N_2O_4S$=346.0987).

Compound 41. N-(3,4-dimethylphenyl)-N-methyl-2-oxo-1,2,3,4-tetrahydroquinoline-6-sulfonamide

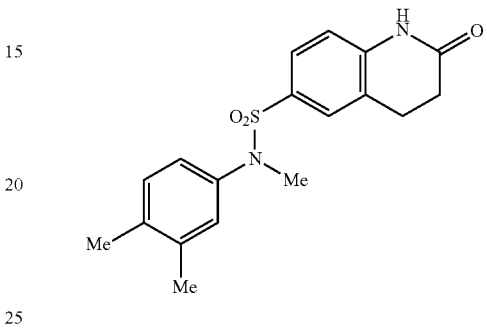

$^1$H NMR (400 MHz, DMSO-$d_6$) δ ppm: 10.44 (br. s., 1H), 7.32 (s, 1H), 7.17-7.28 (m, 1H), 6.98-7.16 (m, 1H), 6.83-6.98 (m, 2H), 6.72 (d, J=7.8 Hz, 1H), 3.02 (s, 3H), 2.88 (t, J=7.52 Hz, 2H), 2.46 (t, J=7.61 Hz, 2H), 2.15 (s, 3H), 2.12 (s, 3H). LC/MS: Method 1, retention time: 5.457 min; Method 2, retention time: 3.889 min. HRMS: m/z (M+)=344.1199 (Calculated for $C_{18}H_{20}N_2O_3S_2$=344.1195).

Compound 43. N-(3-chloro-4-methylphenyl)-2-oxo-1,2,3,4-tetrahydroquinoline-6-sulfonamide

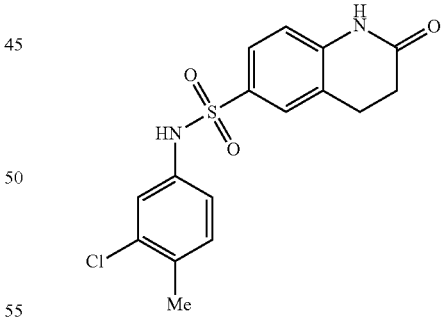

$^1$H NMR (400 MHz, DMSO-$d_6$) δ ppm 10.41 (s, 1H), 10.24 (br. s., 1H), 7.55 (s, 1H), 7.51 (dd, J=8.4, 2.0 Hz, 1H), 7.17 (d, J=8.2 Hz, 1H), 7.08 (d, J=2.2 Hz, 1H), 6.95 (dd, J=8.2, 2.2 Hz, 1H), 6.90 (d, J=8.4 Hz, 1H), 2.89 (t, J=7.6 Hz, 2H), 2.41 (t, J=7.4 Hz, 2H), 2.17 (s, 3H). Method 1, retention time: 5.150 min. HRMS: m/z (M+)=350.0489 (Calculated for $C_{16}H_{15}ClN_2O_3S$=350.0492).

Compound 44. N-(3,4-dichlorophenyl)-2-oxo-1,2,3,4-tetrahydroquinoline-6-sulfonamide

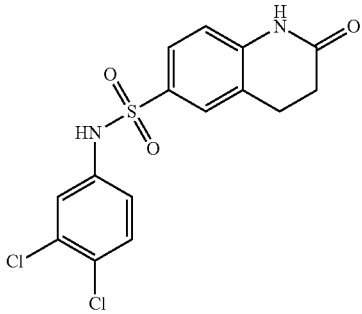 [SMILES: O=C1CCc2cc(S(=O)(=O)Nc3ccc(Cl)c(Cl)c3)ccc2N1]

$^1$H NMR (400 MHz, DMSO-$d_6$) δ ppm 10.54 (s, 1H), 10.42 (s, 1H), 7.51-7.61 (m, 2H), 7.46 (d, J=8.8 Hz, 1H), 7.24 (d, J=2.5 Hz, 1H), 7.05 (dd, J=8.7, 2.4 Hz, 1H), 6.92 (d, J=8.4 Hz, 1H), 2.90 (t, J=7.6 Hz, 3H), 2.49 (t, J=7.6 Hz, 3H). Method 1, retention time: 5.279 min. HRMS: m/z (M+)=369.9942 (Calculated for $C_{15}H_{12}Cl_2N_2O_3S$=369.9942).

Compound 45. 6-chloro-N-(5-chloro-2-methylphenyl)-2-oxo-1,2,3,4-tetrahydroquinoline-7-sulfonamide

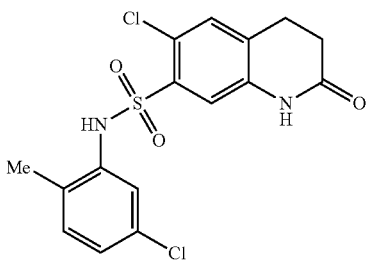 [SMILES: Cc1ccc(Cl)cc1NS(=O)(=O)c1cc2c(cc1Cl)CCC(=O)N2]

$^1$H NMR (400 MHz, DMSO-$d_6$) δ ppm 10.47 (s, 1H), 9.89 (br. s., 1H), 7.66 (s, 1H), 7.09-7.22 (m, 2H), 7.06 (d, J=2.0 Hz, 1H), 7.00 (s, 1H), 2.87 (t, J=7.6 Hz, 2H), 2.39-2.46 (t, J=7.3 Hz, 2H); Method 1, retention time: 5.328 min. HRMS: m/z (M+)=384.0106 (Calculated for $C_{16}H_{14}Cl_2N_2O_3S$=384.0102).

Compound 46. N-(3-cyanophenyl)-2-oxo-1,2,3,4-tetrahydroquinoline-6-sulfonamide

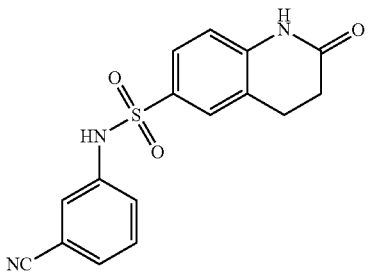 [SMILES: N#Cc1cccc(NS(=O)(=O)c2ccc3c(c2)CCC(=O)N3)c1]

$^1$H NMR (400 MHz, DMSO-$d_6$) δ ppm 10.60 (s, 1H), 10.41 (s, 1H), 7.51-7.63 (m, 2H), 7.30-7.51 (m, 4H), 6.90 (d, J=8.2 Hz, 1H), 2.89 (t, J=7.5 Hz, 2H), 2.40-2.44 (t, J=7.5 Hz, 2H); Method 1, retention time: 4.389 min. HRMS: m/z (M+)=327.0672 (Calculated for $C_{26}H_{13}N_3O_3S$=327.0678).

Compound 47. 1-acetyl-N-(3,4-dimethylphenyl)-2-methylindoline-5-sulfonamide

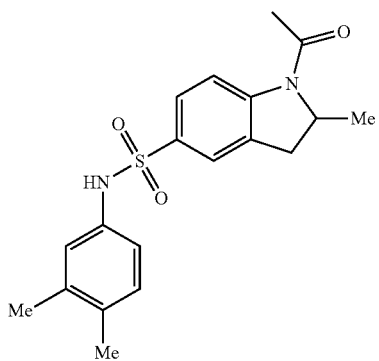 [SMILES: CC(=O)N1c2ccc(S(=O)(=O)Nc3ccc(C)c(C)c3)cc2CC1C]

$^1$H NMR (400 MHz, DMSO-$d_6$) δ ppm 9.88 (br. s., 1H), 7.99 (br. s., 1H), 7.48-7.71 (m, 2H), 6.93 (d, J=6.1 Hz, 1H), 6.71-6.88 (m, 2H), 4.62 (br. s., 1H), 2.21 (s, 3H), 2.07 (m, 6H), 1.16 (d, J=3.5 Hz, 3H); Method 1, retention time: 5.574 min. HRMS: m/z (M+)=358.1353 (Calculated for $C_{19}H_{22}N_2O_3S$=358.1351).

Compound 48. N-(5-chloro-2-methylphenyl)-7-fluoro-2-oxo-1,2,3,4-tetrahydroquinoline-6-sulfonamide

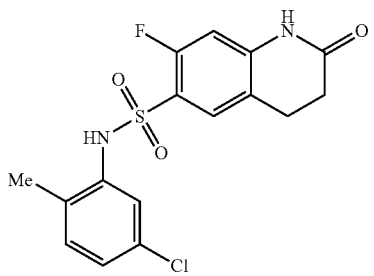 [SMILES: Cc1ccc(Cl)cc1NS(=O)(=O)c1cc2c(cc1F)NC(=O)CC2]

$^1$H NMR (400 MHz, DMSO-$d_6$) δ ppm 10.47 (s, 1H), 9.94 (s, 1H), 7.46 (d, J=7.8 Hz, 1H), 7.10-7.24 (m, 2H), 7.07 (d, J=1.8 Hz, 1H), 6.72 (d, J=11.3 Hz, 1H), 2.84 (t, J=7.6 Hz, 2H), 2.39-2.45 (t, J=7.6 Hz, 2H), 2.05 (s, 3H); Method 1, retention time: 5.197 min. HRMS: m/z (M+)=368.0389 (Calculated for $C_{16}H_{14}ClFN_2O_3S$=368.0398).

Compound 49. 6-chloro-N-(3-chloro-4-methylphenyl)-2-oxo-1,2,3,4-tetrahydroquinoline-7-sulfonamide

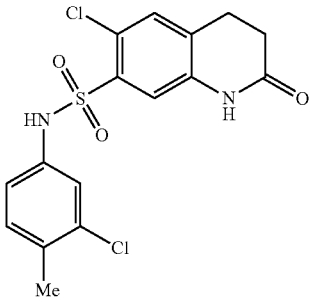 [SMILES: Cc1ccc(NS(=O)(=O)c2cc3c(cc2Cl)CCC(=O)N3)cc1Cl]

$^1$H NMR (400 MHz, DMSO-d$_6$) δ ppm 10.55 (br. s., 1H), 10.44 (s, 1H), 7.84 (s, 1H), 7.16 (d, J=8.2 Hz, 1H), 7.08 (d, J=2.2 Hz, 1H), 6.85-6.99 (m, 2H), 2.91 (t, J=7.6 Hz, 2H), 2.41 (t, J=7.5 Hz, 2H), 2.16 (s, 3H); Method 1, retention time: 5.405 min. HRMS: m/z (M+)=384.0094 (Calculated for C$_{16}$H$_{14}$Cl$_2$N$_2$O$_3$S=384.0102).

Compound 50. N-(3-chloro-2-methylphenyl)-7-fluoro-2-oxo-1,2,3,4-tetrahydroquinoline-6-sulfonamide

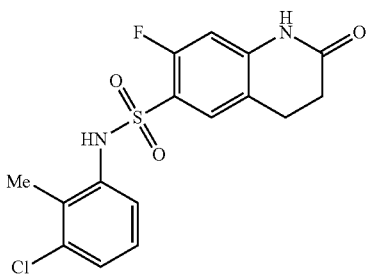 [SMILES: Cc1c(Cl)cccc1NS(=O)(=O)c1cc2c(cc1F)NC(=O)CC2]

$^1$H NMR (400 MHz, DMSO-d$_6$) δ ppm 10.49 (s, 1H), 9.96 (s, 1H), 7.42 (d, J=7.6 Hz, 1H), 7.29 (d, J=7.8 Hz, 1H), 7.11 (t, J=8.0 Hz, 1H), 6.95 (d, J=7.6 Hz, 1H), 6.74 (d, J=11.3 Hz, 1H), 2.84 (t, J=7.6 Hz, 2H), 2.39 (t, J=7.6 Hz, 2H), 2.17 (s, 3H); Method 1, retention time: 5.192 min. HRMS: m/z (M+)=368.0394 (Calculated for C$_{16}$H$_{14}$ClFN$_2$O$_3$S=368.0398).

Compound 51. N-(3-chloro-4-methylphenyl)-7-fluoro-2-oxo-1,2,3,4-tetrahydroquinoline-6-sulfonamide

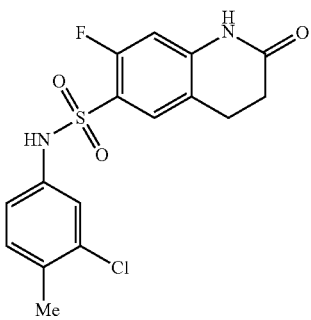 [SMILES: Cc1ccc(NS(=O)(=O)c2cc3c(cc2F)NC(=O)CC3)cc1Cl]

$^1$H NMR (400 MHz, DMSO-d$_6$) δ ppm 10.52 (s, 1H), 10.45 (s, 1H), 7.61 (d, J=7.8 Hz, 1H), 7.18 (d, J=8.4 Hz, 1H), 7.10 (d, J=2.2 Hz, 1H), 6.96 (dd, J=8.2, 2.2 Hz, 1H), 6.69 (d, J=11.3 Hz, 1H), 2.88 (t, J=7.6 Hz, 2H), 2.38-2.46 (t, J=7.4 Hz, 2H), 2.17 (s, 3H); Method 1, retention time: 5.289 min. HRMS: m/z (M+)=368.0387 (Calculated for C$_{16}$H$_{14}$ClFN$_2$O$_3$S=368.0398).

Compound 52. 3-(2-oxo-1,2,3,4-tetrahydroquinoline-6-sulfonamido)phenylboronic acid

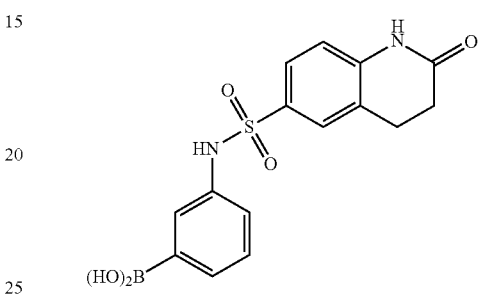

$^1$H NMR (400 MHz, DMSO-d$_6$) δ ppm 10.36 (s, 1H), 9.97 (s, 1H), 7.96 (s, 1H), 7.34-7.58 (m, 3H), 7.01-7.21 (m, 2H), 6.86 (d, J=8.2 Hz, 1H), 3.13 (m, 2H), 2.86 (t, J=7.5 Hz, 2H), 2.42 (t, J=7.6 Hz, 2H); Method 1, retention time: 3.701 min. HRMS: m/z (M+)=345.0821 (Calculated for C$_{15}$H$_{15}$BN$_2$O$_5$S=345.0831).

Compound 53. N-(4-fluoro-3-methylphenyl)-2-oxo-1,2,3,4-tetrahydroquinoline-6-sulfonamide

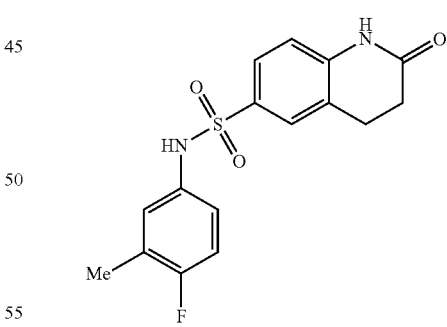

$^1$H NMR (400 MHz, DMSO-d$_6$) δ ppm 10.38 (s, 1H), 9.95 (br. s., 1H), 7.40-7.55 (m, 2H), 6.91-7.01 (m, 2H), 6.74-6.91 (m, 2H), 2.87 (t, J=7.5 Hz, 2H), 2.38-2.45 (t, J=7.5 Hz, 2H), 2.10 (s, 3H); Method 1, retention time: 4.909 min. HRMS: m/z (M+)=334.0781 (Calculated for C$_{16}$H$_{15}$FN$_2$O$_3$S=334.0787).

Compound 54. N-(3,4-dichlorophenyl)-7-fluoro-2-oxo-1,2,3,4-tetrahydroquinoline-6-sulfonamide

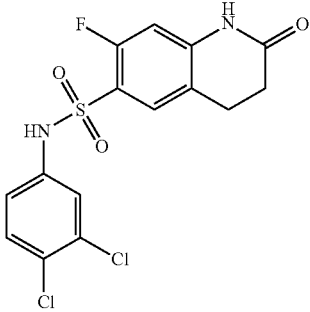 [SMILES: O=C1CCc2cc(S(=O)(=O)Nc3ccc(Cl)c(Cl)c3)c(F)cc2N1]

$^1$H NMR (400 MHz, DMSO-d$_6$) δ ppm 10.84 (s, 1H), 10.48 (s, 1H), 7.66 (d, J=7.6 Hz, 1H), 7.48 (d, J=8.8 Hz, 1H), 7.26 (d, J=2.5 Hz, 1H), 7.06 (dd, J=8.8, 2.5 Hz, 1H), 6.71 (d, J=11.3 Hz, 1H), 2.89 (t, J=7.5 Hz, 2H), 2.39-2.47 (t, J=7.6 Hz, 2H); Method 1, retention time: 5.442 min. HRMS: m/z (M+)=387.9850 (Calculated for C$_{15}$H$_{11}$Cl$_2$FN$_2$O$_3$S=387.9851).

Compound 55. N-(3-fluoro-4-methylphenyl)-2-oxo-1,2,3,4-tetrahydroquinoline-6-sulfonamide

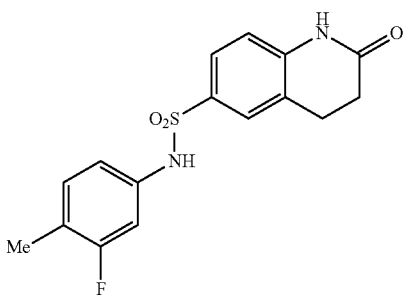 [SMILES: Cc1ccc(NS(=O)(=O)c2ccc3c(c2)CCC(=O)N3)cc1F]

$^1$H NMR (400 MHz, DMSO-d$_6$) δ ppm 10.39 (s, 1H), 10.21 (br. s., 1H), 7.48-7.57 (m, 2H), 7.08 (t, J=8.5 Hz, 1H), 6.89 (d, J=8.2 Hz, 1H), 6.72-6.84 (m, 2H), 2.88 (t, J=7.6 Hz, 2H), 2.41 (t, J=7.6 Hz, 2H), 2.06 (s, 3H); Method 1, retention time: 4.916 min. HRMS: m/z (M+)=334.0775 (Calculated for C$_{16}$H$_{15}$FN$_2$O$_3$S=334.0787).

Compound 56. N-(4-chloro-3-methylphenyl)-7-fluoro-2-oxo-1,2,3,4-tetrahydroquinoline-6-sulfonamide

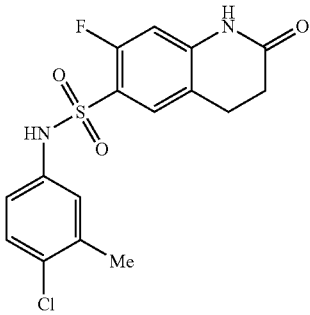

$^1$H NMR (400 MHz, DMSO-d$_6$) δ ppm 10.53 (s, 1H), 10.46 (s, 1H), 7.61 (d, J=7.8 Hz, 1H), 7.18 (d, J=8.4 Hz, 1H), 7.10 (d, J=2.2 Hz, 1H), 6.96 (dd, J=8.2, 2.2 Hz, 1H), 6.69 (d, J=11.3 Hz, 1H), 2.88 (t, J=7.5 Hz, 2H), 2.40 (t, J=7.5 Hz, 2H), 2.17 (s, 3H); Method 1, retention time: 5.294 min. HRMS: m/z (M+)=368.0388 (Calculated for C$_{16}$H$_{14}$ClFN$_2$O$_3$S=368.0398).

Compound 57. 6-chloro-N-(3,4-dimethylphenyl)-2-oxoindoline-5-sulfonamide

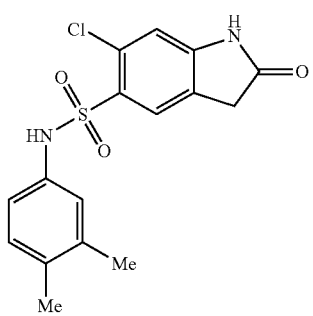 [SMILES: Cc1ccc(NS(=O)(=O)c2cc3c(cc2Cl)NC(=O)C3)cc1C]

$^1$H NMR (400 MHz, DMSO-d$_6$) δ ppm 10.78 (s, 1H), 10.13 (s, 1H), 7.77 (s, 1H), 6.86-6.95 (m, 2H), 6.84 (s, 1H), 6.71-6.82 (m, 1H), 3.50 (s, 2H), 2.06 (s, 3H), 2.04 (s, 3H); Method 1, retention time: 5.069 min. HRMS: m/z (M+)=350.0481 (Calculated for C$_{16}$H$_{15}$ClN$_2$O$_3$S=350.0492).

Compound 58. N-(4-chloro-3-methylphenyl)-2-oxo-1,2,3,4-tetrahydroquinoline-6-sulfonamide

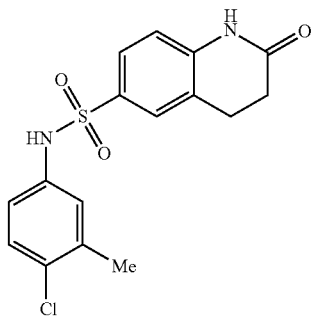 [SMILES: Cc1cc(NS(=O)(=O)c2ccc3c(c2)CCC(=O)N3)ccc1Cl]

$^1$H NMR (400 MHz, DMSO-d$_6$) δ ppm 10.40 (br. s., 2H), 7.55 (m, 2H), 7.14 (m, 3H), 6.90 (d, J=8.4 Hz, 1H), 2.88 (t, J=7.4 Hz, 2H), 2.40 (t, J=7.5 Hz, 2H), 2.20 (s, 3H); Method 1, retention time: 5.160 min. HRMS: m/z (M+)=350.0487 (Calculated for C$_{16}$H$_{15}$ClN$_2$O$_3$S=350.0492).

Compound 59. 6-chloro-N-(3-chloro-2-methylphenyl)-2-oxo-1,2,3,4-tetrahydroquinoline-7-sulfonamide

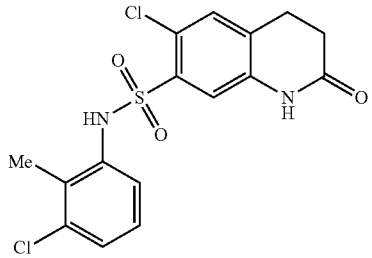 [SMILES: Cc1c(Cl)cccc1NS(=O)(=O)c1cc2c(cc1Cl)CCC(=O)N2]

$^1$H NMR (400 MHz, DMSO-d$_6$) δ ppm 10.48 (s, 1H), 9.89 (s, 1H), 7.61 (s, 1H), 7.28 (d, J=7.8 Hz, 1H), 7.09 (t, J=8.0 Hz, 1H), 7.02 (s, 1H), 6.92 (d, J=7.8 Hz, 1H), 2.86 (t, J=7.6 Hz, 2H), 2.39 (t, J=7.6 Hz, 2H), 2.20 (s, 3H); Method 1, retention time: 5.352 min. HRMS: m/z (M+)=384.0102 (Calculated for C$_{16}$H$_{14}$Cl$_2$N$_2$O$_3$S=384.0102).

Compound 60. 3,3-dichloro-N-(3,4-dimethylphenyl)-2-oxoindoline-5-sulfonamide

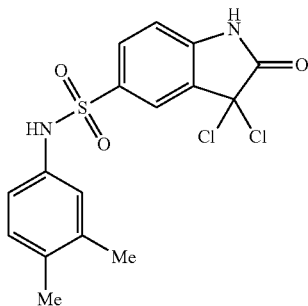 [SMILES: Cc1ccc(NS(=O)(=O)c2ccc3c(c2)C(Cl)(Cl)C(=O)N3)cc1C]

$^1$H NMR (400 MHz, DMSO-d$_6$) δ ppm 11.74 (s, 1H), 9.97 (s, 1H), 7.85 (s, 1H), 7.70 (d, J=8.2 Hz, 1H), 7.05 (d, J=8.2 Hz, 1H), 6.95 (d, J=8.0 Hz, 1H), 6.68-6.88 (m, 2H), 2.06 (s, 6H); Method 1, retention time: 5.779 min. HRMS: m/z (M+)=384.0088 (Calculated for C$_{16}$H$_{14}$Cl$_2$N$_2$O$_3$S=384.0102).

General Procedure for the Synthesis of Compounds 32-34, 36, and 61-70

The methods of synthesizing compound 32 were generally followed for all compounds 32-34, 36, and 61-73.

Compound 32. 7-(dimethylamino)-N-(3,4-dimethylphenyl)-2-oxo-1,2,3,4-tetrahydroquinoline-6-sulfonamide

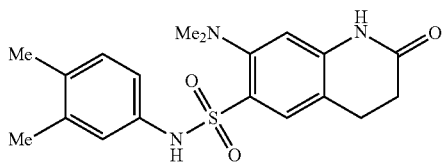 [SMILES: Cc1ccc(NS(=O)(=O)c2cc3c(cc2N(C)C)NC(=O)CC3)cc1C]

In a microwave vial, N-(3,4-dimethylphenyl)-7-fluoro-2-oxo-1,2,3,4-tetrahydroquinoline-6-sulfonamide (0.01 g, 0.029 mmol) was dissolved in acetonitrile (0.5 ml) and dimethylamine (2.0 M THF) (0.029 ml, 0.057 mmol) was added followed by triethylamine (6.00 μl, 0.043 mmol). The solution was heated in a microwave at 180° C. for 1 h, cooled to RT, diluted with DMSO (0.5 mL) and purified by directly injecting to a Waters® reverse phase purification system.

$^1$H NMR (400 MHz, DMSO-d$_6$) δ ppm: 10.19 (s, 1H), 9.41 (s, 1H), 7.50-7.63 (s, 1H), 6.83-6.91 (m, 2H), 6.75-6.83 (m, 2H), 2.80 (t, J=7.5 Hz, 2H), 2.58 (s, 6H), 2.39 (m, 2H), 2.04 (m, 6H). LC/MS: Method 1, retention time: 5.170 min; HRMS: m/z (M+)=373.1461 (Calculated for C$_{19}$H$_{23}$N$_3$O$_3$S=373.1460).

Compound 33. N-(3,4-dimethylphenyl)-7-(methylamino)-2-oxo-1,2,3,4-tetrahydroquinoline-6-sulfonamide

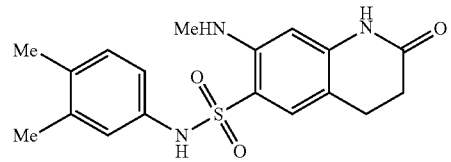 [SMILES: CNc1cc2c(cc1S(=O)(=O)Nc1ccc(C)c(C)c1)CCC(=O)N2]

$^1$H NMR (400 MHz, DMSO-d$_6$) δ ppm: 10.10 (s, 1H), 9.83 (s, 1H), 7.33 (s, 1H), 6.92 (m, 2H), 6.65-6.8 (m, 2H), 6.12 (s, 1H), 2.85 (t, J=7.5 Hz, 2H), 2.69 (d, J=4.6 Hz, 3H), 2.35 (t, J=7.4 Hz, 2H), 2.06 (m, 6H). LC/MS: Method 1, retention time: 5.170 min; HRMS: m/z (M+)=359.1302 (Calculated for C$_{18}$H$_{21}$N$_3$O$_3$S=359.1304).

Compound 34. N-(3,4-dimethylphenyl)-2-oxo-7-(piperidin-1-yl)-1,2,3,4-tetrahydroquinoline-6-sulfonamide

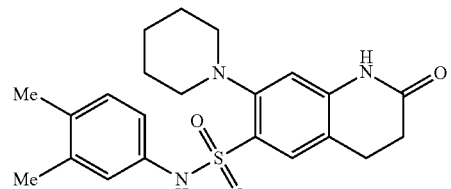

$^1$H NMR (400 MHz, DMSO-d$_6$) δ ppm: 10.21 (s, 1H), 8.93 (s, 1H), 7.61 (s, 1H), 6.88 (d, J=8.2 Hz, 1H), 6.78 (m, 2H), 6.71 (dd, J=8.1, 2.1 Hz, 1H), 2.81 (t, J=7.5 Hz, 2H), 2.70 (m, 4H), 2.40 (t, J=7.6 Hz, 2H), 2.03 (d, J=4.7 Hz, 6H), 1.73 (m, 4H), 1.48 (m, 2H). LC/MS: Method 1, retention time: 5.718 min; HRMS: m/z (M+)=413.1786 (Calculated for C$_{22}$H$_{27}$N$_3$O$_3$S=413.1773).

Compound 36. 6-(dimethylamino)-N-(3,4-dimethylphenyl)-2-oxo-1,2,3,4-tetrahydroquinoline-7-sulfonamide

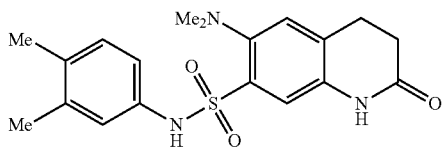 [SMILES: Cc1ccc(NS(=O)(=O)c2cc3c(cc2N(C)C)CCC(=O)N3)cc1C]

¹H NMR (400 MHz, DMSO-d₆) δ ppm: 10.19 (s, 1H), 9.41 (s, 1H), 7.58 (s, 1H), 6.84-6.93 (m, 2H), 6.67-6.84 (m, 2H), 2.80 (t, J=7.5 Hz, 2H), 2.58 (s, 6H), 2.39 (t, J=7.5 Hz, 2H), 1.99-2.07 (m, 6H). LC/MS: Method 1, retention time: 5.196 min; HRMS: m/z (M+)=373.1468 (Calculated for C₁₉H₂₃N₃O₃S=373.1460).

Compound 61. 7-((2-(dimethylamino)ethyl)(methyl)amino)-N-(3,4-dimethylphenyl)-2-oxo-1,2,3,4-tetrahydroquinoline-6-sulfonamide

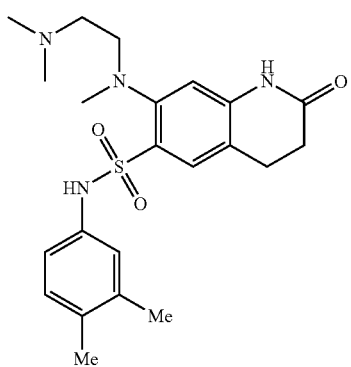 [SMILES: Cc1ccc(NS(=O)(=O)c2cc3c(cc2N(C)CCN(C)C)NC(=O)CC3)cc1C]

¹H NMR (400 MHz, DMSO-d₆) δ ppm 10.29 (br. s., 1H), 9.62 (br. s., 1H), 8.80 (s, 1H), 7.66 (s, 1H), 6.69-6.98 (m, 3H), 3.03-3.18 (m, 2H), 2.73-2.96 (m, 7H), 2.52 (s, 6H), 2.41 (t, J=7.6 Hz, 2H), 2.07 (s, 3H), 2.04 (s, 3H); Method 1, retention time: 4.090 min. HRMS: m/z (M+)=430.2044 (Calculated for C₂₂H₃₀N₄O₃S=430.2039).

Compound 62. N-(3,4-dimethylphenyl)-2-oxo-7-(pyrrolidin-1-yl)-1,2,3,4-tetrahydroquinoline-6-sulfonamide

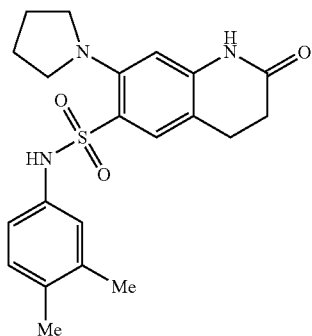 [SMILES: Cc1ccc(NS(=O)(=O)c2cc3c(cc2N2CCCC2)NC(=O)CC3)cc1C]

¹H NMR (400 MHz, DMSO-d₆) δ ppm 10.12 (s, 1H), 9.41 (s, 1H), 7.56 (s, 1H), 6.89 (d, J=8.0 Hz, 1H), 6.80 (s, 1H), 6.73 (dd, J=8.0, 2.0 Hz, 1H), 6.63 (s, 1H), 3.54 (br. s., 24H), 3.03-3.19 (m, 4H), 2.75 (t, J=7.5 Hz, 3H), 2.37 (t, J=7.5 Hz, 3H), 2.05 (s, 3H), 2.04 (s, 3H), 1.85 (m, 4H); Method 1, retention time: 5.262 min. HRMS: m/z (M+)=399.1620 (Calculated for C₂₁H₂₅N₃O₃S=399.1617).

Compound 63. 7-(3-(dimethylamino)pyrrolidin-1-yl)-N-(3,4-dimethylphenyl)-2-oxo-1,2,3,4-tetrahydroquinoline-6-sulfonamide

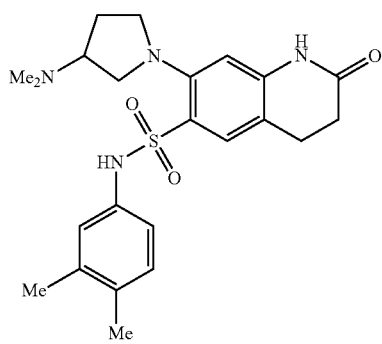 [SMILES: Cc1ccc(NS(=O)(=O)c2cc3c(cc2N2CCC(N(C)C)C2)NC(=O)CC3)cc1C]

¹H NMR (400 MHz, DMSO-d₆) δ ppm 10.27 (s, 1H), 9.35 (s, 1H), 7.60 (s, 1H), 6.91 (d, J=8.0 Hz, 1H), 6.79 (s, 2H), 6.72 (dd, J=8.1, 1.9 Hz, 1H), 3.23 (m, 1H), 3.09-3.18 (m, 1H), 3.03 (m, 1H), 2.70-2.88 (m, 6H), 2.46 (s, 6H), 2.39 (m, 2H), 2.06 (m, 9H); Method 1, retention time: 4.092 min. HRMS: m/z (M+)=442.2040 (Calculated for C₂₃H₃₀N₄O₃S=442.2039).

Compound 64. N-(3,4-dimethylphenyl)-7-(2-hydroxy-2-methylpropylamino)-2-oxo-1,2,3,4-tetrahydroquinoline-6-sulfonamide

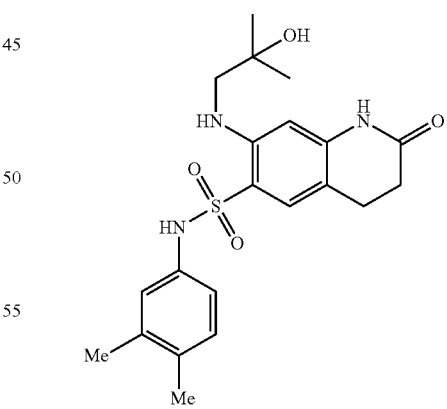

¹H NMR (400 MHz, DMSO-d₆) δ ppm 10.03 (s, 1H), 9.84 (s, 1H), 7.33 (s, 1H), 6.91 (d, J=8.0 Hz, 1H), 6.79 (d, J=1.8 Hz, 1H), 6.72 (dd, J=8.0, 2.2 Hz, 1H), 6.05-6.23 (m, 2H), 2.87 (d, J=4.5 Hz, 2H), 2.68 (t, J=7.4 Hz, 2H), 2.50 (s, 1H), 2.36 (t, J=7.4 Hz, 2H), 2.05 (m, 6H), 1.12 (s, 6H); Method 1, retention time: 5.052 min. HRMS: m/z (M+)=417.1723 (Calculated for C₂₁H₂₇N₃O₄S=417.1722).

Compound 65, N-(3,4-dimethylphenyl)-7-(isopropylamino)-2-oxo-1,2,3,4-tetrahydroquinoline-6-sulfonamide

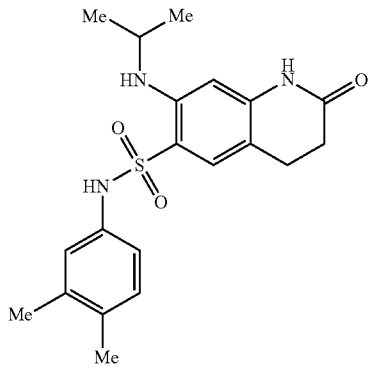 [SMILES: Cc1ccc(NS(=O)(=O)c2cc3c(cc2NC(C)C)NC(=O)CC3)cc1C]

$^1$H NMR (400 MHz, DMSO-d$_6$) δ ppm 10.03 (s, 1H), 9.92 (s, 1H), 7.34 (s, 1H), 6.92 (d, J=8.0 Hz, 1H), 6.77 (s, 1H), 6.71 (dd, J=8.1, 2.1 Hz, 1H), 6.17 (s, 1H), 5.52 (d, J=7.2 Hz, 1H), 3.37-3.50 (m, 1H), 2.68 (t, J=7.4 Hz, 3H), 2.36 (t, J=7.5 Hz, 3H), 2.06 (s, 3H), 2.05 (s, 3H), 1.07 (d, J=6.3 Hz, 6H); Method 1, retention time: 5.596 min, HRMS: m/z (M+)=387.1614 (Calculated for C$_{20}$H$_{25}$N$_3$O$_3$S=387.1617).

Compound 66. 7-(diethylamino)-N-(3,4-dimethylphenyl)-2-oxo-1,2,3,4-tetrahydroquinoline-6-sulfonamide

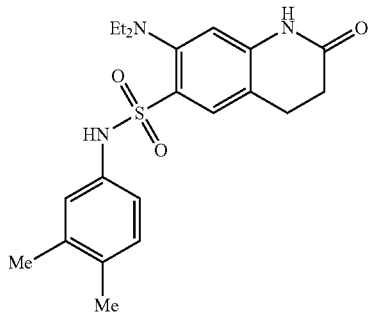

$^1$H NMR (400 MHz, DMSO-d$_6$) δ ppm 10.15 (s, 1H), 9.42 (br. s., 1H), 7.71 (s, 1H), 6.87 (d, J=8.0 Hz, 1H), 6.79 (d, J=2.9 Hz, 2H), 6.71 (dd, J=8.1, 2.1 Hz, 1H), 2.78-2.97 (m, 6H), 2.40 (t, J=7.6 Hz, 2H), 2.04 (s, 3H), 2.03 (s, 3H), 0.88 (t, J=7.1 Hz, 6H); Method 1, retention time: 4.328 min. HRMS: m/z (M+)=401.1775 (Calculated for C$_{21}$H$_{27}$N$_3$O$_3$S=401.1773).

Compound 67. N-(3,4-dimethylphenyl)-7-(1-hydroxypropan-2-ylamino)-2-oxo-1,2,3,4-tetrahydroquinoline-6-sulfonamide

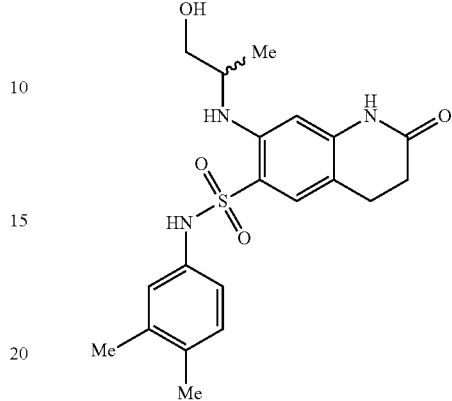

$^1$H NMR (400 MHz, DMSO-d$_6$) δ ppm 10.04 (s, 1H), 9.84 (s, 1H), 7.32 (s, 1H), 6.91 (d, J=8.0 Hz, 1H), 6.77 (s, 1H), 6.72 (d, J=8.0 Hz, 1H), 6.21 (s, 1H), 5.77 (d, J=6.3 Hz, 1H), 4.82 (br. s., 1H), 3.40-3.34 (m, 3H), 2.67 (t, J=7.4 Hz, 2H), 2.35 (t, J=7.3 Hz, 2H), 2.06 (s, 3H), 2.05 (s, 3H), 1.03 (d, J=5.1 Hz, 3H); Method 1, retention time: 4.943 min. HRMS: m/z (M+)=403.1564 (Calculated for C$_{20}$H$_{25}$N$_3$O$_3$S=403.1566).

Compound 68. (S)—N-(3,4-dimethylphenyl)-7-(1-hydroxypropan-2-ylamino)-2-oxo-1,2,3,4-tetrahydroquinoline-6-sulfonamide

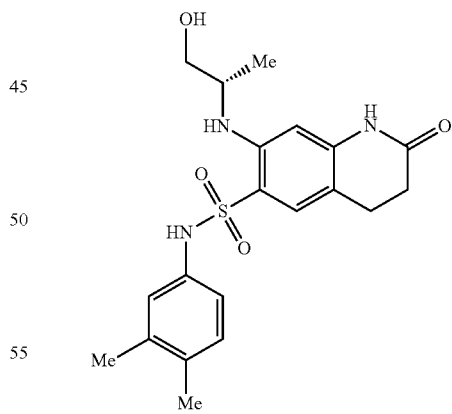

$^1$H NMR (400 MHz, DMSO-d$_6$) δ ppm 10.04 (s, 1H), 9.84 (s, 1H), 7.32 (s, 1H), 6.91 (d, J=8.0 Hz, 1H), 6.77 (s, 1H), 6.72 (d, J=8.0 Hz, 1H), 6.21 (s, 1H), 5.77 (d, J=6.3 Hz, 1H), 4.82 (br. s., 1H), 3.40-3.34 (m, 3H), 2.67 (t, J=7.4 Hz, 2H), 2.35 (t, J=7.3 Hz, 2H), 2.06 (s, 3H), 2.05 (s, 3H), 1.03 (d, J=5.1 Hz, 3H); [α]$_D$=−53 (c=1.0, MeOH). Method 1, retention time: 4.943 min. HRMS: m/z (M+)=403.1562 (Calculated for C$_{20}$H$_{25}$N$_3$O$_3$S=403.1566).

Compound 69. (R)—N-(3,4-dimethylphenyl)-7-(1-hydroxypropan-2-ylamino)-2-oxo-1,2,3,4-tetrahydroquinoline-6-sulfonamide

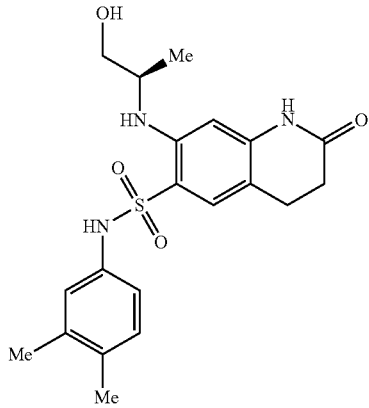 [SMILES: Cc1ccc(NS(=O)(=O)c2cc3c(cc2N[C@H](C)CO)NC(=O)CC3)cc1C]

¹H NMR (400 MHz, DMSO-d₆) δ ppm 10.04 (s, 1H), 9.84 (s, 1H), 7.32 (s, 1H), 6.91 (d, J=8.0 Hz, 1H), 6.77 (s, 1H), 6.72 (d, J=8.0 Hz, 1H), 6.21 (s, 1H), 5.77 (d, J=6.3 Hz, 1H), 4.82 (br. s., 1H), 3.40-3.34 (m, 3H), 2.67 (t, J=7.4 Hz, 2H), 2.35 (t, J=7.3 Hz, 2H), 2.06 (s, 3H), 2.05 (s, 3H), 1.03 (d, J=5.1 Hz, 3H); [α]=53 (c=1.0, MeOH). Method 1, retention time: 4.943 min. HRMS: m/z (M+)=403.1565 (Calculated for $C_{20}H_{25}N_3O_3S$ 403.1566).

Compound 70. N-(3,4-dimethylphenyl)-7-(2-hydroxyethylamino)-2-oxo-1,2,3,4-tetrahydroquinoline-6-sulfonamide

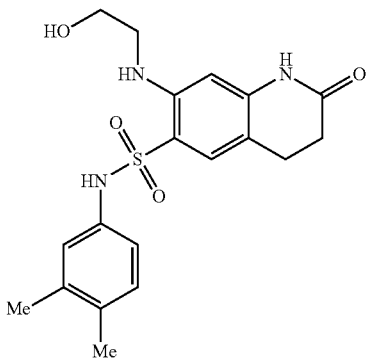 [SMILES: Cc1ccc(NS(=O)(=O)c2cc3c(cc2NCCO)NC(=O)CC3)cc1C]

1H NMR (400 MHz, DMSO-d₆) δ ppm 10.06 (br. s., 1H), 9.85 (br. s., 1H), 7.32 (s, 1H), 6.91 (d, J=8.0 Hz, 1H), 6.67-6.82 (m, 2H), 6.18 (s, 1H), 5.95 (br. s., 1H), 4.78 (br. s., 1H), 3.55 (t, J=5.4 Hz, 2H), 3.06 (t, J=5.3 Hz, 2H), 2.67 (t, J=7.4 Hz, 2H), 2.35 (t, J=7.3 Hz, 2H), 2.06 (s, 3H), 2.05 (s, 3H); Method 1, retention time: 4.752 min; HRMS: m/z (M+)=389.1404 (Calculated for $C_{19}H_{23}N_3O_4S$=389.1409).

Compound 71. (S)—N-(3-chloro-4-methylphenyl)-7-(1-hydroxypropan-2-ylamino)-2-oxo-1,2,3,4-tetrahydroquinoline-6-sulfonamide

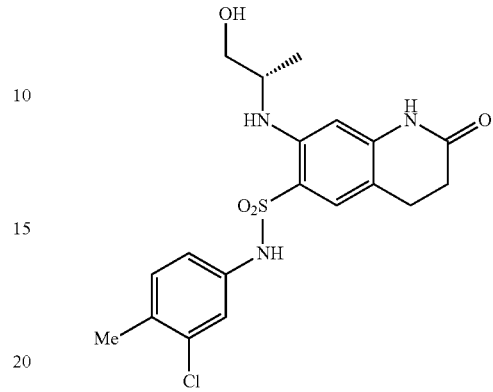

¹H NMR (400 MHz, DMSO-d₆) δ ppm 10.22 (s, 1H) 10.08 (s, 1H) 7.36 (s, 1H) 7.17 (d, J=8.22 Hz, 1H) 7.02 (d, J=1.56 Hz, 1H) 6.89 (dd, J=8.12, 1.66 Hz, 1H) 6.25 (s, 1H) 5.79 (d, J=5.87 Hz, 1H) 4.85 (br. s., 1H) 3.36 (m, 3H) 2.70 (t, J=7.34 Hz, 2H) 2.38 (t, J=7.43 Hz, 2H) 2.18 (s, 3H) 1.05 (d, J=5.48 Hz, 3H). Method 1, retention time: 4.996 min. HRMS: m/z (M+)=423.1018 (Calculated for $C_{19}H_{22}ClN_3O_4S$=423.1020).

Compound 72. (S)—N-(4-fluoro-3-methylphenyl)-7-(1-hydroxypropan-2-ylamino)-2-oxo-1,2,3,4-tetrahydroquinoline-6-sulfonamide

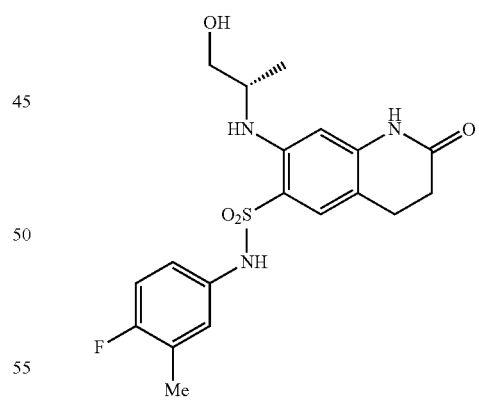

¹H NMR (400 MHz, DMSO-d₆) δ ppm 10.06 (br. s., 1H) 9.94 (s, 1H) 7.33 (d, J=9.00 Hz, 1H) 6.73-7.04 (m, 3H) 6.24 (d, J=9.19 Hz, 1H) 5.79 (br. s., 1H) 4.85 (br. s., 1H) 3.33 (m, 3H) 2.69 (t, J=7.41 Hz, 2H) 2.38 (t, J=7.43 Hz, 2H) 2.11 (s, 3H) 1.03 (d, J=5.51 Hz, 3H). Method 1, retention time: 4.709 min. HRMS: m/z (M+)=407.1319 (Calculated for $C_{19}H_{22}FN_3O_4S$=407.1315).

Compound 73. (S)—N-(3-chloro-4-fluorophenyl)-7-(1-hydroxypropan-2-ylamino)-2-oxo-1,2,3,4-tetrahydroquinoline-6-sulfonamide

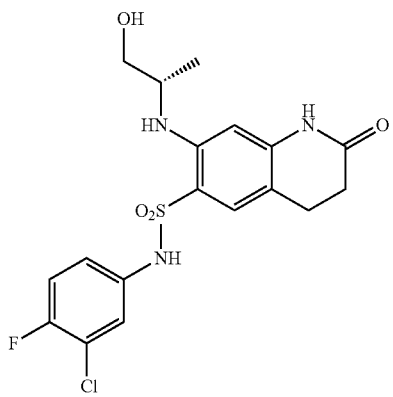 [SMILES: C[C@@H](CO)Nc1cc2c(cc1S(=O)(=O)Nc1ccc(F)c(Cl)c1)CCC(=O)N2]

$^1$H NMR (400 MHz, DMSO-d$_6$) δ ppm 10.28 (br. s., 1H) 10.10 (s, 1H) 7.35-7.28 (m, 3H) 7.12-7.00 (m, 2H) 6.25 (m, 1H) 5.90 (br. s., 1H) 3.20 (m, 3H) 2.70 (t, J=7.41 Hz, 2H) 2.38 (t, J=7.43 Hz, 2H) 1.04 (d, J=5.51 Hz, 3H). Method 1, retention time: 4.881 min, HRMS: m/z (M+)=427.0773 (Calculated for C$_{18}$H$_{19}$ClFN$_3$O$_4$S=427.0769).

General Procedure for the Synthesis of Compound 40

Compound 40. N-(3,4-dimethylphenyl)-3-oxo-6-phenyl-3,4-dihydro-2H-benzo[b][1,4]oxazine-7-sulfonamide

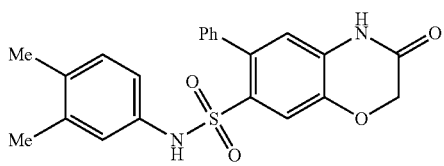 [SMILES: Cc1ccc(NS(=O)(=O)c2cc3c(cc2-c2ccccc2)NC(=O)CO3)cc1C]

To a microwave vial, 6-bromo-N-(3,4-dimethylphenyl)-3-oxo-3,4-dihydro-2H-benzo[b][1,4]oxazine-7-sulfonamide (0.03 g, 0.073 mmol), phenylboronic acid (0.018 g, 0.146 mmol), Tetrakis (2.53 mg, 2.188 mol), sodium carbonate (2.0 M aqueous solution) (0.109 ml, 0.219 mmol) and 1,2-DME (0.5 ml) were added. The vessel was sealed and heated under microwave irradiation at 120° C. for 20 minutes. The reaction was cooled to RT, filtered through a thiol-SPE column (Stratospheres) and the column rinsed with methanol (~2 mL). The resultant solution was purified. $^1$H NMR (400 MHz, DMSO-d$_6$) δ ppm: 11.01 (br. s., 1H), 9.57 (br. s., 1H), 7.46-7.58 (m, 1H), 7.32 (d, J=5.3 Hz, 3H), 7.09-7.25 (m, 2H), 6.91 (d, J=8.0 Hz, 1H), 6.73 (s, 1H), 6.48-6.68 (m, 2H), 4.66 (s, 2H), 1.94-2.14 (m, 6H). LC/MS: Method 1, retention time: 5.946 min; HRMS: m/z (M+)=408.1141 (Calculated for C$_{22}$H$_{20}$N$_2$O$_4$S 408.1144).

General Procedure for the Synthesis of Compound 42

Compound 42. N-(3,4-dimethylphenyl)-2-oxo-1,2,3,4-tetrahydroquinoline-6-carboxamide

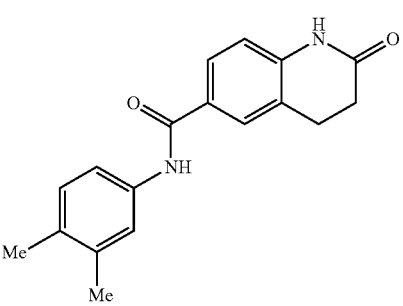 [SMILES: Cc1ccc(NC(=O)c2ccc3c(c2)CCC(=O)N3)cc1C]

2-oxo-1,2,3,4-tetrahydroquinoline-6-carboxylic acid (0.075 g, 0.392 mmol) and 3,4-dimethylaniline (0.052 g, 0.432 mmol) were dissolved in DMF (1 ml) and EDC (0.083 g, 0.432 mmol) was added. The reaction was stirred at RT for 4 h, then directly purified by directly injecting to a Waters® reverse phase purification system.

$^1$H NMR (400 MHz, DMSO-d6) δ ppm: 10.29 (s, 1H), 9.86 (s, 1H), 7.67-7.80 (m, 2H), 7.38-7.53 (m, 2H), 7.04 (d, J=8.2 Hz, 1H), 6.89 (d, J=8.2 Hz, 1H), 3.13 (s, 3H), 2.92 (t, J=7.6 Hz, 2H), 2.45 (t, J=7.65 Hz, 2H), 2.16 (m, 6H). Method 1, retention time: 5.009 min; HRMS: m/z (M+)=294.1361 (Calculated for C$_{18}$H$_{18}$N$_2$O$_2$=294.1368).

EXAMPLE 2

This example illustrates some of the properties of exemplary compounds of the invention.

Structure active relationship (SAR) explorations were done with 2-oxo-N-aryl-1,2,3,4-tetrahydroquinoline-6-sulfonamides, modifying the core 3,4-dihydroquinolin-2(1H)-one heterocycle with the sulfonamide attachment at the 6 and 7 positions of the ring (see Scheme 1 above, which shows the link at C6). The related 2H-benzo[b][1,4]oxazin-3(4H)-one, 1H-benzo[d]imidazol-2(3H)-one, indolin-2-one, and several 3,4-dihydroquinolin-2(1H)-one analogues with F, Cl, and Br substitutions were also explored. Additional SAR explorations were also performed at the 7 position of the 3,4-dihydroquinolin-2(1H)-one heterocycle. To explore aryl analogues at this position, Suzuki-Miyaura couplings between the 7-bromo-3,4-dihydroquinolin-2(1H)-one moiety and selected aryl-boronic acids (see Scheme 1 above) were pursued. A second method for exploring SAR at the 7-position involved displacement of the aryl fluoride of the 7-fluoro-3,4-dihydroquinolin-2(1H)-one moiety with various amines (see Scheme I above).

AC$_{50}$ values were determined utilizing the luminescent pyruvate kinase-luciferase coupled assay (Inglese, J. et al, Quantitative high-throughput screening: a titration-based approach that efficiently identifies biological activities in large chemical libraries. Proc. Natl. Acad. Sci. U.S.A. 2006, 103, 11473-11478).

Reagents.

Kinase-Glo was obtained from Promega (Madison, Wis., USA). ATP, PEP, LDH and NADH were from Sigma (St. Louis, Mo., USA). Reagents and solvents were purchased from Sigma, Alfa Aesar (Ward Hill, Mass., USA), Acros (Morris Plains, N.J., USA), Enamine (Monmouth Jct., NJ, USA), Oakwood Products (West Columbia, S.C., USA), Matrix Scientific (Columbia, S.C., USA) or Chem-Impex International (Wood Dale, Ill., USA).

Luminescent Pyruvate Kinase-Luciferase Coupled Assay.

Production of a luminescent signal based on the generation of ATP by pyruvate kinase was determined by using the ATP-dependent enzyme firefly luciferase. Three μL of substrate mix (at r.t.) in assay buffer (50 mM imidazole pH 7.2, 50 mM KCl, 7 mM $MgCl_2$, 0.01% tween 20, 0.05% BSA) was dispensed into Kalypsys (San Diego, Calif., USA) white solid bottom 1,536 well microtiter plates using a bottle-valve solenoid-based dispenser (Kalypsys). The final concentrations of substrates in the assay were 0.1 mM ADP and 0.5 mM PEP. Twenty-three nL of compound in DMSO were delivered with a 1,536-pin array tool, and 1 μL of enzyme mix in assay buffer (final concentration, 0.1 nM pyruvate kinase, 50 mM imidazole pH 7.2, 0.05% BSA, 4° C.) was added. Microtiter plates were incubated at r.t. for 1 hour and 2 uL of luciferase detection mix (Kinase-Glo from Promega, Madison, Wis., USA) at 4° C. protected from light, was added and luminescence was read with a ViewLux (Perkin Elmer, Waltham, Mass., USA) using a 2 second exposure/plate (with 2× binning). The final concentration of DMSO was 0.5% and found not to affect the assay signal.

Data was normalized for $AC_{50}$ values to control columns containing uninhibited enzyme (n), and $AC_{100}$ inhibition (i) according the following equation: Activation (%)=[(c−n)/(n−i)]*100 where c=compound, n=DMSO neutral, i=no enzyme control. A % activity of 100% is approximately a 2-fold increase over basal assay signal (% Activation by FBP was variable but averaged 100%). Monitoring of activation was accomplished using enzyme at 3× the final concentration.

All compounds were screened using a qHTS approach, where compounds are assayed using at least seven concentrations to generate concentration-response curves for every compounds. Briefly, qHTS uses an inter-plate dilution method where the first plate contains the highest concentration of a set of compounds in DMSO, while subsequent plates contain the same compounds in the same well locations, but at successive lower concentrations. Using the protocol outlined above, the rate was calculated as a plate throughput of 18 plates/hr or approximately 7 samples/sec on the Kalypsys robotic system which means that a 7 point CRC was obtained every second on the robotic system.

Three primary structural aspects of the 2-oxo-N-aryl-1,2,3,4-tetrahydroquinoline-6-sulfonamide molecule were pursued, i.e. the two moieties of the 3,4-dimethylaniline and 3,4-dihydroquinolin-2(1H)-one and the sulfonamide linkage. The first SAR examinations surrounded the linkage between the two aromatic moieties (compounds 41 and 42). An N-methyl sulfonamide (compound 41) version of compound 4 had an $AC_{50}$ of 23.09 μM and Max. Res. of 36.00%. An amide (compound 42) version of compound 4 had an $AC_{50}$ of 40 μM and a Max. Res. of 5%.

The second examination involved the modification of the core 3,4-dihydroquinolin-2(1H)-one heterocycle. Numerous, related heterocyclic sulfonyl chlorides were examined after coupling to 3,4-dimethylaniline to maintain uniformity with the lead from the primary screen. Results detailed in Table 1 demonstrate that the 3,4-dihydroquinolin-2(1H)-one heterocycle retains the best combination of potency and maximum response. Other heterocycles included the related 4-methyl-2H-benzo[b][1,4]oxazin-3(4H)-one and the modestly divergent 1,3-dimethyl-1H-benzo[d]imidazol-2(3H)-one and 1-(indolin-1-yl)ethanone heterocycles.

TABLE 1

SAR of selected N-(3,4-dimethylphenyl)arylsulfonamides

| # | $Z^1$ | hPK, M2 $AC_{50}$ (μM) | hPK, M2 Max. Res.[a] |
|---|---|---|---|
| 4 | 3,4-dihydroquinolin-2(1H)-one-6-sulfonamide | 0.65 | 104% |
| 5 | indolin-2-one-6-sulfonamide | 14.5 | 130% |
| 6 | 4,5-dihydro-1H-benzo[b]azepin-2(3H)-one-7-sulfonamide | 18.0 | 66% |
| 7 | 2H-benzo[b][1,4]oxazin-3(4H)-one-6-sulfonamide | 20.0 | 93% |
| 8 | 4-methyl-2H-benzo[b][1,4]oxazin-3(4H)-one-6-sulfonamide | 0.92 | 120% |
| 9 | 1H-benzo[d]imidazol-2(3H)-one-5-sulfonamide | 21.0 | 59% |
| 10 | 1,3-dimethyl-1H-benzo[d]imidazol-2(3H)-one-5-sulfonamide | 1.8 | 100% |
| 11 | 1-(indolin-1-yl)ethanone-5-sulfonamide | 1.8 | 65% |
| 12 | 1-methyl-1H-indole-5-sulfonamide | 20.0 | 40% |

[a]Max. Res. value represents the % activation at 57 μM of compound. Each value is the mean with standard deviation from three replicate experiments.

The next examination involved alterations to the 3,4-dimethylaniline moiety and are detailed in Table 2. While the 3,4-dimethylaniline moiety was among the most potent analogues, the 3-chlorophenyl derivative (compound 13) possessed an equal degree of potency and maximum response. Selected SAR trends were noticed in this series including the positive effect of substitutions at the meta position relative to the ortho and para positions (for instance, see the values for fluoro substitution within compounds 16, 23 and 26).

TABLE 2

SAR of selected 2-oxo-N-aryl-1,2,3,4-tetrahydroquinoline-6-sulfonamide

| # | R″ | hPK, M2 AC$_{50}$ (μM) | hPK, M2 Max. Res.[a] |
|---|---|---|---|
| 4 | 3,4-dimethylphenyl | 0.65 | 104% |
| 13 | 3-chlorophenyl | 0.65 | 100% |
| 14 | meta-tolyl | 1.2 | 99% |
| 15 | 3-methoxyphenyl | 3.2 | 91% |
| 16 | 3-fluorophenyl | 1.8 | 93% |
| 17 | 3-trifluoromethylphenyl | 13 | 96% |
| 18 | biphenyl-3-yl | 14 | 13% |
| 19 | pyridin-3-yl | 23 | 36% |
| 20 | 4-chlorophenyl | 3.2 | 94 |
| 21 | para-tolyl | 4.1 | 110 |
| 22 | 4-methoxyphenyl | 36 | 47% |
| 23 | 4-fluorophenyl | 10 | 99% |
| 24 | ortho-tolyl | 3.9 | 96% |
| 25 | 2-methoxyphenyl | 21 | 60% |
| 26 | 2-fluorophenyl | 7.3 | 85% |
| 27 | naphthalen-2-yl | 2.9 | 87% |
| 28 | naphthalen-1-yl | 10 | 101% |
| 29 | 2,3-dihydrobenzo[b][1,4]dioxin-6-yl | 16 | 86% |
| 30 | benzyl | 14 | 25% |

[a]Max. Res. value represents the % activation at 57 μM of compound. Each value is the mean with standard deviation from three replicate experiments.

The 6-position (by IUPAC nomenclature rules) in the 2H-benzo[b][1,4]oxazin-3(4H)-one heterocycle was examined (compounds 37-40). In general, this related position resulted in analogues with good potency and maximum response values (see Table 3). Increased size, however, was less effective as demonstrated by the piperidine analogue 34 and the aryl substituted analogue 40. Amine substitutions provided several analogues with good potency including the NHMe-containing derivative compound 33. The N(Me)$_2$-containing compounds 32 and 36 were both potent and fully activated the enzyme.

TABLE 3

SAR of selected N-(3,4-dimethylphenyl)arylsulfonamides

| # | R$^1$ | hPK, M2 AC$_{50}$ (μM) | hPK, M2 Max. Res.[a] |
|---|---|---|---|
| 4 | H | 0.65 | 104% |
| 31 | F | 0.92 | 115% |
| 32 | N(Me)$_2$ | 0.52 | 106% |
| 33 | NHMe | 0.16 | 53% |
| 34 | 1-piperidine | 15 | 57% |
| 35 | Cl | 0.26 | 104% |
| 36 | N(Me)$_2$ | 0.46 | 110% |
| 37 | Cl | 0.58 | 95% |
| 38 | Br | 18 | 103% |
| 39 | Me | 1.2 | 106% |
| 40 | phenyl | 20.6 | 36% |

[a]Max. Res. value represents the % activation at 57 μM of compound. Each value is the mean with standard deviation from three replicate experiments.

Compounds 41-73 were also tested. The results are in Table 4.

TABLE 4

| Compound | Structure | AC$_{50}$ (μM) | Max. Res. |
|---|---|---|---|
| 41 | 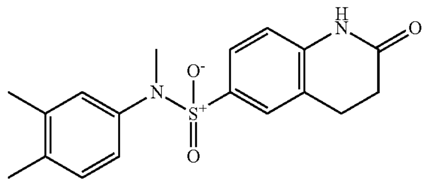 [SMILES: Cc1ccc(N(C)[S+](=O)([O-])c2ccc3c(c2)CCC(=O)N3)cc1C] | 23.09 | 36.00 |
| 42 | 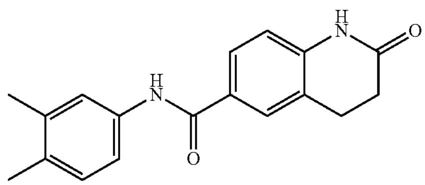 [SMILES: Cc1ccc(NC(=O)c2ccc3c(c2)CCC(=O)N3)cc1C] | 40 | 5 |
| 43 | 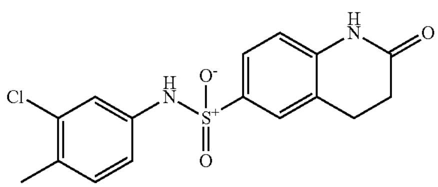 [SMILES: Cc1ccc(N[S+](=O)([O-])c2ccc3c(c2)CCC(=O)N3)cc1Cl] | 0.26 | 122.38 |
| 44 | 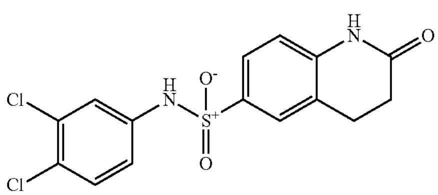 [SMILES: O=C1CCc2cc([S+](=O)([O-])Nc3ccc(Cl)c(Cl)c3)ccc2N1] | 2.59 | 126.17 |
| 45 | 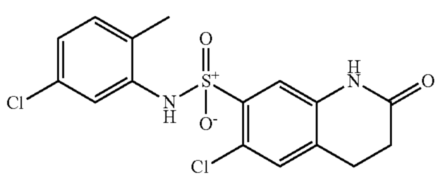 [SMILES: Cc1ccc(Cl)cc1N[S+](=O)([O-])c1cc2c(cc1Cl)CCC(=O)N2] | 2.91 | 108.88 |
| 46 | 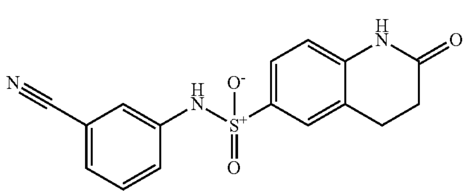 [SMILES: N#Cc1cccc(N[S+](=O)([O-])c2ccc3c(c2)CCC(=O)N3)c1] | 9.19 | 97.00 |
| 47 | 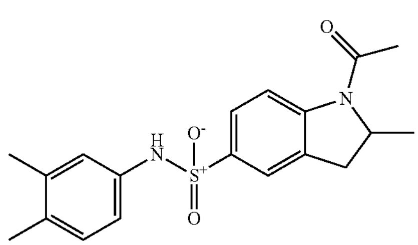 | 18.34 | 111.76 |

TABLE 4-continued

| Compound | Structure | AC$_{50}$ (μM) | Max. Res. |
|---|---|---|---|
| 48 | 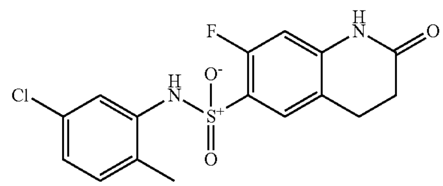 [SMILES: Cc1ccc(Cl)cc1N[S+](=O)([O-])c1cc2c(cc1F)NC(=O)CC2] | 4.61 | 94.62 |
| 49 | 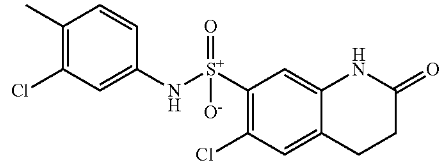 [SMILES: Cc1ccc(N[S+](=O)([O-])c2cc3c(cc2Cl)CCC(=O)N3)cc1Cl] | 0.65 | 111.72 |
| 50 | 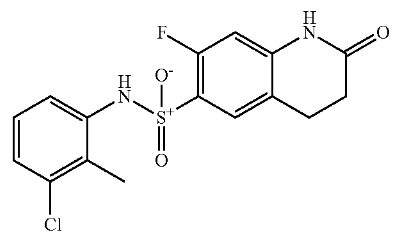 [SMILES: Cc1c(Cl)cccc1N[S+](=O)([O-])c1cc2c(cc1F)NC(=O)CC2] | 2.59 | 117.55 |
| 51 | 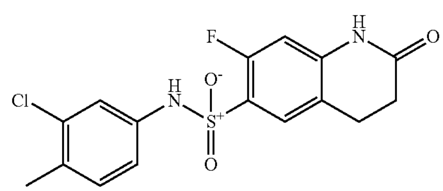 [SMILES: Cc1ccc(N[S+](=O)([O-])c2cc3c(cc2F)NC(=O)CC3)cc1Cl] | 0.12 | 102.49 |
| 52 | 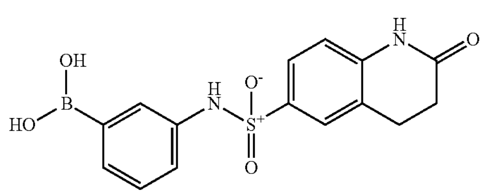 [SMILES: O=C1CCc2cc([S+](=O)([O-])Nc3cccc(B(O)O)c3)ccc2N1] | 0.82 | 99.32 |
| 53 | 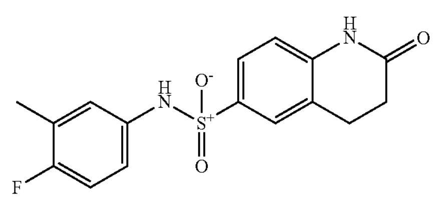 [SMILES: Cc1cc(N[S+](=O)([O-])c2ccc3c(c2)CCC(=O)N3)ccc1F] | 0.37 | 121.19 |
| 54 | 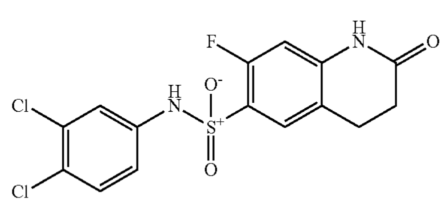 [SMILES: O=C1CCc2cc([S+](=O)([O-])Nc3ccc(Cl)c(Cl)c3)c(F)cc2N1] | 3.66 | 108.94 |
| 55 | 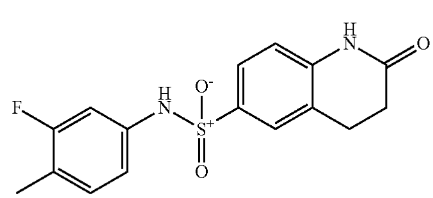 [SMILES: Cc1ccc(N[S+](=O)([O-])c2ccc3c(c2)CCC(=O)N3)cc1F] | 0.46 | 131.37 |

TABLE 4-continued

| Compound | Structure | AC$_{50}$ (μM) | Max. Res. |
|---|---|---|---|
| 56 | 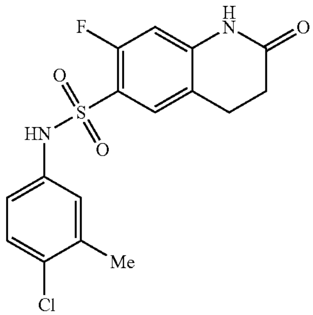 [SMILES: Cc1cc(NS(=O)(=O)c2cc3c(cc2F)NC(=O)CC3)ccc1Cl] | 0.82 | 94.23 |
| 57 | 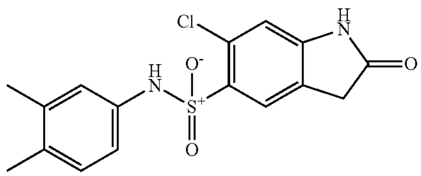 [SMILES: Cc1ccc(N[S+](=O)([O-])c2cc3c(cc2Cl)NC(=O)C3)cc1C] | 0.92 | 107.73 |
| 58 | 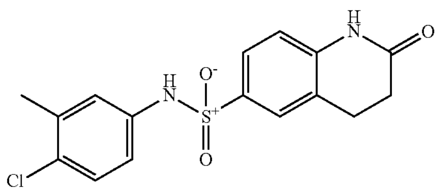 [SMILES: Cc1cc(N[S+](=O)([O-])c2ccc3c(c2)CCC(=O)N3)ccc1Cl] | 0.41 | 96.45 |
| 59 | 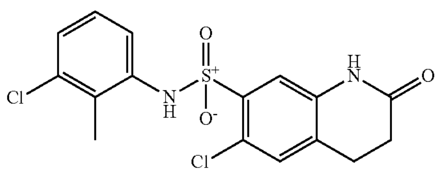 [SMILES: Cc1c(Cl)cccc1N[S+](=O)([O-])c1cc2c(cc1Cl)CCC(=O)N2] | 1.16 | 109.46 |
| 60 | 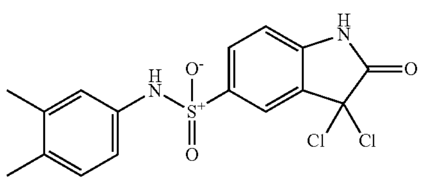 [SMILES: Cc1ccc(N[S+](=O)([O-])c2ccc3c(c2)C(Cl)(Cl)C(=O)N3)cc1C] | 10.31 | 117.30 |
| 61 | 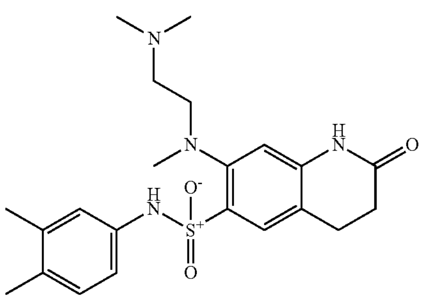 [SMILES: Cc1ccc(N[S+](=O)([O-])c2cc3c(cc2N(C)CCN(C)C)NC(=O)CC3)cc1C] | 5.84 | 70.48 |
| 62 | 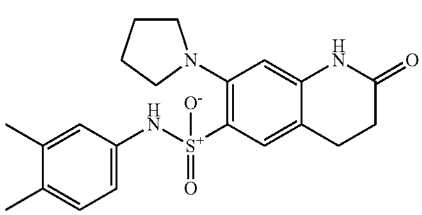 [SMILES: Cc1ccc(N[S+](=O)([O-])c2cc3c(cc2N2CCCC2)NC(=O)CC3)cc1C] | 0.46 | 124.25 |

TABLE 4-continued

| Compound | Structure | AC$_{50}$ (μM) | Max. Res. |
|---|---|---|---|
| 63 | 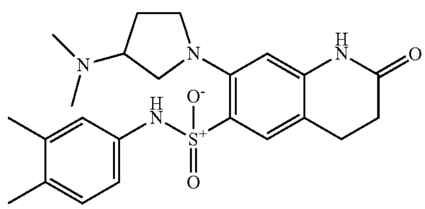 [SMILES: Cc1ccc(N[S+](=O)([O-])c2cc3c(cc2N2CCC(N(C)C)C2)NC(=O)CC3)cc1C] | 8.19 | 102.12 |
| 64 | 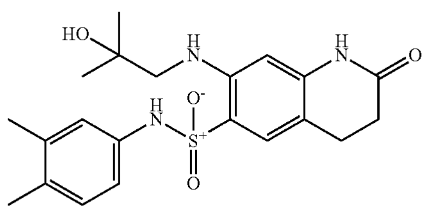 [SMILES: Cc1ccc(N[S+](=O)([O-])c2cc3c(cc2NCC(C)(C)O)NC(=O)CC3)cc1C] | 1.83 | 100.38 |
| 65 | 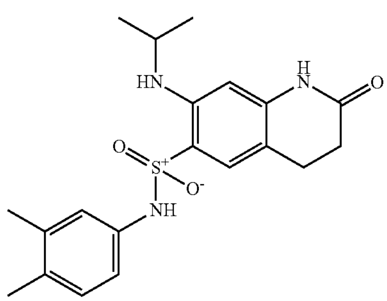 [SMILES: Cc1ccc(N[S+](=O)([O-])c2cc3c(cc2NC(C)C)NC(=O)CC3)cc1C] | 0.32 | 105.86 |
| 66 | 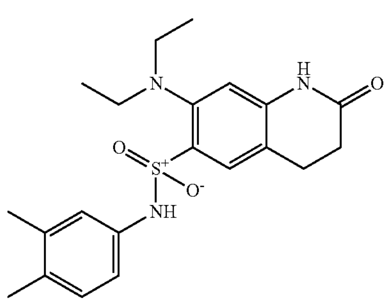 [SMILES: CCN(CC)c1cc2c(cc1[S+](=O)([O-])Nc1ccc(C)c(C)c1)CCC(=O)N2] | 7.24 | 110.76 |
| 67 | 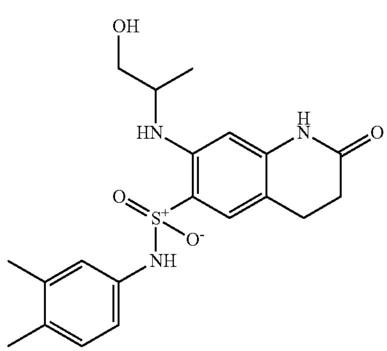 [SMILES: Cc1ccc(N[S+](=O)([O-])c2cc3c(cc2NC(C)CO)NC(=O)CC3)cc1C] | 0.11 | 110.43 |

TABLE 4-continued
| Compound | Structure | AC$_{50}$ (μM) | Max. Res. |
|---|---|---|---|
| 68 | 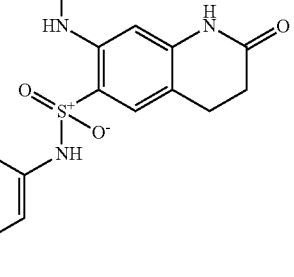 | 0.09 | 131.05 |
| 69 | 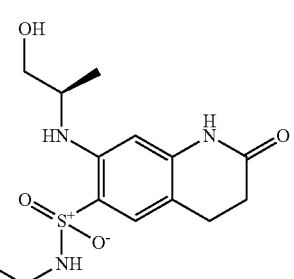 | 0.37 | 87.70 |
| 70 | 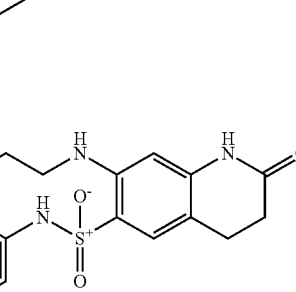 | 0.09 | 110.67 |
| 71 | 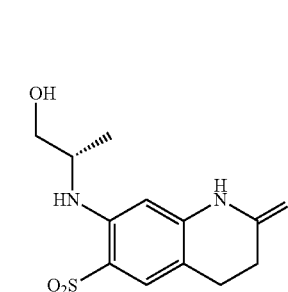 | 0.08 | 124 |

TABLE 4-continued

| Compound | Structure | AC$_{50}$ (μM) | Max. Res. |
|---|---|---|---|
| 72 | 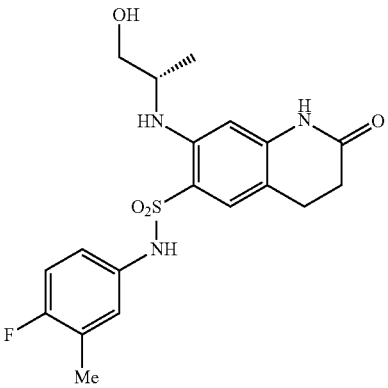 [SMILES: Cc1cc(NS(=O)(=O)c2cc3c(cc2N[C@@H](C)CO)NC(=O)CC3)ccc1F] | 0.27 | 99 |
| 73 | 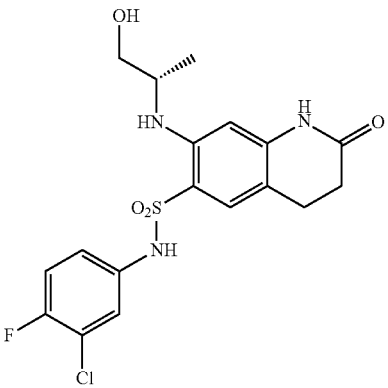 [SMILES: C[C@@H](CO)Nc1cc2c(cc1S(=O)(=O)Nc1ccc(F)c(Cl)c1)CCC(=O)N2] | 0.14 | 95 |

The same assay system was utilized to examine the activity of compound 4 and all related analogs versus PKL, PKM1 and PKR pyruvate kinase isoforms. No activity for any of the compounds were found against PKL, PKM1, or PKR.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of the formula:
wherein R is H;
wherein L is SO$_2$ or CO;
wherein R' is

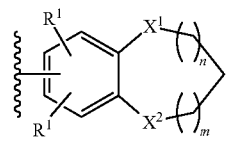

wherein X$^1$ is NR$^6$ or N-acetyl and X$^2$ is O or CR$^7$R$^8$;
wherein any CH$_2$—CH$_2$ moiety within the ring containing X$^1$ and X$^2$ is optionally replaced with a CH=CH moiety;

wherein any NR—CH$_2$ moiety within the ring containing X$^1$ and X$^2$ is optionally replaced with a N=CH moiety;

wherein one methylene of the ring containing X$^1$ and X$^2$ is replaced by a carbonyl;

wherein n and m are each individually 0, 1, or 2, and wherein n+m is 0 to 2;

wherein each R$^1$ is individually H, halogen, alkyl, alkoxyl, NH$_2$, NH—(C$_1$-C$_4$)alkyl, N—(C$_1$-C$_4$)alkyl-(C$_1$-C$_4$)alkyl, aryl, heteroaryl, cyclyl, or heterocyclyl, each of which other than halogen and NH$_2$ is optionally substituted with one or more substituents selected from the group consisting of NH$_2$, OH, NH—(C$_1$-C$_4$)alkyl and N—(C$_1$-C$_4$)alkyl-(C$_1$-C$_4$)alkyl;

wherein R$^6$ is H, alkyl, alkylcarboxy, aryl, heteroaryl, cyclyl, or heterocyclyl, each of which is optionally substituted with one or more substituents selected from the group consisting of NH$_2$, OH, NH—(C$_1$-C$_4$)alkyl and N—(C$_1$-C$_4$)alkyl-(C$_3$-C$_4$)alkyl; and wherein R$^7$ and R$^8$ are each individually H, alkoxyl, NH$_2$, NH—(C$_1$-C$_4$)alkyl, N—(C$_1$-C$_4$)alkyl-(C$_1$-C$_4$)alkyl, aryl, heteroaryl, cyclyl, or heterocyclyl, each of which other than halogen and NH$_2$ is optionally substituted with one or more substituents selected from the group consisting of NH$_2$, OH, NH—(C$_1$-C$_4$)alkyl and N—(C$_1$-C$_4$)alkyl-(C$_1$-C$_4$)alkyl;

wherein R" is phenyl, benzyl, pyridinyl, or naphthalenyl, the benzyl substituted with one or more substituents selected from the group consisting of C$_1$-C$_4$ alkyl, C$_1$-C$_4$ alkoxyl, cyano, alkylenedioxy, aryl, benzyl, B(OH)$_2$, and C$_1$-C$_4$ alkyl substituted with one or more halogens, and the pyridinyl, and naphthalenyl optionally substituted with one or more substituents selected from the group consisting of halogen, C$_1$-C$_4$ alkyl, C$_1$-C$_4$ alkoxyl, cyano, alkylenedioxy, aryl, benzyl, B(OH)$_2$, and C$_1$-C$_4$ alkyl substituted with one or more halogens, and the phenyl optionally substituted with one or more substituents selected from the group consisting of halogen, C$_1$-C$_4$ alkyl, cyano, alkylenedioxy, aryl, benzyl, B(OH)$_2$, and C$_1$-C$_4$ alkyl substituted with one or more halogens, or is phenyl fused with an aryl, a heteroaryl, a cyclyl, or a heterocyclyl, each of which is optionally substituted with one or more substituents selected from the group consisting of halogen, C$_1$-C$_4$ alkyl, C$_1$-C$_4$ alkoxyl, alkylenedioxy, aryl, heteroaryl, benzyl, and C$_1$-C$_4$ alkyl substituted with one or more halogens; and with the proviso that the compound is not

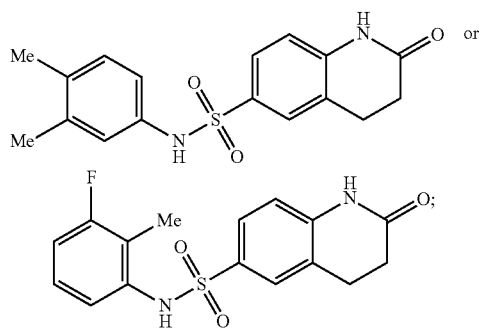

or a pharmaceutically acceptable salt thereof.

2. The compound or salt of claim 1, wherein one R$^1$ is H, F, Cl, Br, methyl, N(Me)$_2$, NHMe, 1-piperidinyl, 2-(dimethylamino)ethyl)(methyl)amino, pyrrolidin-1-yl, 3-(dimethylamino)pyrrolidin-1-yl, 2-hydroxy-2-methylpropylamino, isopropylamino, diethylamino, 1-hydroxypropan-2-ylamino, 2-hydroxyethylamino, or phenyl.

3. The compound or salt of claim 1, wherein R' is 3,4-dihydroquinolin-2(1H)-onyl, indolin-2-onyl, 4,5-dihydro-1H-benzo[b]azepin-2(3H)-onyl, 2H-benzo[b][1,4]oxazin-3(4H)-onyl, 4-methyl-2H-benzo[b][1,4]oxazin-3(4H)-onyl, -(indolin-1-yl)ethanonyl, 1-methyl-1H-indolyl, 1-acetyl-2-methylindolinyl, 7-((2-(dimethylamino)ethyl)(methyl)amino)-2-oxo-1,2,3,4-tetrahydroquinolinyl, 2-oxo-7-(pyrrolidin-1-yl)-1,2,3,4-tetrahydroquinolinyl, 7-(3-(dimethylamino)pyrrolidin-1-yl)-2-oxo-1,2,3,4-tetrahydroquinolinyl, 7-(2-hydroxy-2-methylpropylamino)-2-oxo-1,2,3,4-tetrahydroquinolinyl, 7-(isopropylamino)-2-oxo-1,2,3,4-tetrahydroquinolinyl, 7-(diethylamino)-2-oxo-1,2,3,4-tetrahydroquinolinyl, 7-(2-hydroxyethylamino)-2-oxo-1,2,3,4-tetrahydroquinolinyl, 7-(1-hydroxypropan-2-ylamino)-2-oxo-1,2,3,4-tetrahydroquinolinyl, (S)-7-(1-hydroxypropan-2-ylamino)-2-oxo-1,2,3,4-tetrahydroquinolinyl, or (R)-7-(1-hydroxypropan-2-ylamino)-2-oxo-1,2,3,4-tetrahydroquinolinyl.

4. The compound or salt of claim 1, wherein R" is

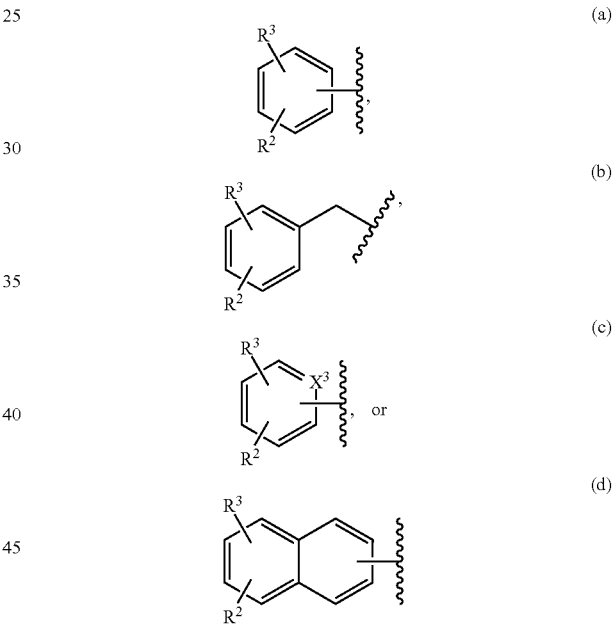

wherein X$^3$ is N, the NR-L moiety is linked to a C of the ring containing X$^3$;

wherein for (a), R$^2$ and R$^3$ are each individually H, halogen, C$_1$-C$_4$ alkyl, cyano, B(OH)$_2$, phenyl, C$_1$-C$_4$ alkyl substituted with one or more halogens, or taken together form alkylenedioxyl, for (b), R$^2$ is C$_1$-C$_4$ alkyl, C$_1$-C$_4$ alkoxyl, cyano, B(OH)$_2$, phenyl, or C$_1$-C$_4$ alkyl substituted with one or more halogens, R$^3$ is H, C$_1$-C$_4$ alkyl, C$_1$-C$_4$ alkoxyl, cyano, B(OH)$_2$, phenyl, C$_1$-C$_4$ alkyl substituted with one or more halogens, or R$^2$ and R$^3$ are taken together to form alkylenedioxyl, for (c) and (d), R$^2$ and R$^3$ are each individually H, halogen, C$_1$-C$_4$ alkyl, C$_1$-C$_4$ alkoxyl, cyano, B(OH)$_2$, phenyl, C$_1$-C$_4$ alkyl substituted with one or more halogens, or taken together form alkylenedioxyl.

5. The compound or salt of claim 4, wherein R" is (a), and R$^2$ and R$^3$ are each individually F, Cl, Br, methyl, cyano, trifluoromethyl, phenyl, or B(OH)$_2$, or taken together form alkylenedioxyl, or is (c) or (d) and R$^2$ and R$^3$ are each individually F, Cl, Br, methyl, methoxy, cyano, trifluoromethyl, phenyl, or B(OH)$_2$, or taken together form alkylenedioxyl.

6. The compound or salt of claim 1, wherein R" is 3,4-dimethylphenyl, 3-chlorophenyl, meta-tolyl, 3-fluorophenyl, 3-trifluoromethylphenyl, biphenyl-3-yl, pyridine-3-yl, 4-chlorophenyl, para-tolyl, 4-fluorophenyl, ortho-tolyl, 2-fluorophenyl, naphthalen-2-yl, naphthalen-1-yl, 2,3-dihydrobenzo[b][1,4]dioxin-6-yl, 3-chloro-4-methylphenyl, 3,4-dichlorophenyl, 5-chloro-2-methylphenyl, 3-cyanophenyl, 3-chloro-2-methylphenyl,

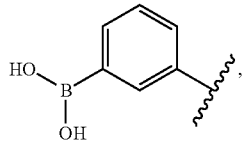

4-fluoro-3-methylphenyl, 3-fluoro-4-methylphenyl, 4-chloro-3-methylphenyl, or 3-chloro-4-fluorophenyl.

7. The compound or salt of claim 1, wherein the compound is a compound of formula (II):

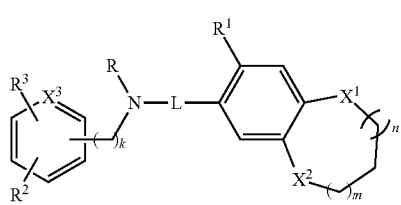

(II)

wherein R is H;
wherein L is SO$_2$ or CO;
wherein X$^1$ is NR$^6$ or N-acetyl and X$^2$ is O or CR$^7$R$^8$;
wherein X$^3$ is N or CH wherein when X is N, the NR-L moiety is linked to a C of the ring containing X$^3$;
wherein any CH$_2$—CH$_2$ moiety within the ring containing X$^1$ and X$^2$ is optionally replaced with a CH=CH moiety;
wherein any NH—CH$_2$ moiety within the ring containing X$^1$ and X$^2$ is optionally replaced with a N=CH moiety;
wherein one methylene of the ring containing X$^1$ and X$^2$ is replaced by a carbonyl;
wherein n and m are each individually 0, 1, or 2, and wherein n m is 0 to 2;
wherein k is 0 or 1,
wherein R$^1$ is H, halogen, alkyl, alkoxyl, NH$_2$, NH—(C$_1$-C$_4$)alkyl, N—(C$_1$-C$_4$)alkyl-(C$_1$-C$_4$)alkyl, aryl, heteroaryl, cyclyl, heterocyclyl, each of which other than halogen and NH$_2$ is optionally substituted with one or more substituents selected from the group consisting of NH$_2$, OH, NH—(C$_1$-C$_4$)alkyl and N—(C$_1$-C$_4$)alkyl-(C$_1$-C$_4$)alkyl;
wherein R$^2$ and R$^3$ are each individually H, halogen, C$_1$-C$_4$ alkyl, cyano, B(OH)$_2$, phenyl, C$_1$-C$_4$ alkyl substituted with one or more halogens, or taken together form alkylenedioxy or phenyl fused to a CH:CH moiety of the ring containing X,
wherein when X$^3$ is CH, k is I, and R$^2$ is H, R$^3$ is not H;

wherein R$^6$ is H, alkyl, alkylcarboxy, aryl, heteroaryl, cyclyl, or heterocyclyl, each of which is optionally substituted with one or more substituents selected from the group consisting of NH$_2$, OH, NH—(C$_1$-C$_4$)alkyl and N—(C$_1$-C$_4$)alkyl-(C$_1$-C$_4$)alkyl; and
wherein R$^7$ and R$^8$ are each individually H, alkyl, alkoxyl, NH$_2$, N—(C$_1$-C$_4$)alkyl-(C$_1$-C$_4$)alkyl, aryl, heteroaryl, cyclyl, or heterocyclyl, each of which other than halogen and NH$_2$ is optionally substituted with one or more substituents selected from the group consisting of NH$_2$, OH, NH—(C$_1$-C$_4$)alkyl and N—(C$_1$-C$_4$)alkyl-(C$_1$-C$_4$) alkyl.

8. The compound or salt of claim 7, wherein R$^1$ is H, F, Cl, Br, methyl, N(Me)$_2$, 1-piperidinyl, 2-(dimethylamino) ethyl)(methyl)amino, pyrrolidin-1-yl, 3-(dimethylamino) pyrrolidin-1-yl, 2-hydroxy-2-methylpropylamino, isopropylamino, diethylamino, 1-hydroxypropan-2-ylamino, 2-hydroxyethylamino, or phenyl.

9. The compound or salt of claim 7, wherein

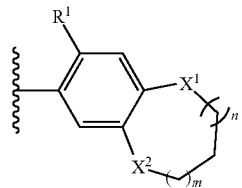

is 3,4-dihydroquinolin-2(1H)-onyl, H-benzo[b]azepin-2(3H)-onyl, 2H-benzo[b][1,4]oxazin-3(4H)-onyl, 4-methyl-2H-benzo[b][1,4]oxazin-3(4H)-onyl, 1-(indolin-1-yl)ethanonyl, 1-methyl-1H-indolyl, 1-acetyl-2-methylindolinyl, 7-((2-(dimethylamino)ethyl)(methyl)amino)-2-oxo-1,2,3,4-tetrahydroquinolinyl, 2-oxo-7-(pyrrolidin-1-yl)-1,2,3,4-tetrahydroquinolinyl, 7-(3-(dimethylamino)pyrrolidin-1-yl)-2-oxo-1,2,3,4-tetrahydroquinolinyl, 7-(2-hydroxy-2-methylpropylamino)-2-oxo-1,2,3,4-tetrahydroquinolinyl, 7-(isopropylamino)-2-oxo-1,2,3,4-tetrahydroquinolinyl, 7-(diethylamino)-2-oxo-1,2,3,4-tetrahydroquinolinyl, 7-(2-hydroxyethylamino)-2-oxo-1,2,3,4-tetrahydroquinolinyl, 7-(1-hydroxypropan-2-ylamino)-2-oxo-1,2,3,4-tetrahydroquinolinyl, (S)-7-(1-hydroxypropan-2-ylamino)-2-oxo-1,2,3,4-tetrahydroquinolinyl, or (R)-7-(1-hydroxypropan-2-ylamino)-2-oxo-1,2,3,4-tetrahydroquinolinyl.

10. The compound or salt of claim 7, wherein R$^2$ and R$^3$ are each individually F, Cl, Br, methyl, cyano, trifluoromethyl, phenyl, B(OH)$_2$, or taken together form alkylenedioxyl or phenyl fused to a CH:CH moiety of the ring containing X$^3$.

11. The compound or salt of claim 7, wherein

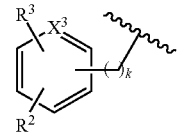

is 3,4-dimethylphenyl, 3-chlorophenyl, meta-tolyl, 3-fluorophenyl, 3-trifluoromethylphenyl, pyridin-3-yl, 4-chlorophenyl, para-tolyl, 4-fluorophenyl, ortho-tolyl, 2-fluorophenyl, naphthalen-2-yl, naphthalen-1-yl, 2,3-dihydrobenzo[b][1,4]dioxin-6-yl, 3-chloro-4-methylphenyl, 3,4-dichlorophenyl, 5-chloro-2-methylphenyl, 3-cyanophenyl, 3-chloro-2-methylphenyl,

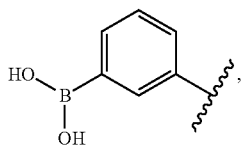

4-fluoro-3-methylphenyl, 3-fluoro-4-methylphenyl, 4-chloro-3-methylphenyl, 3-chloro-4-fluorophenyl.

12. A compound selected from
N-(3,4-dimethylphenyl)-2-oxoindoline-5-sulfonamide,
N-(3,4-dimethylphenyl)-2-oxo-2,3,4,5-tetrahydro-1H-benzo[b]azepine-7-sulfonamide,
N-(3,4-dimethylphenyl)-3-oxo-3,4-dihydro-2H-benzo[b][1,4]oxazine-6-sulfonamide,
N-(3,4-dimethylphenyl)-4-methyl-3-oxo-3,4-dihydro-2H-benzo[b][1,4]oxazine-6-sulfonamide,
N-(3,4-dimethylphenyl)-2-oxo-2,3-dihydro-1H-benzo[d]imidazole-5-sulfonamide,
N-(3,4-dimethylphenyl)-1,3-dimethyl-2-oxo-2,3-dihydro-1H-benzo[d]imidazole-5-sulfonamide,
1-acetyl-N-(3,4-dimethylphenyl)indoline-5-sulfonamide,
N-(3,4-dimethylphenyl)-1-methyl-1H-indole-5-sulfonamide,
N-(3-chlorophenyl)-2-oxo-1,2,3,4-tetrahydroquinoline-6-sulfonamide,
2-oxo-N-m-tolyl-1,2,3,4-tetrahydroquinoline-6-sulfonamide,
N-(3-methoxyphenyl)-2-oxo-1,2,3,4-tetrahydroquinoline-6-sulfonamide,
N-(3-fluorophenyl)-2-oxo-1,2,3,4-tetrahydroquinoline-6-sulfonamide,
2-oxo-N-(3-(trifluoromethyl)phenyl)-1,2,3,4-tetrahydroquinoline-6-sulfonamide,
N-(biphenyl-3-yl)-2-oxo-1,2,3,4-tetrahydroquinoline-6-sulfonamide,
2-oxo-N-(pyridin-3-yl)-1,2,3,4-tetrahydroquinoline-6-sulfonamide,
N-(4-chlorophenyl)-2-oxo-1,2,3,4-tetrahydroquinoline-6-sulfonamide,
2-oxo-N-p-tolyl-1,2,3,4-tetrahydroquinoline-6-sulfonamide,
N-(4-methoxyphenyl)-2-oxo-1,2,3,4-tetrahydroquinoline-6-sulfonamide,
N-(4-fluorophenyl)-2-oxo-1,2,3,4-tetrahydroquinoline-6-sulfonamide,
2-oxo-N-o-tolyl-1,2,3,4-tetrahydroquinoline-6-sulfonamide,
N-(2-methoxyphenyl)-2-oxo-1,2, 3,4-tetrahydroquinoline-6-sulfonamide,
N-(2-fluorophenyl)-2-oxo-1,2,3,4-tetrahydroquinoline-6-sulfonamide,
N4(naphthalen-2-yl)-2-oxo-1,2,3,4-tetrahydroquinoline-6-sulfonamide,
N-(naphthalen-1-yl)-2-oxo-1,2,3,4-tetrahydroquinoline-6-sulfonamide,
N-(2,3-dihydrobenzo[b][1,4]dioxin-6-yl)-2-oxo-1,2,3,4-tetrahydroquinoline-6-sulfonamide,
N-benzyl-2-oxo-1,2,3,4-tetrahydroquinoline-6-sulfonamide,
N-(3,4-dimethylphenyl)-7-fluoro-2-oxo-1,2,3,4-tetrahydroquinoline-6-sulfonamide,
7-(dimethylamino)-N-(3,4-dimethylphenyl)-2-oxo-1,2,3,4-tetrahydroquinoline-6-sulfonamide,
N-(3,4-dimethylphenyl)-7-(methylamino)-2-oxo-1,2,3,4-tetrahydroquinoline-6-sulfonamide,
N-(3,4-dimethylphenyl)-2-oxo-7-(piperidin-1-yl)-1,2,3,4-tetrahydroquinoline-6-sulfonamide,
6-chloro-N-(3,4-dimethylphenyl)-2-oxo-1,2,3,4-tetrahydroquinoline-7-sulfonamide,
6-(dimethylamino)-N-(3,4-dimethylphenyl)-2-oxo-1,2,3,4-tetrahydroquinoline-7-sulfonamide,
6-chloro-N-(3,4-dimethylphenyl)-3-oxo-3,4-dihydro-2H-benzo[b][1,4]oxazine-7-sulfonamide,
6-bromo-N-(3,4-dimethylphenyl)-3-oxo-3,4-dihydro-2H-benzo[b][1,4]oxazine-7-sulfonamide,
N-(3,4-dimethylphenyl)-6-methyl-3-oxo-3,4-dihydro-2H-benzo[b][1,4]oxazine-7-sulfonamide,
N-(3,4-dimethylphenyl)-3-oxo-6-phenyl-3,4-dihydro-2H-benzo[b][1,4]oxazine-7-sulfonamide,
N-(3,4-dimethylphenyl)-N-methyl-2-oxo-1,2,3,4-tetrahydroquinoline-6-sulfonamide,
N-(3,4-dimethylphenyl)-2-oxo-1,2,3,4-tetrahydroquinoline-6-carboxamide,
N-(3-chloro-4-methylphenyl)-2-oxo-1,2,3,4-tetrahydroquinoline-6-sulfonamide,
N-(3,4-dichlorophenyl)-2-oxo-1,2,3,4-tetrahydroquinoline-6-sulfonamide,
6-chloro-N-(5-chloro-2-methylphenyl)-2-oxo-1,2,3,4-tetrahydroquinoline-7-sulfonamide,
N-(3-cyanophenyl)-2-oxo-1,2,3,4-tetrahydroquinoline-6-sulfonamide,
1-acetyl-N-(3,4-dimethylphenyl)-2-methylindoline-5-sulfonamide,
N-(5-chloro-2-methylphenyl)-7-fluoro-2-oxo-1,2,3,4-tetrahydroquinoline-6-sulfonamide,
6-chloro-N-(3-chloro-4-methylphenyl)-2-oxo-1,2, 3,4-tetrahydroquinoline-7-sulfonamide,
N-(3-chloro-2-methylphenyl)-7-fluoro-2-oxo-1,2,3,4-tetrahydroquinoline-6-sulfonamide,
N-(3-chloro-4-methylphenyl)-7-fluoro-2-oxo-1,2,3,4-tetrahydroquinoline-6-sulfonamide,
3-(2-oxo-1,2,3,4-tetrahydroquinoline-6-sulfonamido)phenylboronic acid,
N-(4-fluoro-3-methylphenyl)-2-oxo-1,2,3,4-tetrahydroquinoline-6-sulfonamide,
N-(3,4-dichlorophenyl)-7-fluoro-2-oxo-1,2,3,4-tetrahydroquinoline-6-sulfonamide,
N-(3-fluoro-4-methylphenyl)-2-oxo-1,2,3,4-tetrahydroquinoline-6-sulfonamide,
N-(4-chloro-3-methylphenyl)-7-fluoro-2-oxo-1,2,3,4-tetrahydroquinoline-6-sulfonamide,
6-chloro-N-(3,4-dimethylphenyl)-2-oxoindoline-5-sulfonamide,
N-(4-chloro-3-methylphenyl)-2-oxo-1,2,3,4-tetrahydroquinoline-6-sulfonamide,
6-chloro-N-(3-chloro-2-methylphenyl)-2-oxo-1,2,3,4-tetrahydroquinoline-7-sulfonamide,
3,3-dichloro-N-(3,4-dimethylphenyl)-2-oxoindoline-5-sulfonamide,
7-((2-(dimethylamino)ethyl)(methyl)amino)-N-(3,4-dimethylphenyl)-2-oxo-1,2,3,4-tetrahydroquinoline-6-sulfonamide,
N-(3,4-dimethylphenyl)-2-oxo-7-(pyrrolidin-1-yl)-1,2,3,4-tetrahydroquinoline-6-sulfonamide,
7-(3-(dimethylamino)pyrrolidin-1-yl)-N-(3,4-dimethylphenyl)-2-oxo-1,2,3,4-tetrahydroquinoline-6-sulfonamide,
N-(3,4-dimethylphenyl)-7-(2-hydroxy-2-methylpropylamino)-2-oxo-1,2,3,4-tetrahydroquinoline-6-sulfonamide,
N-(3,4-dimethylphenyl)-7-(isopropylamino)-2-oxo-1,2,3,4-tetrahydroquinoline-6-sulfonamide, 7-(diethylamino)-N-(3,4-dimethylphenyl)-2-oxo-1,2,3,4-tetrahydroquinoline-6-sulfonamide, N-(3,4-dimethylphenyl)-7-(1-hydroxypropan-2-ylamino)-2-oxo-1,2,3,4-tetrahydroquinoline-6-sulfonamide, (S)—N-(3,4-dimethylphenyl)-7-(1-hydroxypropan-2-ylamino)-2-oxo-1,2,3,4-tetrahydroquinoline-6-sulfonamide, (R)—N-(3,4-dimethylphenyl)-7-(1-hydroxypropan-2-ylamino)-2-oxo-1,2,3,4-tetrahydroquinoline-6-sulfonamide, N-(3,4-dimethylphenyl)-7-(2-hydroxyethylamino)-2-oxo-1,2,3,4-tetrahydroquinoline-6-sulfonamide, (S)—N-(3-chloro-4-methylphenyl)-7-(1-hydroxypropan-2-ylamino)-2-oxo-1,2,3,4-tetrahydroquinoline-6-sulfonamide, (S)—N-(4-fluoro-3-methylphenyl)-7-(1-hydroxypropan-2-ylamino)-2-oxo-1,2,3,4-tetrahydroquinoline-6-sulfonamide, and (S)—N-(3-chloro-4-fluorophenyl)-7-(1-hydroxypropan-2-ylamino)-2-oxo-1,2,3,4-tetrahydroquinoline-6-sulfonamide, or a pharmaceutically acceptable salt thereof.

13. The compound or salt of claim 12, wherein the compound is (S)—N-(3-chloro-4-methylphenyl)-7-(1-hydroxypropan-2-ylamino)-2-oxo-1,2,3,4-tetrahydroquinoline-6-sulfonamide.

14. A pharmaceutical composition comprising a compound or salt according to claim 1, and a pharmaceutically acceptable carrier.

15. A method of inhibiting tumor cell growth or inhibiting cell proliferation responsive to activation of human PK-M2 comprising administering to a patient in need thereof a therapeutically effective amount of a compound or salt according to claim 1 or a pharmaceutical composition of claim 14.

16. The method according to claim 15, wherein the tumor cell growth or cell proliferation responsive to activation of human PK-M2 is cancer.

17. The method according to claim 16, wherein the cancer is leukemia, polycythemia vera, lymphoma, Waldenstrom's macroglobulinemia, multiple myeloma, heavy chain disease, sarcoma, or carcinoma.

18. The method according to claim 16, wherein the cancer is acute leukemia, acute lymphocytic leukemia, acute myeloid leukemia, acute myeloblastic leukemia, acute promyelocytic leukemia, acute myelomonocytic leukemia, acute monocytic leukemia, acute erythroleukemia, chronic leukemia, chronic myeloid leukemia, chronic lymphocytic leukemia, Hodgkin's disease, non-Hodgkin's disease, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, malignant mesothelioma, Ewing's tumor, leiomyosarcoma, rhabdomyosarcoma, alveolar rhabdomyosarcoma, colon cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, intrahepatic bile duct carcinoma, choriocarcinoma, seminoma, embryonal carcinoma, Wilm's tumor, cervical cancer, uterine cancer, testicular cancer, lung cancer, small cell lung carcinoma, urinary bladder cancer, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, retinoblastoma, bone cancer, brain cancer, cancer of the anus, cancer of the anal canal, cancer of the anorectum, cancer of the eye, cancer of the joints, cancer of the neck, cancer of the gallbladder, cancer of the pleura, cancer of the nose, cancer of the nasal cavity, cancer of the middle ear, cancer of the oral cavity, cancer of the vulva, esophageal cancer, gastrointestinal carcinoid tumor, hypopharynx cancer, kidney cancer, larynx cancer, liver cancer, nasopharynx cancer, non-small cell lung cancer, peritoneum cancer, omentum cancer, mesentery cancer, pharynx cancer, rectal cancer, renal cancer, small intestine cancer, soft tissue cancer, stomach cancer, thyroid cancer, or ureter cancer.

19. The method according to claim 18, wherein the cancer is liver cancer.

20. The compound of claim 12, wherein the compound is selected from

N-(3,4-dimethylphenyl)-2-oxoindoline-5-sulfonamide,

N-(3,4-dimethylphenyl)-2-oxo-2,3,4,5-tetrahydro-1H-benzo[b]azepine-7-sulfonamide, N-(3,4-dimethylphenyl)-3-oxo-3,4-dihydro-2H-benzo[b][1,4]oxazine-6-sulfonamide, N-(3,4-dimethylphenyl)-4-methyl-3-oxo-3,4-dihydro-2H-benzo[b][1,4]oxazine-6-sulfonamide, N-(3,4-dimethylphenyl)-2-oxo-2,3-dihydro-1H-benzo[d]imidazole-5-sulfonamide, N-(3,4-dimethylphenyl)-1,3-dimethyl-2-oxo-2,3-dihydro-1H-benzo[d]imidazole-5-sulfonamide, 1-acetyl-N-(3,4-dimethylphenyl)indoline-5-sulfonamide, N-(3,4-dimethylphenyl)-1-methyl-1H-indole-5-sulfonamide, N-(3-chlorophenyl)-2-oxo-1,2,3,4-tetrahydroquinoline-6-sulfonamide, 2-oxo-N-m-tolyl-1,2,3,4-tetrahydroquinoline-6-sulfonamide, N-(3-fluorophenyl)-2-oxo-1,2,3,4-tetrahydroquinoline-6-sulfonamide, 2-oxo-N-(3-(trifluoromethyl)phenyl)-1,2,3,4-tetrahydroquinoline-6-sulfonamide, N-(biphenyl-3-yl)-2-oxo-1,2,3,4-tetrahydroquinoline-6-sulfonamide, 2-oxo-N-(pyridin-3-yl)-1,2,3,4-tetrahydroquinoline-6-sulfonamide, N-(4-chlorophenyl)-2-oxo-1,2,3,4-tetrahydroquinoline-6-sulfonamide, 2-oxo-N-p-tolyl-1,2,3,4-tetrahydroquinoline-6-sulfonamide, N-(4-fluorophenyl)-2-oxo-1,2,3,4-tetrahydroquinoline-6-sulfonamide, 2-oxo-N-o-tolyl-1,2,3,4-tetrahydroquinoline-6-sulfonamide, N-(2-fluorophenyl)-2-oxo-1,2,3,4-tetrahydroquinoline-6-sulfonamide, N-(naphthalen-2-yl)-2-oxo-1,2,3,4-tetrahydroquinoline-6-sulfonamide, N-(naphthalen-1-yl)-2-oxo-1,2,3,4-tetrahydroquinoline-6-sulfonamide, N-(2,3-dihydrobenzo[b][1,4]dioxin-6-yl)-2-oxo-1,2,3,4-tetrahydroquinoline-6-sulfonamide, N-benzyl-2-oxo-1,2,3,4-tetrahydroquinoline-6-sulfonamide, N-(3,4-dimethylphenyl)-7-fluoro-2-oxo-1,2,3,4-tetrahydroquinoline-6-sulfonamide, 7-(dimethylamino)-N-(3,4-dimethylphenyl)-2-oxo-1,2,3,4-tetrahydroquinoline-6-sulfonamide, N-(3,4-dimethylphenyl)-7-(methylamino)-2-oxo-1,2,3,4-tetrahydroquinoline-6-sulfonamide,
N-(3,4-dimethylphenyl)-2-oxo-7-(piperidin-1-yl)-1,2,3,4-tetrahydroquinoline-6-sulfonamide,
6-chloro-N-(3,4-dimethylphenyl)-2-oxo-1,2,3,4-tetrahydroquinoline-7-sulfonamide,
6-(dimethylamino)-N-(3,4-dimethylphenyl)-2-oxo-1,2,3,4-tetrahydroquinoline-7-sulfonamide,
6-chloro-N-(3,4-dimethylphenyl)-3-oxo-3,4-dihydro-2H-benzo[b]1,4]oxazine-7-sulfonamide,
6-bromo-N-(3,4-dimethylphenyl)-3-oxo-3,4-dihydro-2H-benzo[b][1,4]oxazine-7-sulfonamide,
N-(3,4-dimethylphenyl)-6-methyl-3-oxo-3,4-dihydro-2H-benzo[b]1,4]oxazine-7-sulfonamide,
N-(3,4-dimethylphenyl)-3-oxo-6-phenyl-3,4-dihydro-2H-benzo[b][1,4]oxazine-7-sulfonamide,
N-(3,4-dimethylphenyl)-N-methyl-2-oxo-1,2,3,4-tetrahydroquinoline-6-sulfonamide,
N-(3,4-dimethylphenyl)-2-oxo-1,2,3,4-tetrahydroquinoline-6-carboxamide,
N-(3-chloro-4-methylphenyl)-2-oxo-1,2,3,4-tetrahydroquinoline-6-sulfonamide,
N-(3,4-dichlorophenyl)-2-oxo-1,2,3,4-tetrahydroquinoline-6-sulfonamide,
6-chloro-N-(5-chloro-2-methylphenyl)-2-oxo-1,2,3,4-tetrahydroquinoline-7-sulfonamide,
N-(3-cyanophenyl)-2-oxo-1,2,3,4-tetrahydroquinoline-6-sulfonamide,
1-acetyl-N-(3,4-dimethylphenyl)-2-methyl indoline-5-sulfonamide,
N-(5-chloro-2-methylphenyl)-7-fluoro-2-oxo-1,2,3,4-tetrahydroquinoline-6-sulfonamide,
6-chloro-N-(3-chloro-4-methylphenyl)-2-oxo-1,2,3,4-tetrahydroquinoline-7-sulfonamide,
N-(3-chloro-2-methylphenyl)-7-fluoro-2-oxo-1,2,3,4-tetrahydroquinoline-6-sulfonamide,
N-(3-chloro-4-methylphenyl)-7-fluoro-2-oxo-1,2,3,4-tetrahydroquinoline-6-sulfonamide,
3-(2-oxo-1,2,3,4-tetrahydroquinoline-6-sulfonamido)phenylboronic acid,
N-(4-fluoro-3-methylphenyl)-2-oxo-1,2,3,4-tetrahydroquinoline-6-sulfonamide,
N-(3,4-dichlorophenyl)-7-fluoro-2-oxo-1,2,3,4-tetrahydroquinoline-6-sulfonamide,
N-(3-fluoro-4-methylphenyl)-2-oxo-1,2,3,4-tetrahydroquinoline-6-sulfonamide,
N-(4-chloro-3-methylphenyl)-7-fluoro-2-oxo-1,2,3,4-tetrahydroquinoline-6-sulfonamide,
6-chloro-N-(3,4-dimethylphenyl)-2-oxoindoline-5-sulfonamide,
N-(4-chloro-3-methylphenyl)-2-oxo-1,2,3,4-tetrahydroquinoline-6-sulfonamide,
6-chloro-N-(3-chloro-2-methylphenyl)-2-oxo-1,2,3,4-tetrahydroquinoline-7-sulfonamide,
3,3-dichloro-N-(3,4-dimethylphenyl)-2-oxo indoline-5-sulfonamide,
7-((2-(dimethylamino)ethyl)(methyl)amino)-N-(3,4-dimethylphenyl)-2-oxo-1,2,3,4-tetrahydroquinoline-6-sulfonamide,
N-(3,4-dimethylphenyl)-2-oxo-7-(pyrrolidin-1-yl)-1,2,3,4-tetrahydroquinoline-6-sulfonamide,
7-(3-(dimethylamino)pyrrolidin-1-yl)-N-(3,4-dimethylphenyl)-2-oxo-1,2,3,4-tetrahydroquinoline-6-sulfonamide,
N-(3,4-dimethylphenyl)-7-(2-hydroxy-2-methylpropylamino)-2-oxo-1,2,3,4-tetrahydroquinoline-6-sulfonamide,
N-(3,4-dimethylphenyl)-7-(isopropylamino)-2-oxo-1,2,3,4-tetrahydroquinoline-6-sulfonamide,
7-(diethylamino)-N-(3,4-dimethylphenyl)-2-oxo-1,2,3,4-tetrahydroquinoline-6-sulfonamide,
N-(3,4-dimethylphenyl)-7-(1-hydroxypropan-2-ylamino)-2-oxo-1,2,3,4-tetrahydroquinoline-6-sulfonamide,
(S)—N-(3,4-dimethylphenyl)-7-(1-hydroxypropan-2-ylamino)-2-oxo-1,2,3,4-tetrahydroquinoline-6-sulfonamide,
(R)—N-(3,4-dimethylphenyl)-7-(1-hydroxypropan-2-ylamino)-2-oxo-1,2,3,4-tetrahydroquinoline-6-sulfonamide,
N-(3,4-dimethylphenyl)-7-(2-hydroxyethylamino)-2-oxo-1,2,3,4-tetrahydroquinoline-6-sulfonamide,
(S)—N-(3-chloro-4-methylphenyl)-7-(1-hydroxypropan-2-ylamino)-2-oxo-1,2,3,4-tetrahydroquinoline-6-sulfonamide,
(S)—N-(4-fluoro-3-methylphenyl)-7-(1-hydroxypropan-2-ylamino)-2-oxo-1,2,3,4-tetrahydroquinoline-6-sulfonamide, and
(S)—N-(3-chloro-4-fluorophenyl)-7-(1-hydroxypropan-2-ylamino)-2-oxo-1,2,3,4-tetrahydroquinoline-6-sulfonamide,
or a pharmaceutically acceptable salt thereof.

* * * * *